US012571030B2

(12) United States Patent
Koshikawa et al.

(10) Patent No.: US 12,571,030 B2
(45) Date of Patent: Mar. 10, 2026

(54) LAMC2-NR6A1 SPLICING VARIANT AND TRANSLATION PRODUCT THEREOF

(71) Applicants: The University of Tokyo, Tokyo (JP); Kanagawa Prefectural Hospital Organization, Kanagawa (JP)

(72) Inventors: Naohiko Koshikawa, Tokyo (JP); Motoharu Seiki, Tokyo (JP); Daisuke Hoshino, Kanagawa (JP)

(73) Assignees: The University of Tokyo, Tokyo (JP); Kanagawa Prefectural Hospital Organization, Kanagawa (JP)

( * ) Notice: Subject to any disclaimer, the term of this patent is extended or adjusted under 35 U.S.C. 154(b) by 819 days.

(21) Appl. No.: 17/798,241

(22) PCT Filed: Feb. 24, 2021

(86) PCT No.: PCT/JP2021/006747
§ 371 (c)(1),
(2) Date: Aug. 8, 2022

(87) PCT Pub. No.: WO2021/172315
PCT Pub. Date: Sep. 2, 2021

(65) Prior Publication Data
US 2023/0340580 A1 Oct. 26, 2023

(30) Foreign Application Priority Data
Feb. 25, 2020 (JP) ................................. 2020-029791

(51) Int. Cl.
*C12Q 1/68* (2018.01)
*C07K 16/28* (2006.01)
*C12N 15/85* (2006.01)
*C12Q 1/6853* (2018.01)

(52) U.S. Cl.
CPC ........ *C12Q 1/6853* (2013.01); *C07K 16/2863* (2013.01); *C12N 15/8509* (2013.01); *C12N 2015/8527* (2013.01)

(58) Field of Classification Search
None
See application file for complete search history.

(56) References Cited

U.S. PATENT DOCUMENTS

2011/0207751 A1 8/2011 Mao
2014/0045196 A1 2/2014 Koshikawa

FOREIGN PATENT DOCUMENTS

JP 2011209281 10/2011
JP 2013520439 6/2013
JP 2015527562 9/2015
WO 2016148215 9/2016
WO 2018136416 7/2018

OTHER PUBLICATIONS

International Search Report received in PCT/JP2021/006747 mailed Apr. 27, 2021.
Written Opinion received in PCT/JP2021/006747 mailed Apr. 27, 2021.
Koshikawa et al., Role of cell surface metalloprotease MT1-MMP in epithelial cell migration over laminin-5, Feb. 7, 2000, pp. 615-624, vol. 148, No. 3, Publisher: J Cell Biol.

*Primary Examiner* — Jehanne S Sitton
(74) *Attorney, Agent, or Firm* — Suzannah K. Sundby, Esq.; Canady + Lortz LLP

(57) ABSTRACT
The present invention relates to a splicing variant derived from exon 12 of laminin γ2 (LAMC2) gene and intron 1 of the antisense strand of NR6A1 gene.

1 Claim, 17 Drawing Sheets
Specification includes a Sequence Listing.

Fig. 2

Skov3

Ovcar 8 migration assay of skov3 line

UPPER SF LOWER 10% FBS,1x10^4 18 Hrs

A

B

Ln-γ2 fusion directly activate EGFR without MT1-MMP processing

SEQUENCE LISTING

```
<160> NUMBER OF SEQ ID NOS: 15

<210> SEQ ID NO 1
<211> LENGTH: 78678
<212> TYPE: DNA
<213> ORGANISM: Homo sapiens

<400> SEQUENCE: 1
accaaccgag gcgccgggca gcgacccctg cagcggagac agagactgag cggcccggcc      60
ccgccatgcc tgcgctctgg ctgggctgct gcctctgctt ctcgctcctc ctgcccgcag     120
cccgggccac ctccaggagg gaaggtgagt cggcttccac aaggaaacat ctcagccctg     180
ggctgagaat ctgcctttct ctgcagaccg tgatggctga acgtacctcc gaggattccc     240
actttgtcca gaaacttgtt agagctccct tctcctcccc tatctggggc tcctccagag     300
acggatttta aatgagacta atatataaag ctatctgctt tttaaaaata gtaagacaat     360
aagctgtgac aaaagagggt cttccttacc ttaaaaatgt tccttcttga tgtctttttt     420
cgaccaaggg gccgctattt aatcaataat gtgttgttat atacgttctt tccccagcgt     480 gtgctttat taaaaggttt tggtggcaat gtttcccatg actgtgaaca ccacaaagat     540
tgcaaaggaa cctcttcaat aatcctgtaa ttgatgtttc aaatttcgga tggaaaaatg     600
agccttaata gtattagcaa taccccttaac ttttgcatca cgttactttt catagtattt     660
tcatgtaata ttcattcaac aggcacttac tgggcacctg tgtcatatat catttgatct     720
tatctagggc acctagttgg ctgtcatgtg ttagacgtta agttcatgta aacaaaactt     780
tgtgagaacc tagcaactct taactgtaag catgtgtcag ctatggcaac attttatggg     840
tgttttcctt gtcacttagt tctatggata tatgcctgta taattgccct gatgttttat     900
```

```
gtttatattg catcctgcat ctgatggcgt ttcaatcatt ctttcaatag gtccaagacc      960
aagagccatt tccacacaag tgcatgcatg aatatgagat aatgctcaca tgcacatgca     1020
attgtataag ccattcccaa tattattgtg cattccgggt gatgctggcc tgaattggat     1080
ttgagtggca tgaataatgt ttgagcatgt gtttgaatgc aatgctacag tcctttttgt     1140
ctaaaaaagt cttggaatta acttccaacc tatcatctct gactaccatt ttcaaaacca     1200
tgtatgattg ccaccaaaaa aaaaaaaaag gtggagataa gtatgtgaaa taatgaacat     1260
attaatttgc ctgactagaa tactatttta ctgtgtatat cgaaacatca tgttgtatac     1320
cttaaatata tatagtttta aaaagtgata aataaaaggt tctgaaaatg gtcatgaagg     1380
gtatgttctc ttagggctgg gataagaagt ctcagcctaa tggaagacat ccccaaagta     1440
aaaatagtct ctgaatatta gaatttaaag ggactgctta tggatcaact acttggaatc     1500
tcttgatttg aaaaatgaga aaatgaaaat gtgtttctca aggccacaca ggcagagatg     1560
aaactggctc ttgatccagg ggctcttagg ctggagcttt ttgagccaca ttataaaagt     1620
aataaaggaa taagatacat cttttataca tgataagtaa tcatttaagc aattttcttg     1680
ttggctatag ttgagtacat atatgtgtgt tagcattagg gaacaaaaat aaatatatag     1740
gatgctatca atgctatttt aataaaatca ggcttaagag gacagagcta ggattctcac     1800
ttcttaaaga cataccagct tctgggcatc catctacccc aagaagtcag aaataccact     1860
gaggctcatt gccactttcc ccttccctgg aggcagacta aggttttatt ctccctcctc     1920
agaggccttc attttttggat tcaatgggaa tgtgaagttt gttgccaggg tagaacacac    1980 atgcttttc attcatggga tgctgggatg tgctagaagt tggactgaaa atatggtatc     2040
tgccatgtct caaagtgacc gtgtctgagt gtcctgtggg ctgcacatat gagaacctaa     2100
agcagtgatg ttgcttcctg gttgtttcct tgcagtagaa attatggcaa tagatgaaat     2160
tggcaagact tcagggttgg gctcagctaa agcacaggct ttagagtcag cctgacctgg     2220
ctttacattt tggttcattc acttactagt tccttattag taatacttgg tgtctgcttc     2280
ttcattgtaa aatggaggca atagtacttc aaccttgtag agtttttgaa aggatgaaca     2340
attactgtaa agtgccttaa aatgcctgga accacatttc tttaaaaagt ccaaagccaa     2400
cagtacagtg tagtgaattc atttgcccag agatcagaaa gaccaaggct ccccttcagg     2460
ataggattgc ctggtgtgag ataaagtggc atgtggcccc agtggtctgg atcttagttc     2520
atagcaggag gtatgactgg agaaggattg agaaagagat aagaaagata ctagaaacgt     2580
agccaccaat atgcttgtga agggctttat gtgccaggct gttcagtagg atggtgccct     2640
gtaggcaaag aagagctgtg aatgatttgt aagcaggaat tagtgtgact ggattcatgt     2700
tttagaaagg tcactcactc gagggcttag agaatgaagt ggagctaggg aagccagata     2760
aatggtgatt accgtaattc aaatgagaga tgatgaagac tttcatcatg gtaatgaaag     2820
caaagaggaa acagattaca gggacattta ggaggtgaaa tctaaagaat gtggtgatcc     2880
aataagtctg tgtgttaggg atatgagtat aggaaagttg agagaaataa ggaagagtcc     2940
aagatggatc caaggcttta ggtttgtaca tggttagaca gtgatgccat taaaggatga     3000
ggactataaa agaaggatca gtctgggcac agtgactcat gcctataatc ccagcacttt     3060
gggaggctga ggtgggtgga tcacttgagc ccaggagttc gagaccagcc tgggcaacat     3120
ggagaaaccc cacctctagg aggctaaggc aggaggatca cttgagcctg tgagggtgag     3180
gctacagtga gctgagattg caccactgca ctccagcctg ggtgacaaag cgagaccctc     3240 tcttttttatt ttagtttaga agggaaattt gagatataaa tttgggggcc cagaggtaga    3300
```

-continued

```
aagcaaagcc ttgaccacag acgagattgc ctaggatatg gaggtaaaag aaacctcagc      3360
acttaaaaaa gagatagagg aacgatggag cagaatcagg aggaatgagc actgaggata      3420
gaggaaaatc aaagaagaag agggttttgt tagtcaaagg aagactgtca gcaacatggc      3480
agtaataact ggtgttcaga tatccaaatg tgtatataca aagaatgagg actatcactg      3540
ctggatttag ccgtcaggtg agttttgaag caattgttct tccagaacgg cgaattcaga      3600
atccatgatt atcatagatc actaatttgg tttttcccat gccctgatgc tagaaaaaag      3660
atgctgtgga tagtaggaag gatccttgga aatgtttatg ctccctcgta gattctgtta      3720
tttaaatcat tgaagtggta tagcatcata cacaaaagtg caggctctgg agtaagactg      3780
cctgggttca aatcccagcc ctatcatgta ccattgtggc acatttatat tttgggactt      3840
gggcaagcta cctcacctgt tacttagctc ctacatctca gaataaggat gataaatcga      3900
tatgaccatt acacaaaaat cactttgcac attgcctggt aagcacttaa tacatgttaa      3960
tagattactg ttattgttac aactaactgc cctgccagta ctgaatttgg tatattgctt      4020
tctgtgtttt aagtggtaac attttgaag ggcctccttt ttactctcct ttcgtcagcc      4080
caagaaggtg ctgaggagcc tttctgctca agcagacatg agccccaagt tttacccaac      4140
aaaacaggaa cccaaagcag gttgcagttt caagactgga tctcgtatca ttccttctcc      4200 ttgcctttt catccaccag acctcatcac acacagattc agcaaatcta ttgcttctca      4260
aaacatgctc aaatataaga tgaccctaca aagatcatct ctcatttccc aatgggaaga      4320
acttccccca cattcaaaga aaggatttgg acaacttgat tatgagaaca tttagcaata      4380
cagatgtagt agtcaaatgt ctctttatgt ttaatttagt aaattaatta cacagatata      4440
ttgaaagtca cataattgat aaaatattat acttagaagt gttgatttgt tcactcacat      4500
tttatgaagt aattatattc aaattatatt cagttatatt catctcacca gatgacttga      4560
gatacagtac tgtttgaatc tgttttttgat gtggtcactg gaaagtacat cattttcaaa      4620
acatttaaaa gatagacaaa ttatccctta gtgtatattg tgatcttcac agcataatca      4680
ctctgaaagg cttatatgca acacctttca gcactcacaa ctatgaagaa atgcaccatt      4740
atgagaattg tttagacagc tgggcccctt tcttactgat aagtctccaa tacattgatt      4800
gaggtcattt tagcttaatg tatcttcccc aaacaatatt tttacaataa agtaattgag      4860
aaagtaccct ataatatgca agattttgaa aggacttaag tatgatcttt tttttcctga      4920
gggataattt tggaaaaatt aaaacctcta ccttatattc aagcatgtac agagatatag      4980
aattgggttg gaggtgggct ggaaattccc atatgggctt aaattctggg tgttctaaac      5040
tgggggcagc cactggttca gcctcactgg cccaagaagc tgagaaagat tgttgatttg      5100
tgattcgtgt ttatgggaaa gtcagggcat aaagttaagg tgttgagaga atcctgggaa      5160
tatctttccc atttaacccca cttaagttct taatggttca aacttactga cttttttttt      5220
ttttttttct gtcctagaga aatttctaag ggcaagactt gaatcatcta ttagagatca      5280
gtgtagaggg ctgggtgcgg tggctcatgc ctttaatccc agcactttgg gaggccgagg      5340
cgggcggatt acctgaggtc cagagttcaa gaccagcttg gtcaacatgg tgaaaccctg      5400
tctctactaa aacatacaaa aattacctgg gcatggtggc atgtgcctat aatcccagct      5460
actcaggagg ctgaggcagg gggactgctt gaacccggga ggcagagatt gcagtgaccc      5520
aagatcatgc cactgcactc cagcctgggc aacagaatga gattccatat caaaaaaaaa      5580
agagagatca atgtagaaat aggagctcca tagaatctgg aatactctca tttagtcaga      5640
```

```
aattaaacct agtaggtgac tgaatcatta ctgggctatg ttttaatata atccccagat    5700
aggtgatgta atgtttgaat catgtccaaa gccaaaggct aagtcttttc tgtctgtggg    5760
tgactgtatg tctgcatatg taattcccca aaaagcatct gcttctttat gtcacaacca    5820
tggaaacaga agagaatggt tcttcctcca gcactgatct atggaagaac ctgagtcttt    5880
cccttctgtt gtatcaggtg aggggtggag atcaattggc caaacgtata gggatcctgc    5940
acttattcag ggcttatatt tacagaattc taaccgcgtc tttttatttta ttgtggggat    6000 atgtatctcc gcattagaaa agaatcaaat tgcagccaaa tcatttccca caactaactt    6060
aaaacttgga caaatcatcc aaatgctcag ctgcactgat gtggggcatt tcatacaaag    6120
tattttatgt ttcaccatgt ttttctctta ttacagtatc gtagaactaa aatgagagtg    6180
ggcctcaggg gttctctaca agagcctctc attttatgca tgagaaaaat gacacccagt    6240
gaggtaaatt aactgcccaa tttcttactg ttggtcatag cagagctggg ctccagcatg    6300
tttcatcctt ttataggtag gaaaattgag gcacagaaga gtgactgctt tgaccaaggc    6360
cagatttcag ttactagttt aatgttcttt ttctgagata actccttggc atatttctca    6420
tttttctttt tttgagatgg agtcttgttc tgtcacccag gctggagtgc agtggcacga    6480
tcttggctcc ctgcaacctc cccgcctccc agcttcaagc aattctcctg tgtcagcttc    6540
ccgggtagct gggactttag gggtgcacca ccatgcctga ctaatttttt gtatttttag    6600
tagagacggg gtttcactgt gttagccacg atggtctcag gtctcctgac ctcgtgatct    6660
gcccgcctcg gcctcccaaa gtgctgggat tacaggcatg agccactgtg cccagcctga    6720
attttcattg aaactaatct tcaagcttga tggaaccttt atctactgtt gacataccac    6780
ctgtatttct aatgaagaca tctatctcgt cttttcagaa gtctccattt gtgtatatga    6840
ttcaatatat tggcctttcc tttaaaaata tcagagaaca acaggttaaa actaagcaca    6900
gctctagttt gtggggcatt aacaagagaa cagatttcaa attaccaagt tttctcttcc    6960
ttttgttcca ctctgttgtc aggttatcat gcagcttgga attgaccaag tggctcagtt    7020
taggatcgtt gatagtactg tgataagact ttctctttta gcaatcattg ttctttaatg    7080
actgttgaca ttttgcatct gtatatacgt aatcacgtcc agagattatt tctgtctccc    7140
tgctacagac ccttgtaagt tttggagtct ttcagaaaga ggtctgtttc atggccagaa    7200
tgttgaccat gtaagcttta tacatactta ctgctgtttc aaatcatggc ccattttgct    7260
cttggtaaaa ggatactttt tggtagggga ttcctagtgt ttaaaaatcg tttttcatcc    7320
caaatagcct ggcctacttt gggaaggcag ttgatccaac agtaatctga agctgctgct    7380
cttgccctat ccaggcagtt gtaccatggt aggaggggat cttcacattc tgagatctgc    7440
agggagcagg ggagaggcca cagtggacct ggcataggaa gtagtagtgg agaaacagca    7500
tatttgttca actgagatgc aagatactcc ctgatgtagt cttcatggtc cagtctcttc    7560
tcaaaatgtt tgttacttct ctttatggat gtgtaaaggt agtttggctc ataagagctc    7620
atttaattca ttcttctgac tttaggcaat acagtgtttt tgtttttgag atggagtctc    7680
cctctctcac ccaggctgga gtgcagtggt gcaatcttgg ctcctgggtt caagtgcttc    7740
tcccatctca gactcctgag tagctgggat tacaggcgca tgccaccagg cccagctaat    7800
ttttatattt ttagtagaga tggagttttg ccatgctggc cagcctggtc tcgaactcct    7860
gatgtcacgt gatctgccca ccttggcctc ccaaagtgtt ggaattacag atgtgagcca    7920
ccatacccag ccagcaatac agtttttaatt catcttttttt ctgaaaaaaa aaaaaaaaaa    7980
tctgtaagta agatgctata aatgcacgcc atgcatattt tcccaacatt gcaaatgcac    8040
```

```
atgaattacc attgttcttt tgtgaagact aagaactata taatggtatg taagcccaca      8100
cacataccta aatgcttgta tttttgtgaa gggatgtagt gatagcaaaa aatctttgcc      8160
taatctcctt gtacaaaaaa agtattgttc acaaaagcag taaggattta aaaaggaaga      8220
tttattgttt ttttttaagg aatcaatgaa acataaattt aaataattga aaaatcatgg      8280
tttatacttc aattatctcc aaaaggcatt ttagtacaaa ttagaatctc cttttttaact      8340 tctctttatt cagacacatc atagaaggtt tctttccttt tggtcctctt tgcttcaggt      8400
atttacctct ggcatccctg gaatctctga ttcccttat ttcaactgct tcttagaggg       8460
gcataggata ccttttttcta ggccatgcaa gaaatgtcca gagaacacta tgctctttga     8520
ataacagtta aatgtccttt ctatgctgga atgctttct ttgtaggtaa cttcacagaa       8580
atgtataacc ctttatttct gtggtcagaa gagtgtggag ttccatggag gtggttgctg      8640
tcatatagaa tcttaccaca atcacttcct gagtctatgc tgcagctgac agcagctgtc      8700
ttgcggtaga gcctttgaca gtgccagcta taactctaat gtcctcagtt tgccttccct      8760
ttcacctgtg agcttactca gactgaaccc tcagttttac ctttaccctc cactcctttg      8820
ctagtcagac aaaacttggt gtccccagtt tccctgttca ctgggacttt cttcccctc      8880 ctcattgtct gcctgggcac tggtgtccca gtggagtgtc aggggaagac atctccaggt      8940
gtgaactcct gatggagtcc tcaccaggct gagtcatcta cagttcacac gggtacattc      9000
ccaagtctag gctgtgatat aatgtactat gaactctcgg tgaaacaggt gtctcctctg      9060
aagccataat cattcaaaag gaaatggcag tgatctgagt ttcactgact cttgatgact      9120
ttggagtatt cagagttgaa aaaactgacc catactttat gattcaaaat tgcctgtgag      9180
attagagaac tgagctctgt cattcctctc atcctagcac ttcctgcctc agccttactc      9240
acattgcttg gacatttaaa tgtcaactgg tgccgtgccc tttatttaaa tgaaacaaat      9300
ggatcaggca ggatatggta tcagtttct ggctgtggtg gcttaaaatg tggctatgaa       9360
aaatttgcaa aagaagccta aattcagcta aaagccttag tgagagaagt accatttcag      9420
ttttcttatt ctaattaggg aacatattgt gacattcttt aagaagataa aactagaagc      9480
agatattcac acattaaaca atgaagttca aggccagttt aaatgatgaa ggattcagat      9540 tttgtttttaa aatatctgct taagccgaca aacatattaa aacttggaaa gaaaaattcc      9600
atgtaggagg ttttaaaact agaaaagtcc ttataagcat tttcatcatc acatgtaaat      9660
ataatataat aaaaacattc atcttttcat cttgaatgtc tcagacttga agacatggat      9720
ttttgcaaag aggatcatag cttctgatgc ctttgatatc aaactgataa atgacaggta      9780
gtatcttgct ttagattgca tacataatat gcaatttgaa tatttgtcat aattatttat      9840
ttttgataaa aatgattttt tttttttgag atggagtttc actcttgttg cccaggctgg      9900
agtgcaatgg cacaatctca gctcactgca acctctgcct accgggttca agtgattctc      9960
ctgccttagc ctcccaagta gctggtatta taggtgtgtg ccaccacgcc cagctaaattt   10020 tgtattttta gtagagacac ggtttcacca tgttggtaag gctggtctca aactcctgat    10080
ctgaagtgat tcaccggcct cagcctccca aagtggtggg attacaggca tgagccactg    10140
tgcctggctg ataaaaattt ttaaaataca ttaggataaa tttctattta aaggacccttt   10200 tcaataattg cttttgtact gagaacaacc tttgctagat ttttaaaagt gggtatatgc    10260
aactgaaact ttattcacca tcttcagtat agccttttac atttggactt cccattgaaa    10320
gacctcatta taggtgactt catggaggca actgttgcta tctttgaaca taaaagagtt    10380
```

-continued

```
gtcagtttac atgagagcag tcttttgact cagaagaagg gaatggtatc caataaggta   10440
tattaagatt tagttttttag tgtaacttct ttgaaaaaat gaaataggag actagttgag   10500
attgtcagcc ccaatttgtg tctgcccacc atgatggttt tcttttataa agcaagaatt   10560
ttaagaagca gaggaaatga agacataaaa tgaagtgtat gtgaatgaat ggaagagaga   10620
tgaagatgtc ccagtggtga gcgttatatg aaattaggct ggaaaagtag atagggtaag   10680
accatgatag tccttgtagg caatattgag gaattctggt gcttaacttc aaaggaaagg   10740
aaagaaacta cagaatatta agcagagaag ccatgataca atttgtattt tggaaagatt   10800
ttctgattgc tgagtggagg gaagcaaaag aagttgcagg gaattcagct aagaagtgat   10860
ggcaggcaag agatgattga ggtttggtct agatatggct atagtggaga tggacttgat   10920
tggatttgag atatttagtg ggttatatca acaaaattca gtgttaaata ggcaggtgag   10980
aaagatggag aacctgtaag gatagcttcc agctttccga cttgaaggca tggcaatcat   11040
aagtttggtt ttaaacaggt tttgtgtaaa gaacttttga gataaccaat tggaaatgta   11100
aagtgagctg ggcgcagtga ctcgtgcctg taatcccaac actttgggac ggtgaggtgg   11160
gcaaatcact tgagatcagg agttcgagac caacctggca aacaaggtga aaccctgtct   11220
ctactaaaaa tacaaaaaat tagccgggcg tgctggcggg cgcctatagt cccagctact   11280
tgggaggctg aggcaggaga atggcgtgaa cctgggaggc ggagcttgct gtgagccgag   11340
atcgtgctac tgcactccag tctgggcgac agagcgagac tccgtctcaa aaaaaaaaa   11400 aaagtaaaag taataagtaa ataagtaaat aaataaagtg gatggcagac atgaggacct   11460
gaagttgagg atgaagtttg ggccaaggaa gtatcttcgg atgtcaacaa ttacggtggt   11520
tattgaagtc cttgtcatgg atgagattac ccaagggaga ctcagactga gacgttgtgg   11580
agattaagga gccctgagga gcaccgacat ttagagtagg ggtaaggaaa ggagccagca   11640
aagccttgaa tagggaaggt cagaaggcag acagacacct ggcagtatga catcattgta   11700
tccaagggaa gagagttgca caaggaagg agggaaaaag atttgatgtc tcagaaaagag  11760 aatgagggac acatgcagga aaggaaacac agggcacatc cctttcctct aaataagaaa   11820
gataattgag catcatcttt ttttttttct ttcttttttt tttttttta attgagacag   11880 agtctcactc tgtcgccagg ctggagtgca gtttcgtgat ctcggcttac tgcaacctcc   11940
acctcctgcg ttcaagtgat tcccctgcct cagccacccc agtagctgga actacaggtg   12000
cctgccacca cacccggcta atttttttgt gtattttagt agagacaggg tttcaccatg   12060
ttggccatga tggtcttgac ctcctgacct catgatctgc ccgccttggc ctcccaaagt   12120
gctgggatta taggcgtgag ccaccgtgcc gggctgagca ttatctttaa atggttcata   12180
gttcgactaa ttcacgggag attacaggtc acatcatata aacttgctgc tgtttcactg   12240
aatcagtttt agtgcactaa gcaaccgaaa tggtagcaac agcaacaaag cactacgtaa   12300
tagcaaccag cacacactgt caggtttaaa catgatgctc aaattcctag ctcctgacac   12360
cgtcccacac agccgccaag tacactacct atcaaggctg cctgagcact gcaaactgat   12420
ctcatgctct gaggcctgcc tcatcgcctt gccctcctcc cacacagccc taggctcgct   12480
gcccgttgag gtggcaggca gaaagcattg cagctctggg gtcatagacc acagatgggt   12540
gggcagtcct agggtggaaa tagttcatct ggtatgagca gcaacctgaa agtcccagac   12600
ccttaatctc attgaaaatc tcatgttcct ctcacaattc tttctgttcc catctcacca   12660
tggatttttt tgcttggaac attagttttt ttacactgaa tgtcatatat gtagacaatg   12720
gaaactttgt gtaatgtatt ggggaaattt gaaagtaggc ttctggacgt cagggagatt   12780
```

```
tctgtatgtt caggttcttg ttggctttc ttttttttt ttttttttt tttttgagac    12840 agagtctcgt actgtcacct aggctggagt gcagtggcac catcttggct cactgcaacc    12900
tccgcctccc aggttaaagg attctcctgc ctcagcctcc caagtagctg ggactacagg    12960
cttgcaccac cacacccagc taattttgt attttagta gagatggggt ttcactatgt    13020
tggccaggat ggtcttgatc tcttaatctc gtgatccacc cacctcggcc tcccaaagtg    13080
ctgggattac agacttttct tagagtcaga ctgcctatat tccttccttc ctttctcctt    13140
ccttccttcc ttccttcttt ccttccttcc tccctccctc tctttcttcc ttccttccct    13200
ccctcattcc ctccctcaat tcctttctct ctccttctat ccatcatgct atccaccatc    13260
tttccatcca tccatccatc caagcactgc attaggtaca gtggggatat aaggtgagaa    13320
atgctgtaga agaagtaagt catagacata aacagtgatg acacaggata gaacgaggca    13380
aatgctgaga gaggtgagga tgaagtgctc tgggctttca cgggagagag aagctgccag    13440
aaggtatccg caaggaagtg cacaatctga tttatgcacc taaaaagaag actggctgtt    13500
acctggaaat agatttaggg agggtggaag cagggagtgc tcctgataaa ggaaatagca    13560
agcctaaaag ccagaggtgg gaaagggtta gtgcagccta gatctgtgca ttggagccca    13620
gtgaactctt gatgaggtaa agttggaaag gttggcaggg gccacatctg ctgagttttg    13680
aaagaagttt ggattttaa ttttgtcatt accgttaaag cactaaaaag catgatgatt    13740
tcacagatta tacaaagaca gcgattagat caccttagtg aaaagcagag catgttttc    13800 agtttagaac aatagaaaga gggccgggcg cggtggctca ggctgtaat cccagcactt    13860 tgggaggccg aggcaggcaa atcacctgag gtcaggagtt caagaccagc ctggccaaca    13920
tagtgaaacc ctatctctaa taaacataca aaatcagccg ggcatggtgg tgggtgcctg    13980
taatcccagc tactcgagag gctgaggcag gagaatcact tgaacctggg aggcagaggt    14040
tgcagcaagc caagatcgcg ccactgcact ccagcctggg cgacagaacg agactctgtt    14100
tcaaaaaaaa aaagaacatt agaaagagga cctgcttata gaaacacaat catatgtatg    14160
ccaagtgatt gaaatttctc gtaattgtat gcctcaaaag ggcactgttt cttatgggaa    14220
atttaaaatg agatcccgat gaactgctac tactgatgat gattatttca aggccttgtc    14280
ctgcgtacaa cctgaggaaa tattttctgt ttccttttat tctcctaagg ccacagctgg    14340
gaaaccgcct ttgcccctt gcttcctgtc ctaacctgtt ggagctgcgt gttttagtga    14400
ggggtgggag tgttgtgaag tgagcccgag ggatcctgct cgcctcactc tattgtttaa    14460
ggaggggctc cagctgcttt gatctgcgtc tctgggtgag tgtgggtggt agtgggcagt    14520
ccagcctgtg tctggctgcc tggcggtctt tcctaagaag caccttgagg gtcagcaact    14580
gtgtgctatt atagttatta ttataataaa tgcttcagtg ccagagaagt agcatacagc    14640
agtcagacgc aattaccatc cacgcacgct ttactagact taaagaaatc tgtgaaaatc    14700
tgactcaaat gactccgttt cagatgggtt tatgtaggac ttgaggtaaa cttgcagagt    14760
ctcatttctt tggctgtgga gagaatgctg gctggcagaa tcaaggattt ggagggagct    14820
ggagtgaggg ggcagaaaga ggagaggatg aaaccttgaa gaagtgtccc tggctttgta    14880
ccaatgaata gtcaaaggaa tgatggatgg acctagaac cagagttcag tgaaagatgg    14940
agagaaacct gcttgttttg tttactgacc ttagaatggc ttcagatctg ttcagggttt    15000
gagtctgatt ttttaaattt tattttccga tgatgtgcaa tatcttaatg ccagatcccg    15060
aacccatacc tgggttccaa cacacaaatc cttgcatgag ctctagaata tactgagctt    15120
```

-continued

```
tttcccacct tgggctttta ggcttgctct ttcctttgtc aggggcactc cctgcttcca   15180
ccctccctaa ctccatttcc ccataacagc cagtcttctt tttagatgca tacatcagat   15240
catgcactga ttcctgttca agtaggaaaa catggataat atgatacatg cttgacacag   15300
gcaaatatct ttggaaaaat aaaacattag caaccccctt ggctgggtgc ggtggctcac   15360
gcctgtaatc ccaacacttt gggaggctga ggcaggtgga tcacttgagg tcaggagttc   15420
acagcctggc caacagggtg aaaccctgtc tctactagaa atactaaaat attccattgt   15480
atttcagaag attataaaag ctctaaggtg aattttgaag tcttcatcag catatccata   15540
ttaaaaggag atgacagaag ccaaaataaa agaattatgg gctgacaggc aactggatta   15600
aaataagcat cagtttcatt aaaaatggct aacttgaaga taaatctttt gactccagca   15660
ctctagagga tctaaggtga ccttgatgga cagtggaaga aatcacaaca tggaactccc   15720
tgaataaaaa tttattgact taaaaaaaat actaaaatta gctgggtatg gtggtacatg   15780
cctgtaatcc tggatgctcg ggaggctgag gcatgagaat cgcttgaacc tgggaggtgg   15840
aggttgcaat gagctgagat cacaccactg cacttcatcc tgggtgacag aatgagactg   15900
tctcaaaaaa agaaaaacag caacaacaac aacaacaaaa aaaaaaaaac aaagaaaacc   15960
acacacacaa aaaaattagc aaactccttc tttgaaatgt tactggctca taaagtctga   16020
ttgttcaagc atgcagtata gcctccctat tagatgtgat gtttattaaa ttaataaaat   16080
aaatatacat ctcattgacc aaggataaaa gaaggaaggg ggaaaggggg cttaaatcag   16140
caaaacaaaa tctaccgatg aggtactttg gaaataaaga tgatttatca ggaaagagta   16200
aaagaaaatc tgcaataaag tgatacagac aaatagtttg atgtatttgt tatgtaaaca   16260
attcataaga aaaacattgt gccataagaa aaacatagat aaatggacaa agatcatgaa   16320
gcagacaatt atgaaaatag aactaaaaca gcaaactggc atatggcact ttctaccctc   16380
cttcccaccc atcttactac ttcccaactt cctatgcctt tccactgctt tatatatttc   16440
tccctaacaa ataccactat cctaatattc tctcttgata ttacttattt atcttgttta   16500
ttttctttcc ccccaaattg catgtaaact ccgtgagggc tgggacatct gttggttttg   16560
tttgctactg tatgcatccc attgcctaga actcagggaa ggtccaagac aaccatctat   16620 gggttttta aagttcaaca gaacattcat tcattcattt gtttgttaaa aaaagactaa   16680
atgcctacca tggaccaggc actgtgtgat ataatagggc ttccttttc cttttcaaa    16740 agcatgagat gtgttttcta cctgttagaa ctgcaaagtt gagtgcagag atttgcctgt   16800
ggacacagct ttgtttcaaa aatatatatt tttttaattt tggccaaaat tttaaaacca   16860
atagatttca tacacaaagc tggatttctg tcttctttta aaagaagagt tgatgttgac   16920
tacaacaggc atcaattgca tgtggctgca actggcaggg ggtgaagtgc tgcttcttac   16980
gccctttggg cagaatcccc accacttcct gttgccttac tctaagcctg gcagtgccct   17040
ttggcaactg gtagttgcca aaccatggta gtagttgggc aggtattggt cacagaataa   17100
agaccacata caagctacat tacaccgttt tattaagccc agttgcagga atattctaga   17160
attttaaata gaaaagttgt ttcctgcccc ccgcccccc tcacccctag tagcgagagt    17220
aagtaataaa tggttttagg gaagttagtc tcaatttggg agatggtttg agagagacca   17280
tttttcaaac acattaatga tgaaaagcat cattccatgc aaaaggagct tggaacaagc   17340
tctcccatca ttttcttggt gggaccattt caaagactca atactgagtt aagtgcaata   17400
tagctgggtg tttaatctca gtgcagcttg gtaacttcaa agtcctgcag gcaaggctgt   17460
agagagtgtc ttcacggagt tctcatgcaa tgcagatacc caaggccaat acattcccca   17520
```

-continued

```
gacatgaggc ccatacatcc cctcactcta gatggcattg cccttggctt taagggagac    17580
ccatttgaaa ggaaaggggt atgtttgcaa taggcttaga atctgttggg caggctctgg    17640
aggggagatg ctggctaagg acctccatcc ctggaaccgt aatgcaactc cattgaaggc    17700
tgtgcattta aaggacaatg gggcaggcat ggtagctcat gcctgtaatt ccagcacttt    17760
gggaggctga ggtgggagga ttgcttgagg ccaggagttt aagaccagcc tgggcaatac    17820
cacgagaacc tgtctctacc aaaaagtaac acatttagtt gagtgttgtg gcatgcatct    17880
gtggtcccag ctactcggga ggctgaagtg agaagatggc ttgagcccgg gaggttgagg    17940
ctgcagtgac ccgtgatcac accactgcac tccactctgg gtgacagagt gagactctgt    18000
ctcaaaaata acacaaaaga aaataggctg ggtatggtgg tgcacacctg taattcccag    18060
cactttgaga agccaaggta ggcggattgc ttgaatccag gagtttacga ccagactggg    18120
caacatggtg aaaccccgtc tctacaaaaa caaaaaacaa acaaacagaa aaaaaaaaaa    18180
aaaccactac aaaaattagt tgggcatggt ggcacacgcc tctattccca gctacttggg    18240
aggctgaggt tggagaatcg cttgagccca ggaggttgag gctacagtga gctgagattg    18300
tgacacagca ctccagcctg gacaacagag tgagatcctg tctcaataaa aataaaaatt    18360
aaaataaaag aaggacacct attatttttca aagtagagct ttagaggagg agacagaaga    18420
gggatgtgat agaaaaagat tataacaagt ttatatattt tgaaaagatt gctctgaata    18480
aatatataat gagctgccct tatgaagtta atttttacca ccacaaagca tgttcttttt    18540
tttttctttt ttgagacaga attttgctct tgtcacccac agtagagtgc aatggcacaa    18600
tctcagctca ctgcaacctc ctcctcccag gttcaagtga ttctcctgcc tcagcctccc    18660
aagtagctgg gattacaggc acctgccacc actcccagct aattttttgta ttttttagtag    18720 agacggggtt tcactatgtt ggccaggctg gtctcaaact cctgacgtca ggtgatccac    18780
cctccttggc ctcccaaact gctgggatta caggcgtgaa ccactgtgcc cagcccatgt    18840
tctaaataag aaaggcacaa tgaaaaattt gtagttattt tgagattgct tccaaaaggc    18900
atccagggca gggagggcat tggctcattg ggttagccag atgaagaacc tcgcaaggac    18960
tgctgaacag tgaatttagc tcttgtacgt gcatagtcat gtacttggta caaatttcac    19020
agcacatgac agctgtgtgg cacatctgtt ggagatccaa aaaatcagtt tcacaagcat    19080
tggttgggaa agattcagct tggcactagt tctgagaaaa gccctgggac tttgaattgt    19140
gtgcaaatgt aatatgctgt aagttcactg aaatgttagt ctttgcccat gggataaaaa    19200
tatctagtcc tgttacaagc caagctgttt aaatcacact tgcagtactg gtcatatgaa    19260
gaaggatact ggaaattaga atttgttcct aggatggtag tcaagaagaa tctagaaatt    19320
atgacatagg aagtggttga aagacttgga gatgacagat ctgtagtcca acttgaacag    19380
gaaaagacta aggagggaga tgccatagct atcttcagat tcacaaaagc ctgatgacgc    19440
agggcccttt ggatgtaaaa caacacccaa agattatgtc tgttggataa ataaaagaat    19500
aaaaagagag tagggggtgtg tgtgtgtgtg tgtctgtgtg tgcctgagtg ctgtatgtat    19560
ctgtgtgtgt tgtgtgtgta tgttttcagg caagagcaaa aacacatgat gaaaattaca    19620
gaaagagagg tagatttaaa acaccatata aaaatgttac tgtttgtaac aaccaagctg    19680
aatgaccctc tattagggat ttataaaaag aatgtctaca tgcaatggta aactcaatct    19740
tgagaaggaa cataaaatgg aaagatgagg gctttggagt cagacacatc tgggagcaaa    19800
ttacatcttt gccatttagc tgtgtgactt taggcaagat acctagcctc tctgagtatt    19860
```

-continued

```
tgttttcca tctattaaat ggggataata aaacccatgt taaaatgttg tgagaattaa    19920
ctgagctgtc gaatgtaaag tcctagaaac agtatgcttt ggataagtgt tagctgactt    19980
ttctagatta gatgtcatcc aaagtagaaa gagtgagtta tagaaattac tgtaaggcag    20040
tcacttagca ggtccattag atgtacgtgg tcaccgctgg gcacggtggc tcacgcctgt    20100
aatcccagca cttttgggagg ccgaggcagg cggatcacct gaggtcagga gtttgagacc    20160
agcctagcca acactggcga aaccccatct ctaccaaaaa tataaaaatt agctgggcat    20220
ggtggtgcgc acctataatc ccagctactt gggaggctga ggcaggagaa tcacttgaac    20280
ccaggaggca gaggtttcag tgagctgaga tcatgccact gcactccaca ctccagcctg    20340
ggcgacagag caagacttgg tctcaaaaaa aaaaaaaaaa agatgtacat tgtcccttg    20400 tattgtcagt gcctgacaca gagcctgcac agggagccac tcagcaggtg atggcacatc    20460
tgttgacttt attgtcagca ctatggttaa gtcacgccct agaaacatat tctcaatatg    20520
gcagcatggc caacagagac agcctgtgta gggaagggag gttggtgttc gcatcaggca    20580
gaggttcaaa tctcagttct ccactgggtg gagttacttc acctttccga gctgcatgtt    20640
tctcttctga ggcagtacgt gtttcatgga gtgagtgatg aaatcgcata tgcaaaggca    20700
tttgatattc ttttcccaga gggatcctct ttacaatcca gggaggcaga taatgcagtc    20760
tgtatggaag aaaaaacaag attcagaaaa ttgaagtgat gtgcccaagg aaatagcaga    20820
attggtattt gattctttcc ttttaacctg aaggcccatc atctctctct ccgagaccat    20880
gacggaaaca ttttttggtg tctcagtgtg ccgggtacta tgctgggtgt ttccgtgttt    20940
cgcttctttg ctgttcgggt ccttatggag atgttagtca ctttgcgagt ctctttggaa    21000
catctgcagg atgggcttcc tagatacttg agaaaggtca ttcttcatgg gacacttggc    21060
tttgggagga gacatgtgcc cagacggtca cgtccactcc tttgccttga cgggcaccgg    21120
tgggatgggt gttgtgtatc ttgagcagcg acaccatcgg ctaatagctg tgctgagtcc    21180
gcagctgccc atcctcaggt ctccgtgagc ccacacactt gctctgtggg attgcagtgt    21240
tttgaaatga actccttgca aacatttaaa tcagaaatat ccgcataaaa atgtaattta    21300
acattttggg tttctctcga ggaactggac agtctggcaa ccctgagccc atgttctccc    21360
agacagcagc ccaccagcat tgcatagtgc ctacttcctt taagtggagc aggcgtcccc    21420
ggggtccctg cactgccaat tgcactccca tatcttcctc ccgcaaggag tgtaggttac    21480
catatagtac tcatgcataa tttctatcaa taataacata aacacctgct agaacagttc    21540
ctgaggtgtt tttttttttt tttgacgatc tcttttgtat gcttcctccc cagtctgtga    21600
ttgcaatggg aagtccaggc agtgtatctt tgatcgggaa cttcacagac aaactggtaa    21660
tggattccgc tgcctcaact gcaatgacaa cactgatggc attcactgcg agaagtgcaa    21720
gaatggcttt taccggcaca gagaaaggga ccgctgtttg ccctgcaatt gtaactccaa    21780
aggtagctga aaaggacgga aagagggaga gggagatgga gcagtgggga gacaagaggg    21840
aaggaaggaa ggaggaaaag aagaaggaag ggaacaacgg aggaaaaaga aagaaaacag    21900
ggaaagcaag caggccaaga gggagatgtt caacctcacc aacaactggg aacctaccag    21960
acattggtct ttttagcagt ttcaatctga aaggaaacat gtttctctta agtaggggtt    22020
ggtggaacca gttgggacct tgagggcatg ttgtcttgaa ttctaataca aagagtcaca    22080
ttattaactt ttccaggcag gtgacagtct tttgcaagca gatgacaaag gaagcttgca    22140
ctctttcagg gatagttctt catatccata gccatccatt tgaccaacct cttgaaaaat    22200
aaggaattag aaagatctgt ttctagtgct gtgctaggtg ctagcaatat gaagttgtac    22260
```

-continued

```
taataaagga gacagacaag taaacaggaa aattgaagtc tttcattagg ttgctaaaaa   22320
gataaaacaa aataacaaat aggaaacacc taatggggtg gctggttcat aggagagcta   22380
gtttgttttt ttgtttttgtt ttgtttttttt gagacagggt ctcacactgt tgtccagact   22440
ggagtgcagt ggtgccatct cggctcactg caacctccgc ctcctaggtt caagcgattc   22500
ccctgcctta gcttcctgag tagctgggat tacaggcacc caccaccacg cccagctaat   22560
tttttgtatt tttagtagag atggggtttc attatgttgg ccaggctggt ctcgagtgcc   22620
tgacctcgtg atccacttgc ctcagcctcc caaagtgcta agactacagg tgtgagccac   22680
cgcgcctggc tagttgtttt tttttttttt tttaaagtat cccacacagt gctatattca   22740
tataactgta ggtctttgct gtacacacag atacatacac tgtgctgtat tcattgtgga   22800
cagacagtaa agacaagtta gtaaatataa aggggagag agaggtggtt ctgtaaataa   22860
gatttttttt ttaaacggtt catttgtcta ttatctttct ggcattatct acttttcttt   22920
gctagaaagt gtttaacagc atcctgtgat aaatattgat ccacttaaag catacagcct   22980
tattgcatgg caatgactta gtgtagtagg tctgtggaac caactgatag ctgcagcttg   23040
aaagaatcta aaaatgggca gattctggtg cagccatgag ttgctggtag agtggtttgg   23100
gagtcttata gaaaactggg tgaccctgtg gtgagatagg cccatatcgc agcagtcacc   23160
ccccaaattc acctaagttg ctgtcacaat gtggtttgac tcagattagt ttagctttgt   23220
tgtgtggaat ttgcatccag aatctttggg atttagcagt cctccctatg aatcaaagaa   23280
cttcataaaa aaattaaaag acaaattatt gcattttaat gggcatttaa cctctctgaa   23340
gagctcctat tgccttaggt catgcagctt cattgtgagt caccagagtt gggtcatccc   23400
agtgaaatga tcagtgagaa tgaaactaga aatttaattg gctcagcttg aaagcctggc   23460
ctgaagacaa ggttattagt ctcagggtag accaggaacc tgctgcctag cacagaagga   23520
tggtaaagaa ggatttacca tgtcatctct tctgtttcag catgtagtct actgcttgcc   23580
cagtggtaag ggcaagtgaa actggctcct tcttttattt tgggtaatag atatcccaga   23640
ctcagtggga acagcttggc aggaagtggt ggagcccagt attgatttat gtcttatatg   23700
atagttaaca tgtgccatgt gccaaccctg ggccaggcac ttttctaggt gcttttaatc   23760
cagtaattaa ttaatcttca caaataacta aagaggggc tatgtttttt cccatttcac   23820
aaatgatgta gcagagactt agggagggag gggaagaaac ttgtccaagg tcatagagct   23880
aaggggcaga gtaagagttc aggaccaggt ttgttgacat caaaggtaat aatgtagagt   23940
acagtggtgg gttatggagc caggcagcca gggtgcaaat ctggacacaa ccaccatcat   24000
cattaggtca ctctgggcag gttccttaac ctcttgctgc tccagcatcc ccatctgtta   24060
aagagtgttc atgatattca tgtcatggga tcctgtggag ataaaatggt gtttgacaag   24120
cacatggcgg gcaactcagt aaattgtgaa ttgatgtagt tgttttttctt attaagacag   24180 tggggaaact gagacctaga aaaattaatg aatggcctaa agtcttccag caactgattg   24240
caagaactaa agttgtaagc cagatcttct gatcaagaat aattctctta ttccctccat   24300
atgaaagaaa aaaaaatcag aatggcattt ttcaatgccc aaaagcagac aatttatgtg   24360
tacacaaaaa gcttgatgga tattatttcc taagatctga ctaatgcttt ataattttcc   24420
aaaacattat catagatgat gtccttctta gtcctcataa cagtctgaca acaatgtgtt   24480
aacacatcca ctgttaaaga gatgaagaaa ctgaactttc agggtccaaa ctgcagaggc   24540
tgaaagacac attggtgaca gagactgttc ccaccatgtg ctgtccccag ctgctcctca   24600
```

-continued

```
gctgcacatg tcaccaaacc actagcacaa gtttaattcc ctatgtgatt tctcagtatc   24660
ccaattagcc agaggatatt tttcactttc agataataac ttgacaggga aatctgttgt   24720
atattccatt tcaaatgcaa aataacatgt cttacaaaaa aatgctatca ttacatgtat   24780
gtcaaatgaa gccaatggca ttaataaacc ccagagtagt caccaatttt ggactttata   24840
tcgatttccc aaaaatgcag aaattaggct tatttttaga ttatgacttt gtgggctcag   24900
caacagggct gagttacctt cagctcttcc aaccacatat ttaagccctg ataacctttt   24960
gcagatactt tgaaattcac tgcgtgtgca agttttttcc tcccatgaca gctaagtttt   25020
tgaggtctat gtgatattgg acttactctc ttaattttat attttttac atatctttga   25080 tgcttacagt gtattattca gactataaca tttgagtaat tatttaaaac atgttttaa   25140 atgcaagtgt atatattttt aaaagggttc tcaaaaggat gcaaattctc tgtttatatg   25200
ttttgtttat ttgtttttat tgggtttgtt gttgttgttt tgagacaaga tctcactctg   25260
tggccaaggc tggagtgcag cggctccatc atggcttact gcagcctcaa actcctgggc   25320
tcaagcagtc ctcctgcctc agcctcctga gtagctcgga ctactggtgt gttccaccat   25380
gcctgactaa ttttttattt ttttgtggag acagggtcta tgttgcccag gctggtctca   25440
aattcctggg ctcaagaaat cctcctgcct cagtctcccc taactgctgg tattacaagc   25500
atgagccacc atgctcggcc ctaaatttta aatatttatc attttttaat accttcctga   25560
gtcttcaaat gcatgtaggc tatatctata taaagcatga atgtgcttac tgggacacaa   25620
atttgaaaca ggaagttatt ccttatctat tctttaaaac caattgttca caatccctaa   25680
gtacagttca tgatgtggga attggggcag gttgtttttt ttttgagtga gactttgaag   25740
aaccagtgct attattttgg aagttttgga acatgaaata agtcagtcat attcagagtt   25800
agagcctgaa ttacttcttc ccccacttta ttaaaataat tcatttctga aaaactactg   25860
cagggagagt tttctgaagt tgaaagtgta ataaatttgg atgcagaaaa aatgtgtttc   25920
tgatccccaa atcagcatcc attcatgtta aaaacaacca aatttcatca tgagggactt   25980
ctatttaaca ttacttatca gagcattatt caaaaaggaa ttttccttcc ttctgctgac   26040
cactcacaga gcaatgatca tgaagtctct aaacatcaaa ccaaatagcc tctcttcatt   26100
ctcatcttat ttaaaagctc tcttgcctta ggctctgaaa accttccttc tctcctcctc   26160
ccctcaccct cctagacct ctcctccctg ccttccattg ctcattgttt gattagaccc   26220
tgccctgaga cttctccctc tccaatcatc ctctcttaat agatgggctc tatctctgtc   26280
ctcaccactt cccctcctct ctccatctac ttctggactg atctcacatt tactatggct   26340
tcctattcag cctgagtgtt gagggctcct agatcttcat ctctagactc tgagctccag   26400
atgaacattt ccacctttta tatgcccta gaaactcaag ttcatatacc caaaactaaa   26460
ctcattatct tctcttgata attcaacctg aggtcttggt cctcctcctg ttttccctgg   26520
tttggtaaat agcatcacag tccagccagg tgtgcactct ggggacctga gtgtcatcaa   26580
tgtgatcctc tctccctcat cattcctaac ccaagagtca cctaaatctg tttgttctat   26640
atccacagtg gctctcacaa tgcttccctc cttctcttct cactcagacc cctctaatcc   26700
aggccatcat ggcatgggag gagacatgct gatcttgcct tctccaagcc atcctgcaga   26760
ctgctctaga gttctctttc taagtgcagg tctgaacttg tcactgcctg cctaaacctc   26820
tgagagttcc tattatgcag aaattgatct gttattctgc tgtgaacttt taattcacta   26880
ctaaatagcg tgagctaata catataaagt gcctaactca acatctaagg agatgctcaa   26940
aaaatgtcat ttatgctatt atcactgaag gctccttcaa gccttgcaaa gttgatatgt   27000
```

-continued

```
agatgttcat agactcaaac tgtaaatgtg actcatttat ttcacattcc acatgctgca   27060
taaagtcttc atacaggcac agaaccgata tctttatcga tttgaattct actagtaaat   27120
taaaagttca cagaaagata ataaatttaa aaaacaaaca tgtagcgact ggtcaatgtt   27180
cccttggctt catagactat ggatactaat cattacagat acttaagata taggctgggt   27240
gccctgggtc atgcctataa tcccagcact ttgggaggct gaggctggtg gatcatgagg   27300
tcaggagttc gagaccagcc tggccaacat ggtgaaatcc cgtctctact aaaatacaaa   27360
aaattagcca ggtgtggtgg cacatgcctg tagtcccagc tactcaggag actgaggtag   27420
gggaatcgct tgaaccaggg aggcagaggt tgcagtgagc caaaaaaaaa aaaaaaaaa   27480 aagatataca gatcatggcc aggtgcggtg gctcatgcct gtaatcccag cactttggga   27540
ggccaaggca ggcagatcac ctaagattgg gagttcgaga ccagcctggc caacatggag   27600
aaaccccgtc tctactaaaa atacaaaact agctgggcgt ggtggcgcat gcctgtaatc   27660
ccagctactt gggaggctga ggcaggagaa tcgcttgaac ccggaaggtg gaggttgctg   27720
acctaggcaa caggagcaaa acttcgtctc aaaaaaaaaa aaaatacag attattttac   27780 aattccactg aattgcaggg gaattataag gtagctgagg tgtacctagc tagccttcca   27840
cctcatcttt tggctttctc tcagctcctt ccacaacagc tcagccctcc tccttggcat   27900
atacacatta gttgaacaga tttctgggca cctgccttgt gtcaggcacc atgctgggca   27960
gtgggaatac ggcaggtgac ataaggtgag atcatcctaa gtcaagtagg gctgaggact   28020
ggggaagggg tgggatggga ttttagatgc aggagtcaga gaagatttct ctagaaaagt   28080
aatatttaat caagacctga gtgctgagaa tgtgccaact aggggaagtc tgaggaaaga   28140
gcattccaga ctgagggagc agcaagtgca aataccttga gggaagctgc ttagcacttt   28200
gcctgaacca agagagctgg gtcgctggaa cctagtgaag gagggtagga gatgaggtaa   28260
gagaggtagg gtcttgcaga tcatgatatg aagttggcat cttattctgc ttagagtggg   28320
ggccactgga ggacctaact atcgaattac attttaaag aatatcctgg cttctctgtg   28380
gagtgtggag aggcaaggat ggaggcaggg aggagagtgc aaggcagggc ctgggtgaga   28440
gaaggtggag ctggaatggg agtgagtgtg gaaaggcagg tggtgagacc tggcagcatc   28500
ccacagtgac acattttgtt gccctgagtt tttcatgaac actcaatctg agaggaccca   28560
tttacaacta ggagcatatc tgtaaaaagt ggaatcataa gacaagtaca gtcccctaag   28620
taaggcacac agggtacatc tcacttgggg gcgtaccaca ggggacactc tctagcactc   28680
ctggcaggtg gatagttttg gttaatagcc cttttttatgc tcttaaaaat cataccacat   28740
aagcactgac ccttaaaaga tgactttgcc tgccagggat aagggagaat gctgctcact   28800
ttcgatacaa aactctcttc taggaggcca atgtgctcat tcacaaattt tccttgagat   28860
cttaaagatt tgatggactt cttttaaaaa gcagtgagca atatgctacc tactgtcaca   28920
atcagagcag acaaagacaa atgctttat gagtaattta attcctctcc ctgaggaaga   28980
catcctcagc tgtcagcacc atccccggtg acacgcaggc gatgtgaagt gactgttaaa   29040
agcagcagat ggtgcttctt acttcgtgtt tacggagcac ccatagggtg atagttgctt   29100
ccaatgccgc atacattaaa atatttcttc ttcttctttc ctttcccta ccttgtgggt   29160 ttcaggttct cttagtgctc gatgtgacaa ctccggacgg tgcagctgta aaccaggtgt   29220
gacaggagcg agatgcgacc gatgtctgcc aggcttccac atgctcacgg atgcggggtg   29280
cacccaagac cagagactgc tgtgagtatt tgcatcccac catggctgtc actaactcag   29340
```

```
tgatgacaat tatataaacc ttagcaaaca cttgtattta ctgagcccct accctgtgcc    29400
aaacactgct ttgagagtac atcatttggg ctatctactt taatcctcac aatacccta     29460 agaggttggg attatcatta tatgcatttc aaagataaaa aacttaaacc atatgaggtt    29520
aagttgcctg atgttaccgg tgaggctgga cctaatactt aagctcagag ttttgggtcc    29580
agagcctatg tccttttctc tggcaattgc ttccctctag atgaactgga agggaggcaa    29640
caagtccttc aagtaacctg ggacccattt tggccccagt gaatttgggt ggaactgttc    29700
tgcataatct tgatcccctt tagtttggaa tatcctgtat ccctgctcgg atatttttg     29760 gaagatgagc atgcattaaa tgtcacataa ccaatctgca gagatgcaga gctggcaagt    29820
gttgggatgg cttggcaggg gcttggcagt gaagcattgg gcattggcta gcaaggctcc    29880
cacagaggag gcgcgtccca ttgcccactt tgctggctcc ttgctgggac aggagctgcc    29940
ctccagccat actgcattgt cccagttgtc aaggtcccaa gttgtcatac tctcttggca    30000
tttgttctgg tccggccttc cctgacccct tcagatggtc ttcagagatc acccctgccc    30060
cactcctcct ttgtaacct  tttaaaacat aaccctctgt tagctccgcc tccccgcccc    30120
aattcagaat gagataaaac ttatcaaggt cctgcaaggt cctcctccct ctccaccctc    30180
agcctaggtg cctgcttggt ttctcgtcac tttcctccct gctccctgca ctccgcaggg    30240
aagccacaat agctttcctt cccttcttca aagagccaag tgcatgtggc cttggcacat    30300
cctggagagc tctgccttcc ccgaagccgt gcagcgcctc ctgctccatc cccaccccac    30360
tatctcctca cagaggcctt cctgcagcag tcccacccct ctgtgttctc actctgctgt    30420
ttcactccat atcttatttt ctattcatgt ttgtccattt ctcccactaa aatgtaagcc    30480
ccctgtgact ctgtcttgtt tgcttctgtg tccccatgcc tggagtggga agaggcacct    30540
tgaggatgtc cagtgcatct gcagctggcc ctgtgcctgc tgcccttgcg atccacacac    30600
ctgacctggc ataggactcc tatggaatgg ggactgttcc tatttctctt agcatccccg    30660
gttctgagca cccggtagat gctgaatacg tgtttgtcag atggtccaga taagcagtag    30720
agagggagct aagaaggaag gaggccgtga gaattcaaag ataaagattg gcaaagaaat    30780
tccagccata agcattgcta gacttggcat gtgactggat gaggaatgtg agggagaagg    30840
aggggtcaag ggtgctccag gtttgtgcag gatttgggtg ggatcatagg gcaggcagag    30900
gaggaacgga tcagtagaga agagacaata aacttggttt ttgagcaatg agataaaaca    30960
catgattgcg tgcaaagtgg gtgacagaag cagggatgga tgagataggg agattgtgcc    31020
agaattcagt gaaagctctg ataccttcat tgagaaaatc ttgccacaaa caaacaaaca    31080
aacaaacaaa caaacaaaag tctattaaac ccagcaatcc cagcaattcc actcctaggt    31140
atacacccaa gagaaatgag aaggtagata tctgcacaaa aacttgtaca cacacattca    31200
cagcaacatt actcataata gctgaaaagt gaaaacagta accaaaaaga atatatgtat    31260
tctgtcacca aaaagaattt atgtactgac acatactatg acatagatga acctcaaaag    31320
catcatgcta agtgaaagaa gccagtcacg aaagaccaca tatggtataa ttccattgat    31380
aggaaatgtc tagaataggc aagtctggag agacagaaag tagactggtg gctgccgagg    31440
gctggaggtg ggactggagg gaagagatgt ggcaggtgg  gggacacaac tgctaaaggg    31500
cacaggattt ctttccggaa tgatcaaaat gttctaaaat taatattgac ggtgatggct    31560
gtacaactct gagaatcagc taagaaccat tggattgtac atttttaaatg ggtgaattgc    31620 atggcatatg aattatatct caattgagga attaccaaca gaaagaactg aatggaataa    31680
aatagcaggt agatggaatt aatcatgata aaaagcagac atcatttaat taaacaatag    31740
```

```
ggaaacaaat gataattttt ttaaaaaatg taaactgagc caaacagtga accaaagtaa   31800
actaaacagt tgagtgatga acttggttta cattctggca caaacccctg ctctctttag   31860
gagtggcaga cagttctcgg cccagctgct acccaccaag tacactctga gcagcactgt   31920
gtaggcaagt gagtccttaa gtgtgtgaga gaggtccgca cgggcgagga tggctaggag   31980
aagcctcatc gaagaaggac tgcccagctt cgtgatgttt gctcatgagc agttgatttt   32040
tatgtgcata gttgtgaagc atttggaagc atgtccctaa ttttcttttt cttcttcccc   32100
agagactcca agtgtgactg tgacccagct ggcatcgcag ggccctgtga cgcgggccgc   32160
tgtgtctgca agccagctgt cactggagaa cgctgtgata ggtctgtgtg aaccgtggcc   32220
ctacaaacag cagagagagt cccttgccaa ctagcatgag aattaatcct ccgagtgtaa   32280
ttatggaaaa gggatacttg acaaacgttg atgaccttct tcctgctctc tgtcctcaaa   32340
aactaagctt ttacaacaac aacagcaaaa acacacacac acactgagca cccaaatctc   32400
actggactcc atactctgct ctgggcaccc tctctttatt ttgactttgg gagaggcaca   32460
ggaccccaga gattcctccc accagctggc tccaaatccc aggtgctctg tatgaggcag   32520
taatcaatag tgagatcctg ggacacaggc tggttgcagg aaaggcctgg cctaattaaa   32580
catgctgcga aaattcttgt aagagggcct atcacagcat atggccatat ataaccatcg   32640
tgtacagaag aggcactgcc ctggggatag gatggcagtt acatgcacac acatgaatgg   32700
gcatggggct gggaggaggt aagagccctt tgggccaagc cacactggag gaggtggagc   32760
agtgaggcac catccccca agctgccggt gcaggacgtg ccttaagtac aactgtgctc   32820
tggctttaaa ctcttccctc ccagaggctg ttgagcagag ggctgtgagg ctggcgtcag   32880
aagcaaaggc ttcctcctca tttccttaaa agtaagaaag cagttctttg gcaccctgcc   32940
agtcacttat acctgcacag aggaaatgtc aaatacactc ctagcttgtg ttttcagggg   33000
tttctggctg ctgaggtgaa ggcagggaca taaagtttaa gtgttaaaaa ggaagtcact   33060
tgttgaaagc ctttttaatt tcaaaataaa agacagaaat agaatgccac ataaaagaaa   33120
tgttatcacc accaatggta agaaatagac ctctgctaaa actgcgtccc agtgacaatg   33180
cccccctcct ccctagaagt gaccactatt ctgactttta tggtaatcgc tttctttctt   33240
tgcttcataa tttatgaccc cagtgtgttc ctaaacacaa tcatttagtt ttgcctaatt   33300
cccttccttt cccttctttt gtcttccctc cccactcctc ccctcccatc cttccttgtt   33360
tttttaagct cttttaatca gcaggtttct tctccataga aaccataata attcttttaa   33420
ctcttgctct tagagaaaaa acaaagcttg tttagttaca actgttctct gaagcacctg   33480
ctcttcacag ctaccctgct tttctgtgat actgtactca gaacattccc cccaacatgt   33540
ggtgcagtgg cttagactac atgatttgga gacagatgta catgaatttc aatcttgcct   33600
cagccatgta cctgctatat gtcaagagtt tcttaacctc ttggccttag tctcctcatc   33660
taagaaaatt ggaaatagca attcctcata gggttggagg gaggttaaat gagagaacac   33720
acacaaggtg cctggcacaa cataagtgct aaataaataa tcattgaaac tatcgttatt   33780
tcacattatt tcatgtggaa ggatgtagtt aacttgagca gaggacaaac aagtcctccc   33840
cagcttcccc tgccttcttc tctgtgactc cagcatcgag gatgcccctg ttagtcgtgg   33900
ttcttataga agccactgga gggattgagc tgggagcaga ggtggaatgc aagcttacac   33960
ctggcttttg gagagtgtct tagccatcct ttttctttgt catatcctca cctgcccttt   34020
tccccagtga gccagagccc aggtacaaga gtcagagatg gggatcaata cctaagtggt   34080
```

-continued

```
cttggggagg gggtcaatag agctgagtgg tgctgaggca ggagcctcac ctttcctggt   34140
ccccacctcc cagtctttgt caccattaaa cagtagctcc aggacagggc agcattgcat   34200
agccctgccc acacccattc tgctcatctg accaccactc aatttcctac caaggactgg   34260
ccgactactc agatgccaga ccaccaagac aaatgtggct ctgttctaca aaggaacaga   34320
aagtgaatgt ttcttatgcc gtctaattta gggggtcgt gattgtccat ctggtggtct    34380
gggggtgggg gtgatatgca aaatctggta tttccctcct ctgaaaatta ataggggccaa  34440 atggaagaga aggtagagag gctgactcat tcatcatatt ttttctatag aataaaaaat   34500
aacctataat atcctgattt ctacaatgcc actgcaggtg tcgatcaggt tactataatc   34560
tggatggggg gaaccctgag ggctgtaccc agtgtttctg ctatgggcat tcagccagct   34620
gccgcagctc tgcagaatac agtgtccata agatcacctc tacctttcat caaggtaaag   34680
ccttctattt tctaggtttt agttttttaa tgttgtacag ggctttgtgt ttagagacaa   34740
ccacctccgc attcacagga tggattctct ttagaaattc tcttatagta ttgaatgtac   34800
attattttgt cagggcactc aggcatatcc tgatgtcttg aaaaagtcat aggctgaaaa   34860
tagttcattc atactagtga atataactta aaagaataac taaaaaagag actagatttt   34920
tatttccctg aattttccat ccccatctat ttcaaaacca cgaaggaatc attcatttgg   34980
tttggagagt gtatgagtct tcctggaatt cacgttcact aataatgctg ttttcacata   35040
taataaatga gctgatttat gtgaaattag ttcccaagct acagaacact ataaaaatat   35100
tggaaactga tattatttca acattaagtc tgagtttccc tttgaaaaga ctggacccgg   35160
gccaagcgtg gtggctcaca cctgtaatcc cagcactttg ggaggccgag acaggtggat   35220
cacgaggtca ggagatcgag accatcctgg ctaacatggt gaaaccccgt ccctactaaa   35280
aatacaaaaa aattagccgg gcgtagtggt gggcacctgt agtcccagct actcgggagg   35340
ctgaggcagg agaatggcgt gaacccggga ggcggagctt gcagtgagcc gagatcgcgc   35400
cactgcactc cagcctgggt gacagagcga gactccgtct taaaaaaaaa acaaatgaaa   35460
aaaaaatgaa aagactggac cctctcactt cattaaggtg agagcttttt atataaatac   35520
aaaaaaatgc aaattacagg cagaagaaaa cctgctatct tatcacgagt cagactcaaa   35580
gatgagaaat catagcagct gcgggatggg agcaggtgaa gttgagagcc acatagagag   35640
atacatgcag aattttaagg accatttgca aatgtggaaa tattgagaaa accccacttt   35700
ctactcacca ctaggacttg tcggcaagca aatctttctt tgtttaactt aatagatgat   35760
gagggcttgt ccaatgcaga ctgattatgt ttgtgttcca gatgttgatg gctggaaggc   35820
tgtccaacga aatgggtctc ctgcaaagct ccaatggtca cagcgccatc aagatgtgtt   35880
tagctcagcc caacgactag accctgtcta ttttgtggct cctggtatgt gaggaataat   35940
gtctcctata gaggccagct tataggacta ggaagtcaag atagagaaat tgagttagaa   36000
attgtggaaa ccatataact ttgggttcag ggtagcagca tctccgggta gtgcaacccc   36060
agaagagaga tgggggctaa gcctgatttg agagtcacta aggaatggcc caacagagca   36120
gaatgtggtg tcccagaggt cagaccctgg ttgagctacc tcctttaatc aaatgggaag   36180
tttctacgtt taccaccaag gcaagaaacc aaggactgtg gccaaaccta tgggtctatt   36240
gagaagtagg tggaaagcaa aaacaaagca tttcttaaaa cttcaaatac ctgtaagtta   36300
aaaaaaaaaa aatcaatcag tggtacgtgc cttggtggaa aagcgctggc tagaattccg   36360
atcccagttc gtttccttag ctcatatgtg attcttgggc aagttgttct cttaacttct   36420
ctgaacttca gttttctcta ctgttaaatg ggaatactaa tgtctgcctc ccagaattat   36480
```

-continued

```
tgccagcaaa tgtgatgata tttgtgaagg cattctgtca actaaagcat tatgtaacaa   36540
gttgtgctat gctgataggc ctgggatttt tacaaaacag tctgtcataa gggccacatc   36600
atgaatcacc taatagatgg aattgtctta taacaaggcc ctcttatcat ttcagtaact   36660
aaccctcctt catagcccaa agtgtcatag ccatgtccag taccaggtcc tgactctcct   36720
agcaaggagt tttggggcag catgacacag gacttcaaca gaaattgccg acaccagtgc   36780
aaacttgcat gtgtttgcct ctccagtttc acaactgatc tcaatctttt aaaactctgt   36840
ttcacagcca aatttcttgg gaatcaacag gtgagctatg gtcaaagcct gtcctttgac   36900
taccgtgtgg acagaggagg cagacaccca tctgcccatg atgtgattct ggaaggtgct   36960
ggtctacgga tcacagctcc cttgatgcca cttggcaaga cactgccttg tgggctcacc   37020
aagacttaca cattcaggta aaaagagaga ccataagtag gtcaattaga gcaaactatg   37080
attgaagttc aagtttgttc tttattcatt caatcatcat tcatttgttc aacaagcctt   37140
tctgagcacc ttttacgtac catgaaggtt gctatgtgct gagaaaggac atgattcctt   37200
ccctcaagca gctgacaggc taatgggaga gaaaaatgaa tagataatta cagtgcagtt   37260
tgtcaaggga cagaaatagg caaggtggac acagaagttc tgagcacata aaggaggcat   37320
gactgaccca cactggaatg atgaaggaaa gcttcccagg accacatgac aaatgtgaaa   37380
ggcagccctc taaggaaaga gaagggagga aaggttaaca aggcagagga aatgcaatgc   37440
ttgaagaagg tttgtgcatt tagaaaattc caggtggttg agcacgagtg aagcatgaag   37500
tcggcgatag gagtgcagtg agaagtgagg taggagaaag aggtgggagt gactttatgg   37560
atggctttgt gtgtgtctac agggattgca cagtatcctg cagaataggg attctgcatg   37620
gtgtttgcag agaggttggg gaagggagct gtgcctacta agtgctcagt agtgcactgg   37680
aggctgggaa ataaagatgg aacatggtct ttgccttcca agagctcatg gtctagtaca   37740
atgtataaca tgtcaaaaag caagcataat acagtaggat aattgcttta ggggtggtgc   37800
atgttcatgg ggtcttggaa agtgcccgat tctgcctgga ggagtcaggg aaaccttcag   37860
gaggaggcaa tgtgtggtct aagaatggaa aggtccacag ggcttttcca gggagaaaag   37920
tcagagaagg gcaaccttca catgtgaata tatgtgggga tgcagaaagg cataatatag   37980
gggagaactg gcaagcaata tttatagctg gaatacagca tgcataagga agatgggtag   38040
atacatttgc aaaggttgga aaaggaccca tcatgttggg ccttgtgtgt catgtcaagg   38100
agcttagatc ttgtccatgc tggaaagacg atgcagagcc attgagagat tgttaagtca   38160
agaagtgtga tcgtcaggtg tgaaggctag gtgcaactac aggcaccata tagatgatag   38220
tttgggtcgg gtccttaact ggaccatcag aacacattca gagtggctca actgagagtg   38280
gttaggtgcc taacccaagg caggggtaat ggcaataggg aaaagaagac ccacagaaca   38340
caaacaaaga attgatcaaa tatccgagta tacgtgttct aatgatacac acacacac     38400 acacacacac acacacacac agctctcctg cctggaatac tcgttcccac cttccaggct   38460
ttgtgaactt actctttgag attcagctta catgttcttc ctttgtatta gccttctcag   38520
aatcccagct aaagttacag tcactttgtt tttccatggt actctgtgca tgcatctgtt   38580
atagcattca tggcattgta ttataactgt gtctacccac ctgactcccc tggctggatg   38640
tgatcatctc tccctgttgt ctttgtgtcc tccagcctga catagcttct agcccaaacc   38700
aagtgcacag tcaactttta tttaacaaat cagtgaatga aacgaaggtg ggtagggttg   38760
ttcctggatg agtaaaaaac aaaacaaaat ttagaagaac agcacagggg ctggtgatat   38820
```

-continued

```
gttacagtga gccaaaatga tgccaaatta aaaagtatta agtgtggaca atgtaaaagt   38880
ggaaactgat ttttgaaaaa agtaagtaaa atgtgctcag ataacaaata aatgattttt   38940
tttaaaaaaa atgaatagta gctcttgaga atcagaactt ctggaacgtg gagatgttcc   39000
taatactagc ttatgggtgg ccaagaatag aaagtggtgt ctgagaactt gcgatcatca   39060
tggtttcagg tgatgtcacc cctggatctg gacttcccac actgggatgc cctccatcac   39120
ttcctctggg gtttgtcctc cccatggagt gaggaaggtc caagtacatg cctatgaaaa   39180
ggtggctctc agtcctatgc ccccttctaa gcaggactgg gaaggggctt agctgttccc   39240
gtatcctcag gcataattta taacaggtag gtatgtggta agaatcggat tttaaagct    39300 tttgatttta aattatgcag gttaaatgag catccaagca ataattggag cccccagctg   39360
agttactttg agtatcgaag gttactgcgg aatctcacag ccctccgcat ccgagctaca   39420
tatggagaat acagtaagtg gctacgagaa attaatttct ttcttcttag gtgttagttt   39480
aatttgattc agctctctaa ggtggcggca gtctccaaac aagtagataa gttacttgat   39540
gatcctgact tagaatcact gattcaatct gaatttttat attctagaag ctttttttaga  39600 agaaatgttt ctctaaaaag atgtcagcac ccagcaccaa tgaagagtaa atgatgctgt   39660
cttgctaaaa gggccactga attttttatta aagatgatta agtgagaaag ataatctaca  39720
ataaatggac acatttcctt agctaggaaa tggcacctac aacacagtct tatttattcc   39780
ttgagcagct tttccttttg agattatact ccatgctagc ctgtctgagt catcatgtat   39840
tctattaatt cctttttttt tttttttga atttcacatg ttgggtcctc ctaatctcaa    39900
ctggaattat ttaacaagag ttccttaagc ttttctgcac tcactcacct aaaaaggaag   39960
cgtggctagc atgcaccatt tccatgtcac tgatgcagta aataaagtcg gaagcagaaa   40020
ggtgtaacaa tgtattgact cttactgtat gccagataga ttataatata tgaattatct   40080
aatttaattt tcacaacgga cataagagat aaataccacc gttacttctt gtctatagtt   40140
gatgaaacac agtcatggag aggctaagtg acttgcccaa tttacacagc tagtgagggt   40200
ggattcagaa tttaagccct gggtttctg accccagagc ctgtgtgctc agtcacagtg    40260
ggagactgcc atacctctct acatggcatg atatatgaac accacctgtc tttgttaggg   40320
agttaagaaa aataaaatcc caagagagat ctgacttgag atctttagac tgtaccactt    40380
gcaacttcta acctgttctc tcgattgcag gtactgggta cattgacaat gtgaccctga   40440
tttcagcccg ccctgtctct ggagccccag caccctgggt tgaacagtgt atatgtcctg   40500
ttgggtacaa ggggcaattc tgccaggatt gtgcttctgg ctacaagaga gattcagcga   40560 gactgggggcc ttttggcacc tgtattcctt gtaactgtca aggggggagg gcctgtgatc   40620
cagacacagg tgagtgaaat gacacctgga ccaggtggct ggggtgtcat gtggaagaga   40680
gagagctgtg taagaaagac catggctgaa ctcacatcag aggtgggaaa ggattaagga   40740
gagcagagct ggagtcaggg aagatggaca tggtgcctta ttacactcaa tcctcttcac   40800
tgtggaaatg ccacaaagtt gtgagaaagg tgccaggtta caggaaatgg tcgtcatggt   40860
tcagtgctgg gtagaagagt tggtgtcgag ttccaagaat tgtgtgggga gatcaaagac   40920
aagtccgggt ctaaatgaat gtgccgacaa atggtgtcag gccacagaga acatgggaa    40980 cagtgttaag ttatggatag taaaagaagt gagtgtctac tttgcatagg ggagtgaggg   41040
tgagattcag ggtcttggcc atgtttagat ttggttctat gggaggggtg aatgccagtg   41100
ctcaggcact ttggggaagg cttcagaaag gaaggctttg acattctaca ctctgaccca   41160
tgttgaagga aatgtattgt ctgaccctgc tcacttctct gcccctccac tcttctccta   41220
```

-continued

```
cccccaggag attgttattc aggggatgag aatcctgaca ttgagtgtgc tgactgccca   41280
attggtttct acaacgatcc gcacgacccc cgcagctgca agccatgtcc ctgtcataac   41340
gggttcagct gctcagtgat gccggagacg gaggaggtgg tgtgcaataa ctgccctccc   41400
ggggtcaccg gtaaggccat gggtctgctc tgccacctgc ctcttcctgt cctgatgcca   41460
tgaatgtgtg caaatagctt ccattccgag gaattcctag gaaattataa tgacttcggg   41520
ttcacccaaa tgtgctcact ctaaagataa tatcttaaag ataagatatt gcaatgccca   41580
agaggtgaag tggattaagc aagagcagag tgcaattatg ggagaaaaca cctaaagctg   41640
ttttgagagg tttgtcatta gaagatgaca ttttcagacc aagcacatgg tttgtttctt   41700
aatgaactaa gataacgagg gaaaacttag tgacttctta aatgtcacat ccttctgctg   41760
gtcaatctga aagaagaatg gattcttcag cagcagtttt gggggtattg ctcaaaacct   41820
tactacttct gtggagctgc ctgctttttc ccagccagct agttaagcct cctagtggcg   41880
ctactgtgtt ctgcaacctg cagtgggcat ggagagagag ggccagccct gccttgcatg   41940
cctgctcctg agggctttgt tctggggtcc ctagggaagc acatttctct ggctcttcta   42000
gagggtgact cgcaacttta ggcctctgcg tctggtcttc ctcctgatgg atgtcgacct   42060
aggcttggtc atttgttcct tcccaggtgc ccgctgtgag ctctgtgctg atggctactt   42120
tggggacccc tttggtgaac atggcccagt gaggccttgt cagccctgtc aatgcaacaa   42180
caatgtggac cccagtgcct ctgggaattg tgaccggctg acaggcaggt gtttgaagtg   42240
tatccacaac acagccggca tctactgcga ccagtgcaaa gcaggctact tcggggaccc   42300
attggctccc aacccagcag acaagtgtcg aggtaggact ccaccccagg caggctgtgt   42360
ctgtgcgtgc ctgtgtacgt atgcacttgc ttgccatcta agcagggaca atggcagttc   42420
atatcatgat gttactttga ttctctgacc aaactggcct gtgagcaccc tgggcctttc   42480
ttcctctgtc aaaggcctta agacaggttt accctgtagc caggctctgg aagacagagc   42540
tgggttaaag ctgggtggga gaagtgaaaa aggtcaggtt tacattccta cgcggaaaag   42600
gatgtaacac ggggccacat cctatgccca atcccaaggc agggaggcag ggaagtggct   42660
gccaaacctg ttgtaggaga gtaataaatg acttgagagt aagcctaagc aaactcaagt   42720 gggaaggggagtgggctgta aaatagttta agagactctc tcaggaagtc agcgtaattg   42780
atgtgtagaa aggtaacagt caacagttct cctaacaaga cagcttcaaa gcagcagcta   42840
tagtggagca ttcctgaggc ctgctgcaga tcaaagcatg aatgtgcaga ctggtcctct   42900
tgcccagcgt ttctttcaaa tctttgcaca tgttatattt tagaggcaag ttcagttcta   42960
gaggagctgg cctgccccac agactcaccc ctcagtccca ggctgacctt ggtgcccaga   43020
actcaggagt ttgtttaccc taactttgtt tataaagtcc agaatggggc cgggaatggt   43080
ggctcacacc tgcagtccca gcactttggg aagctgaggt gggtggatca cctgaggttg   43140
tgagttcaag accagcctgg ccaacatggt gaaaccccat ctctactaaa aatacaaata   43200
ttagctggac gtggtggtgg gtgcctgtaa tcccagctac tcaggaggcc gaggcacaag   43260
aatctcttga acccaggagg cagaggttgc agtgagccga gatcatgtca ctgcactcca   43320
gccgggcaac agcgcaagac tccatctcaa aaaaaaaaa aaaaaaagtc cagagccact   43380
ctggacaccc aggttggaag actcttggtt cctcatgaag acccagaggt ttgcatggag   43440
ctcacagcct cccactcaca ccagagtctc caccttgaag tgcttgagga cctctgcaac   43500
ctgaggcttc tacttagtgg tacaaatccc ttcaggaatt ctaggccaga ccagcccaga   43560
```

-continued

```
ccccaaactc tgggttagct gtgatatgct agaaagcacc ttatgagagg aaaagcccat  43620
atgacaccaa caggactgag ttcaagtcca gttttgtaac atacctatta tattatgcta  43680
attatgccaa ttaatccctc taagcctcag tttccttata tgtgtgatta atatttaact  43740
cgaagtggtg gatacaagaa agcacactat aaacactata attctagtta tatattctaa  43800
ctatattctg tctttagttt tagctgtaat tctaggttac taacagaaat ttcactggct  43860
ttacaccaca catttcttca ctcaaccatc ctttatcaag cacataccat gtacccagtg  43920
tggacctaga tactgaggcc ataatggtga ataagtcatc ccaactctcg aagagtccgt  43980
atgataataa ggaagataca caaatatgta tgcaaataat gataacacac ttagatacgt  44040
aatcagcgtt ttgtgagcac tgaagataga acaactcaga gaatcactgt aatcatcaga  44100
gaagtgtctc acccactatc atatccttaa ctcctataac agaacctggc ttaatcaatt  44160
tggttgaatg agtaaaggta ttgctttctt aactgtattt cctacaccaa aggccgcaga  44220
acagaggaaa gaacattggc tctgcctgac ctctcattgt agcttgccat ttacttgcca  44280
tgtaacctca ggcaaattag tcaacttccc tgagctcaca ttcctcatct gcaaaataga  44340
gggggatgtc tacatctggc acgtaatggg cccagaagaa atgttattca ccttgaaagc  44400
aaagccagag tgcttgcaga atatctaata ggctttagt ttaacagggg gaggaaaatg  44460
agtgctgcca gaaaggctgt aatctccctg catccacaca caccaggcaa acctgccaca  44520
tgattcctaa gacctatctg tattaagaag gtgcatggag gtataaaagg attctctgct  44580
gttggaggct tgatctcctt ccttgtatct ttgctctacc tccactttct agactagttt  44640
gatgtgaatg ctccatttgt cttttgtctc tagcttgcaa ctgtaacccc atgggctcag  44700
agcctgtagg atgtcgaagt gatggcacct gtgtttgcaa gccaggattt ggtggcccca  44760
actgtgagca tggagcattc agctgtccag cttgctataa tcaagtgaag attcaggtat  44820
gcattcttcc ccttaccacc cccaaccca cagaatcaaa tccttaagtg tccactgggt  44880
ggttctgtca cagatctagg acactcctag tctcctgagg atgggagtag tgattactat  44940
ttctgtcttt aaaaattgct gcattaaaaa aattctgtat aatgataata cttcaggttt  45000
atgtctttat atataccatt ttcaaaacct cttttgcaga tactgtttca tttggtactc  45060
atgataactt agttgagttg aaaggaaaag tattctgacc tcagttttca ctggtcaaat  45120
aaagtctcaa aatacttgaa atttttcaaa gtgatatggg taggtggaac tgggaatccc  45180
acccatgtcc cctaacttag ttcagggctc ttcccactat aatatttcac tttccagctc  45240
gatttctttt caacagatgt ctttgtaaaa caaatgaaga aaaacataaa cataaaagat  45300
atcaggagtc cagaaagtat caaggcttca tctctactag aaatacaaaa attaggcggg  45360
gcgtggtagc tcacgcctgt aattccagca ctttgggaga ctgaggtggg cagatcacga  45420
ggccaggagt tcaagaccag cctggccaac atagtaaaac cccgtttcta ctaaaaatac  45480
aaaaattagt ctggcgtggt ggtgcacacc tgtagtcaca gctactcagg aggctgaggc  45540
aagagaatag ctttaacctg ggaggcggag gttgcagtga gcggagatcg cgccactgta  45600
ctccagcctg ggcaacagag caagactctg tctcaaaaca aaacaaaaca aaaagaaaag  45660
caggctctta agcttcataa ataaacaaac ataccccaa acccacctgt cgcacagaat  45720
acaacatatt aaacagatca ggaaattttc tgagaaatcc aggaaatttt ctgagaaatc  45780
cagggtcttt gtatggtgac ttaaattgct ttcaaaagga aaagagagac aagaaacaga  45840
ttggttccta agatgatatc accaagtcag tgtgcacaca agcaatctga aatgttactg  45900
caaaggttat attcacttgc ctcagtttaa ctaggaagat aaatgcgtac tgaaaaaagg  45960
```

```
acacggggc  cgggcacaat  cgctcacgcc  tgtaatccca  gcatttgggg  aggctgaggc   46020
aggtggatca  cctgaggtca  ggagttcaag  accaccctga  ccaacatggt  aaaaccccat   46080
ccctactaaa  aatacaaaaa  ttgggccggg  tgcagcggct  cacacctgta  atcccagcac   46140
tttgggaggc  caaggcggga  ggatcacgag  gtcaggagtt  tgagaccagc  ttggccaaca   46200
tagtgaaacc  ccatctctac  taaaaataca  aaaattagcc  aggcgtggtg  gcgcatgctg   46260
tagtcctagc  tactcggggg  gctgaggcaa  gagaatcatt  tgaacccggg  aggcggaggt   46320
tgcagtgagc  caggatcacc  ccactgcact  ccagcccaga  caacgaagca  agactccatc   46380
taaaaaaaaa  aaaaatacaa  aaatacaaaa  attagctggg  ctaattttgg  tggtggcagg   46440
tgcctataag  cccagctact  caggaggctg  aggcaggaga  aatgcttgaa  cctgggaggc   46500
agaggttgca  gtgagcccag  atcacatcac  tgcactccag  cctggacaac  agagcgagac   46560
tccatctcaa  aaaaaaaaa  aaaatggggg  cggcgagggt  atgggtatga  attagaatta   46620
gattcaaatc  ccagatttgc  tattatcaaa  ttaactactc  caaacccatg  tcttggaatg   46680
aggataaaaa  taaccatcac  attcaattgt  catgagattt  ggtgaatata  tgtaaatcat   46740
ctactttatg  gcaagtaatc  agcaaatggc  tctaagtcta  ggaatcttat  ttcatacaag   46800
agaaagttcc  agttgacaag  ctcttctcca  aataggcgtt  ttgtttgctt  tttaaacaag   46860
gtcttgcttc  tgtagcccag  gctggggtgc  agtggcacga  tcatggctca  ctgcagcctt   46920
gacctctagg  acccaagcaa  ccctcctact  tcagcctccc  aagtagctga  gactacaggt   46980
gtgcaccacc  acacatttga  caaaaaggca  tttgacaaaa  agaaaatgat  cactgattcc   47040
tcaaattgtg  actggctatc  atgagagatt  aaaatgtcac  tgatcttttt  ccttttttgat   47100 attttgacta  taaaattgta  aatttaccat  gacagaaact  taaataaact  tctgagtatc   47160
accagtcagc  aaattaaggt  gtgaaacact  agctaattat  actctataat  gtgttagagt   47220
tactcaagca  atgtttttagt  ttgactgtag  gaagacaata  tagtgcaaca  gagacatgga   47280
ctctggttaa  cgttctgcta  gttactcagt  ctcttttgaa  gcctcaataa  cccatatgta   47340
agattaaggc  cctaaaaagg  taaaattcta  caattctaat  caactatctc  tttctacaaa   47400
acagaagttg  tatgtgtctc  tcatgatttg  ccaaccactt  tatctcttgc  ttttcatagc   47460
atcctaccca  acagtgtata  ctccatccac  actgaagtac  atcgtggctc  ccagaattca   47520
acacgctctt  tggcctcaat  tcctttacac  atgctatttt  ctccacctga  gcccaccttt   47580
actcaccact  gacataagga  ctcaagtcag  gtctcctcta  atttccccct  cccttttcctg   47640 caaacactca  agtctgagtt  aggcactaca  acaacatgg  ctgaaactat  agttttcag    47700 ggacctatga  ggaagaaaaa  gactggtttc  aaaatccaaa  acacaaacac  atctgcaaat   47760
ttgaaattca  aatgttttaa  ttaaatatga  gataacgtta  tttcacttag  tcaattgcaa   47820
ttcaagtctt  atatagtttt  aaacatgaga  tacagtgaca  cagggcttgt  aggactaaga   47880
aagccaaagg  tcaaaatagg  tcttgaaatt  gctctgacga  attctgtgtg  actcttctat   47940
gctcccacag  gttcctgtgc  tttacacacc  acaaccatat  catgatcagg  accactagaa   48000
cctgaattca  gagaacccaa  ggtttcagag  aagtctgttt  ttccaggatc  cccaagaaaa   48060
agttaaaaat  ctttacccag  gttttctatt  gatatacaac  agtcattcac  tggtctttcc   48120
tagaccaatc  ccctctagtc  agctgtatca  gtttcccatc  taccttgtct  cccgtgatca   48180
tgatttggca  cccaataaaa  ctcttgacta  gatcagtcaa  atctagtctc  aaccccaaag   48240
ataaccccag  ccctgggcct  gagacatgtc  ccaggaaagg  cagctcaata  aatgtttgaa   48300
```

```
gaactgtttc tttcaccaga agacaataat ggtaagctac aatgccacta caatgaattt   48360
cttgccaaaa taacaaattt caagagaaca atttcactat tctcaacttt taaagcctag   48420
ataagcactg tccaatagaa atttctacaa tgacgaaaat gtcatatatc tacactgtcc   48480
aatacagttg ccactagcta catgtggcca atgagtactt ggaatgtgac tggcgtgaat   48540
gaggaactga attttttaact ttactcttaa tttaaatggc cgtatgaggc tggtggctat   48600
gaaacagtga aaacatagtt gtcgtccctc tttgtaaatt tgtcacacca catgttttgg   48660
atatacatgc ttaaaaaaat aaaatatgga aatgtttagg ccagtattat ttactagcca   48720
atttatagct gtgtcagctg ttataagaat aggtccatca gcctgcaaat gcagtcactt   48780
actccttcaa atattaagta tctacccata ctgtaacagg ccagaggcct cgaaggtaga   48840
gatatgaata agactgacta cagagaatta atagtctcta ggagtacaga gcagacaaaa   48900
ataactgtag agcctgacaa tgcaaatgca cttaatgcca ctaagttgta cacttcaaat   48960
ggttaaaatg gtaaatttta tgctacgtat attttaccac aatttttaaa aagattaaag   49020
cctactgaag aaaaaagttg aaacaatatt ttcgaaaaaa ttaacactat gggacagatg   49080
gacatgatac actgggaagc agtgcagagt agaaagagca taaattttta tttcagaata   49140
ggtttgagtc ctggcaccat tacttactaa ttgtgttagc ttaggaaatg acttcaccct   49200
ctgggccaat ttcctcatct gtcgattatg agtactcaat gatatgatgc actgaggtca   49260
gtgaaagtgc tcggtagcca tgatcgatat caggagaag agaagcagca atcatggagc   49320
caggagcaca gagaggagac aggcattcac caggcaaaca gggctatttg agaaacatat   49380
ttagaggaag cagcatgtga aagcactaaa tagagagaaa aaacagaatg ttacttggta   49440
atttgacttg attggaatct cagcagggcc ttatcataaa gaccttcaac tgtcatacat   49500
gaagagtttt tggtttttat cctataggca acagtgactg aaaatatatg tacacctagg   49560
aagtttgtca gtaacagccc aactctcatt acttcaatac aggggctcta aaatttcaac   49620
cagaaaacca aaagcacaag gagttttaaa aaaataaaag aggccgggca cggtggctca   49680
cgcctctaat cccagcactt tggaaggccg aggtgggcag atcacctgag gttaggagtt   49740
tgagaccagc ctggcaagat ggagaaaccc cgtctctact aaaaatacaa aattagccgg   49800
gtgtggtggc gcatgcctgt aatcccagct actcgagagg ctgaggcagg agaattgctt   49860
gaaccaggag gcagaggttg tggtgagccg agatcgcacc actgcactcc agcctgggca   49920
ggaagagcga aacttcgtct caaaaaataa aaataaaaat aaaaaataaa agagcagctg   49980
ggcactgtgg ctcacgcctg taatcccagc attttgggag gctgaggtgg gcggatcacg   50040
aggtcaggag atggagacca tcctggctaa cacggtgaaa ccccgtctct agtaaaaaca   50100
caaaaaatta gccaggcatg gtggtacgcg cctgtagtcc cagctactca agaggctgag   50160
gcaggagaat cacgtgaacc cgggaagtag aggttgcagt gagccgagat ggtgccactg   50220
cactccagcc tggatgacag agcgagactc tgtctcaaaa ataaaaaata aattaaaaat   50280
agaaataaaa gagctttgtt gaggcagcca aaacacacat ggctagccat ccatagacct   50340
cctttagatt ctagaaactt cccttttggg gggcccttcc tccactctat cttctagtct   50400
ccttttggta caatgaatgg ctttggcatg aggctgagaa ggaatgcagc tttattttgg   50460
tggtgggaag taacaaacat gaactacaca gcctgcctta cagccatatc tgcagcctgc   50520
aagcagctcc agacctaggc agatacagga acactttct tggattggct gattaaattc   50580
acacctgcct cttgcttttc tatccagtga gtgggatgcc acttgggcca ttagcttttg   50640
tttctcacag gcagcttgac aaaccatact taaagaataa cagaaaatgc ttttgaatgc   50700
```

```
agaaacatag caccacaagt ccatatagca aaagctatct ggtagagctt taagtagtag   50760
ctcttttctc cacctacaaa tgtcatggtc acatttttaa aagtgcaaca aaaacaatac   50820
ccttttccta atgtaatttt cttaaacatg aaatcttagg gggatactat gcccatgtat   50880
ttgctcagct taaatgcagt acacgagtgt ctatatttct atggaaacat taataacttc   50940
catctgatca acctacatca cctttcatat agttttttccg gcttctagct ttgcaattac   51000
agccttgaaa ccagactgaa ggcagaaaag ccagcccaag attatgacat ttcaatttta   51060
aaacattttt aaaaaataaa gacagtacac agctttcaag gctgtagcta tagaatcaaa   51120
aggtgaaaac ggtttaggaa ggcaattcag tctgatgagt cagaggtcat tagtgtttct   51180
atggaattac agcacaggca tttctcagaa aactgcacgt actgatgatt ctctggcatt   51240
tttcatttgc aattttttggt tctctggagg aacaaaaggg actgttgata atccttcatt   51300
tgtcttggag gttaagaaat ttcaaggcca ggcacagtgg ctcacgcctg taatctcaga   51360
actctgggag gccaaggcag gaggatccct tgagctcagg aattgaaaac cagcctgggc   51420
aatatagtga gacctctaca acaacaacaa aaatatgtct gtctttttca attagctggg   51480
cgtggtggca tgcacctata gtcccagcta cttgggaggc tgaggtggga ggaccacttg   51540
agcctgggag gttgaggccg cagtgagcca ggatcactgc actccagcct gagtgacaga   51600
gcaagacctt gtctcaaaca aaaaaagaaa agaaagaaa tttcaaaatg caaaatactt   51660
aatacagaaa aatataagaa aatgtataca ataatctgtc agttgccatt tattgaatct   51720
attactataa accaggcatc agcttgacac tttacatgaa ttcttactga aaaatagcta   51780
ctattgtctc cattttatag atctaaacag atcattgtac tccattacat ggaaagagcc   51840 acaaagtca aaacaagaga acttctattg aaagcatctt gactaataaa accctacctt   51900
tgcgcagtgc atgttctgca acagccggat ggatgggaac ttagcataat ctcaaagagc   51960
aaccctgatg ctcccataac agcaggacct caacgtccaa gaagaatacc acaccttact   52020
tgagcccatt tacaagtcac ctcctgaaaa atccaagatg cctgtcagaa gcagctactg   52080
agggaagtga agatgttttt atttgttcat tgtcattgtg aagactgact aaagtcttac   52140
tgatcaagga gtttgtttga acatggtcag agagctttca aagtcatttc agaaagtgcc   52200
ccacaccatc ctcaacagat ggtttgatgg aagagaagta gccagctctg ctcaggaaat   52260
ccattagtaa ggtgcagata ccaccaaaga gatgtcccac atgtggcaga atgtacctt   52320 ttccttattt tctttaaaat ctccatataa aaagggaaga tggatgcatg agggcctaga   52380
aaatgtttat ccctctggat caatcttagg aatctatcct aagaatcaga aatacagaaa   52440
atagtacaaa actcgaggcc atctaaaaat tcaaacacag gaaaatgatt aaattatgta   52500
cacttattca atggaatatt ttgcgaacac tataaatgtt ttccaagagt ttacaaaggg   52560
caaataccat attaaaaata caatgtaaaa ctgtattctt ggaatgagct caggtatatt   52620
ccaatacata tatacatgaa aaaaaaaaca ctttggtcca ttttctctta gtgattatct   52680
cttagtataa ctaattttttc ttcctccatt ctacttttct gattaaaata tattgttttt   52740
ataaacagaa acatacatta aaaaaatcct ggcagggcac agcggctcac gcctgtaatc   52800
ccagcacttt gggaggctga ggcgggcaga tcacctgagg tcgggagttt gagaccagcc   52860
tgcccaacat ggacaaaccc cgtctttact aaaaatacaa aattagccgg gcatggtggc   52920
gcatgcctgt agtcccagct acttgggagg ctgaggcagg agaatcgctt gaacccggga   52980
ggcagaggtt gcagtgagcc aagatcgtgc catggcactc cagcctgggc aacaagagtg   53040
```

-continued

```
aaactctgtc ttaaaaaaaa aaaaaaaaaa tcctaagaac aggccgggtg cggtggctca   53100
catctgtaat cctagctttg ggaggctaag gcgggcagat cacctgaagt caggagttca   53160
agatcagcct ggccaacaca ggaaactcca tctctactaa aaaatacaaa aaattgccag   53220
gcatggtggt gcatgcctgt gcaattctcc ctgcctactc aagaggctga ggcagggaga   53280
actgcttgaa tccgggaggc agaggttgca gtaagccaag atcgcgccac tgcactccag   53340
cctgggcgac agagccagac tctgtctcaa aaaaaaaaaa aaaaaaaaaa tcctaaaaac   53400
aaaatgattt ggctaaactg tctacaatca acagcttcaa ctgaagggga aaaaaaaaac   53460
taccattctc taaatgactt ttaaattact atcttattag aaacacaatt ctgggcacta   53520
atctttctta catactagtc atgaatgctt aaagctcagt actatctccc acgtcccagc   53580
ttcagaaatc cattgtgtgg caacaaagaa atacatcttt aacctttcat cccaggatct   53640
ttcaaatctg aagcaaagct agttaatcat acctatgaat aattctgtgc caggcacagt   53700
ggctcacacc tgtaatccca gcactttggg aggcccaggt aggtggatca cctgaggtca   53760
ggagttcaag accagcctgg tcaccacggt gaaacccccat ctctactaaa aatacaaaac   53820
ttagctgggc atggtggtgg gcacctataa tcccagctac ctggtaggct gagacaggag   53880
aatcacttga acccgggagg caaaggttgc agtgagccaa gattgcctac tgcactccag   53940
cctgggcaac agagcgagac tccgtctaaa aaaggaaaa agaaaaaaaa acaataattc   54000
caaaagaaat ttttaaaaac tattcaaacc tggtgagtta agacagaaga gcaacaacca   54060
agtatttata gcacaacata aatacaaaag atactctaca aaataggact aagggagaaa   54120
aaactccttt tttttagatg ctaaactttc ctatattcta aaatcaaatt caacaaatat   54180
ttacctagtg tttttccatgt ataggctgct atcccagact gcattggaaa aataggtgag   54240
taaagctggc taccccctaga ttcttaaaat ctagcataga aaatagaaaa ctgactggat   54300
acaaggactt ttgaagtaaa tgccctaatg gagacattaa cagcagtggt cacactattt   54360
atttcttctt agggaaaact agaaaaaagt taatgacaaa atggcacttg aatcagacta   54420
gtaagggagg aaagaaagaa tgtaaataca gacacattat caataatact cagccataca   54480
tatcttttgg atgtccttcc actgctggca actatttccc ctagaagcag tcacatcctt   54540
acagatgatt atacagacct tgtctgactt tttttttttt tttttttttga gacagagttt   54600 cacttagtca cctaggctac agtgcaatgg cataattatg gctcactgca gcctcgacct   54660
cccaggctca agggatcaac ccaacccgcc tcagcctctc gagtagctgg gactacaatc   54720
atgtgccacc acgtccagcc tgacatgttc tttactaaat gtcctcacag gcaagaaagg   54780
cctatcccag cacacacaca accttctcat cctaggttgg atggtctcat ccacatacac   54840
tttcacttac acttcccaac tgatgattcc cctctcccec aaactttcaa ttctggatga   54900
gactcttctc ctgaaccaca gacccatcta tccaaatgtc tattgtcaat gtctaccagg   54960
ataaataacc cataggctcc atcaatttca acatgtcaaa ctgaacctat tattttctct   55020
ttgaatcctc tttctcctgt gttcttcact caggttccag gtaccaccaa ctctcatccc   55080
ccaagccaga gatccccaaa gactcctcct gggctcccac tttaccaccc ttcccaacag   55140
tcccctcgaa taatatagtc aatcaccagg acattttcat tctctctcaa atatccctag   55200
atcaagctca aggcatctaa tcaccctata atcctagact attatgactg ctcctctctc   55260
ttcctggaat ttaatttcct aatccactca aaaatcctgt ttgattcccc ttttcaactt   55320
tttagcatac attaatagca ccaaattaca gaaataaaca aatccaacaa ttgaaaagct   55380 acttttttgca accttatttc ctcgaaacac cccaaagctt gaaaaggata acacctaaat   55440
```

-continued

```
tcctatttgc aaactctctt tatacagaga tgcaaatata ccaactttga tgttaaagca   55500
agtttctaat attaagatat caataaagtg atatactagg caagatgcct tgcttcagta   55560
ttaataagcc atttgtataa ggctaagtga tctactccct ctgtacttag attttctcct   55620
cagtgaaaga tcaattttct tagcatcatt tttcagctct aaagtccatg agtttatcaa   55680
aagttgcagt tgtgtataat aggggggtaca aatcatacaa tgctaacact tgaggaaccc   55740
ttaaggggtt atcaagattc ttagattttt taaaaaaaac tagaaggata aactataaat   55800
cattcctaat ctcttccatc ccactgtagc ccccatttta cagaaaggag aaattgttta   55860
aagggaataa catttgtagg attcctgtga tttaaacact aattgtggtc ccataggcat   55920
ttccccgatc taaaaatggg aacaaaagaa cttaacttaa gccgggcgca gtggctcaag   55980
cctgtaatcc cagcactttg ggaggccgag gcaggcagat cacgaggtca ggagatcgag   56040
accatcctgg ctaacacggt gaaaccccgt ctctattaaa aatacaaaaa aaaaaattag   56100
ccaggcgcgg tggcaggcgc ctgtagtccc agctattcgg gaggctgagg caggagaatg   56160
gcatgaaccc gggaggtgga gcttgcagtg agctgagatc gcgccactgc actctagcct   56220
gggcgacaga gcgagactct gtctcaaaaa aaaaaaaaa agaacttaac agggctgttg   56280
taagtattaa atgaaataaa tataagtact caaaacagta cctagcatat agcaaatgtt   56340
cagtaagagt tacctattat tggccaggtg cggtggctca cgcctgtaac cccagcactt   56400
tgggaggcca aggcgggcgg atcacctgaa gtagggagtt tgagaccagc ctgaccaaca   56460
tggagaaact ccatctctac taaaaataca aaattagccg agtgtagtgg cgcatgtctg   56520
taatcccagc tactaaggag gccgaggcag gagaatcact tgaacccgag aggcggaggt   56580
tgcagtgagc caaaatcgca ccattgcact ccaacctggg caacaagagt gaaactccat   56640
ttcaaaaaaa aaaaaaaaga gttacccatt attataattg gaaaccctcc aaaacacaaa   56700
tataaacaga ctcagaaaag acttcttaat ttaaaaaatc taaaccactt tgcagcagct   56760
ttagggaaag tgttccattc tgcacacact tagggaatag gacctttac taagtcatca    56820 cccagtgcta ttactgagag gtcagcttct tcatgaggtt gcagtattca tgtgaaaatt   56880
gacctttggg tcaaccattc agatctcaga tcacccaatc aataaaataa atacggtatt   56940
ttttttttaa gagacaggtc tcgctatgtt gcccaggctg tagtgcagtg gccattcaca   57000
ggaacaatca taatgcactc cagcctcgaa cttctgactc aagcaatcct cctgcctcag   57060 ccttccagt agctggaact atagatgcac accatcacac cagcttgtta aagcactaca    57120
gatactagta taccctgccc cgctaaaatc acactcttac ataacgcatg tttctttaca   57180
gtttttgata cctattataa gttccacagg cttagaagtt cctcttctag cattaacata   57240
cattagcaca aacataaggt tagaattgca tccctacttc cccacagctc aactggactt   57300
ccagagtaag agatgattat ttggtataca gctgttctga gtttaacaat cttctctctg   57360
aatatgcctc acattcctga ataagtcaca gtgaccatac tattcaaaaa gtaaatacta   57420
aggatatcaa atgagaagaa cgtatttgta aggtcagcaa ggcaaacttt aatacaagct   57480
gacctggaaa ttgagactgt atagacacat tggttacttt cagtccctac catgttaagg   57540
ctctcatgtt tctagtttat attattcact cttcatcttg tatcaaatag tatttaagag   57600
cctaatgcta ttttgctttg tttcctaaaa ggcattaagg atcaaaagtc tctcccattc   57660
cacatggagt tctgcttcca tgtcacatgc ccagggccag catttttaag caagggtctc   57720
tttgcttcct tgtctcccca ttggcaagga tttgtcctaa acctcacaac agcatctttc   57780
```

-continued

```
tccaacatca caaattggct ttggactttg ctcttctcct tagaaataca taaaggcatc   57840
tttaaaaaat aaataaatag gccaggcgcg gtggctcacg cctgtaatcc cagccctttg   57900
ggaggccgag gcaggcggat cacgaggtca ggagaacgag accagcctgg ccaatatggt   57960 gaaacccecgt ctctactaaa aatacaaaaa attagccggg cgtggtggtg ggcgcctgta   58020
gtcccagcta ctcgggaggc tgaggcagga gaatggcgtg aacccaggag gcggaggttg   58080
cagtgagcca agatcgcgcc actgcactcc agcctgggtg acagagcgaa actccgtctc   58140
aaaaaaataa ataaataaat aaataaaaat catgaccagt taaggaaaaa aaaagtcaag   58200
atttttaaac aagcaatttt caaagaccat acttgtctcc acggctaaaa ttgaagtctg   58260
gctttaattc ttgcatctac cattaaaaca cagtctccta aatactagac tccttaaggt   58320
acaaatggcc ctttgtatcc tctaccagaa gctagtgctc agattccaag agtgtaagcc   58380
ctggatcaga cacatttggg tctgagtccc atctctccca cttagggggc caagtcactt   58440
aagttgttcc tcccatctgc aaaatgaaaa taatgttact ctccttataa ggttgctgca   58500
tgtaattatc acacagtggg cacacaataa atttcagctc aagaaaaaag gaaaggcaaa   58560
ccattaacga caaaattttc agagaaagac actagtcaca cccaagtact aattaggcta   58620
atactgcaca tcaatataat tgttaaatca caactcagcg aagaaatcag ttgagaccaa   58680
aactttctaa caagaacata aacagttcaa catatcctct aagaacgaga gaaaaattaa   58740
gtttttgtgt gtgtgattta caatttaaat ggtaaaaatt cttctagata gagcacatat   58800
gagcttgaca ataacattcg aaactcctgg ctggaagtcc tccttacttc attacttcat   58860
accaaggcat gctgacaaac ctccttaccc tgagctaagc tctggattga daccctggaa   58920
tcaaagtgtc accgagcaag aattatatat tctagcttat acccaagtat cagaaaaatt   58980
ttactaaaat atcaattaaa ccaagtgggg tgtgccatac actacatgag tctggtgcct   59040
gggattaaaa atctattaga aacgggtttc acaagatgat ttatcaagaa tccacagtaa   59100
atgttcagag atatggctag catagacaaa gtacaataaa ttagaaatag gaaaattacc   59160
ataactggaa tttctttaaa aaatcctcaa tttctttcaa agtacaaagt gtttccatga   59220 agaatttttaa ggatgctatt taaaataatt cggaactgaa tttttttctt ttagtaacta   59280
gtggaacaaa ctttttaaac aacaggatta caaaattcct cctttttgtat ttgaagaagc   59340 tattgtcaca atacaaaatt aaataaaaca gaagggcagg atggctcacg cctataatcc   59400
caacactttg ggagcccggg gtgggcggat cacttggtca ggagctcaag accagcctgg   59460
ccaaaatggt gaaaccctgt ctctactaaa aatacaaaaa ttagctgtgc atggtggcat   59520
gcacctgtaa tcctggctac tcgggctcct gaagcatgag aatggcttaa acccaggagg   59580
cagaggttac aatgagccaa gatcacgcca ctgcactcca gcctgggcaa cagagcaaga   59640
ctctgtctca aacaaacaaa aaaattaaat aagaaaaaat gacaataggt ttttttctta   59700
ttcaaaaagt tttaaagata aaatcaaatt aaaattaaac aatcaatttt tttaaaagga   59760 taaaatttttt aaaaatcaaa ttataatcta ggcttcaatt atggtaaagt tacatcagct   59820
acctattgtt tccaatagaa cacaataaaa tggtaattaa acataattat taatataaat   59880
tacaaaacta caacacgcaa taaaagtcaa agaaattgtc ctttaatgca cttgagataa   59940
catctgtttc aaaaactgct ggcaatatct tttctcaagc tcacttttcc aacattatct   60000
aatgaggagg caagggaatg tttatgatgt ctttacagtt atttcaataa atcatttatg   60060
taggggtaca agtacctaca aaattactat atattttaca cccaacttct gaaattcact   60120
aagcactaag aaacacaatg ttttaagaaa gacctaagtt tttaaagatg aaatcctatc   60180
```

-continued

```
tcacagcagt taaattaaaa aaaaaaaaag atcagaaaaa cacatctaaa aatctctaca   60240
ctactctgga gttagctgaa ttctcttaga ggatgaggaa gaaaagagga gaggcaggga   60300
cagggaggca agaggaagga tgaaaggaga gaaagaaaag taaggagggg gtacctaggc   60360
agtaaggcct gtgggactgg ttcaacttcg aacaaatttc ctcttcccta agactcagtt   60420
tactcatttg taaaatgtac acaccatcac ctatgtcagt gtttcccaaa gcaaggaaac   60480
cactggatga ttttaaatgg tacaaagaga aggcatcata aaacattcca aagctgttag   60540
taccttttcc actctctttc aatccttctg attacatcag aagaaaaatg tggtgttagt   60600
ttttctagtg cctctctagt gcttactaat ctctctatca aaggcctggt cagagacctt   60660
ggcagacaat agcatttaga atttaacaca attctatttt cattaaattt ttttcattgt   60720
tactttctac ttgtggcaaa taattttca tttaagctaa taaaaaaatt cattttaaaa   60780
taaatgttgg gttgcagaat gttaactatt caatatttaa aaaattaaat aagcaatata   60840
ttagaaaatg acaaaaatca tgtggtgata caggaaaaac tgaagattta aaaatactgg   60900
tttagcagag tagtggttag tagaaggtta ttttcaactc taagcctcag tttactcatc   60960
tataataagg gaatatcacc acctatccaa agaaaagtta tggaaaggat tacatgagtt   61020
agtttagctc tgtgcctagt gctgagtgtt caacaactac ttgttccctt cccttttaag   61080
gatattacca gaaaaccttt ttagagacct ccagagagag actttgggta ggggatgggg   61140
atgctgggct tcctgtatat cagagacagg agcatttgct ctggttctaa tacttcccac   61200
taagaacctc cagggaccta gccttgcttt taccctgata aagctgcagt ctactctcct   61260
aaggctcata attctactta caagcaagac tgggaataaa gtgctacaga aaaggggcac   61320
atatcttaaa tcactgagaa gtcaaaccct aaagggcacc aaggaaggaa ggaccatttt   61380
ataacaagtc caagccaaaa taaagtattt catttgggca aattcaacaa ctctgtaatg   61440
gaaaagaaag tcactaggtg gttcataacc agcctttatc acctgatatt gtcaaactag   61500
agcccacagg ggagaaaaac cttgggagga ggagttccaa ctcagagtag gaatgcttca   61560
agaaaaggaa caccaactga gtacttacta cagtcccacc attgtgagta ataggcactt   61620
tattttacat atattgccaa attttccaa acctatatga gataattcca agtcaactga   61680
ccaaattgcc aaatctccaa atagccaatt ctctaaattt gtcaaaaatt tgttttaaat   61740
atttggacag tttataaaaa ttcatattga tgagacagtt aattaccttt taaggatttc   61800
tgccaagtca gaactgaccg ttggaatacc agcatttta agatgttcaa tttgtctcta   61860
cactgcagct ggagagagct gaagcagaga ggacctctgc tggtagaaat atacatcctt   61920
gtctgggctg cagggcatgg gggagaaatg atgtatagga aacgggaaaa acaaaaagga   61980 aaaaatggt ggggagcatt taagaaaaac gagatgaaca acgggttctg taaggtctac   62040
agattagatt cagcaaactg tcttttattg aatggaatac tgggtaaact gaacatctgg   62100
gaaactggtt ttcaatgact tggattgtgg taaactggtc tgctgtacct atgagatcga   62160
tgatattaac attacttaca gataaggaaa ttaactcaga aacttttgta aagtaataca   62220
gctacattcc aggttttcca taaactacct catttcattc tccaataatc aatgtggtga   62280
ttccacatcc ttttaccacc ctccacccag tatctccacc ccccttccac tcaactgtca   62340
aaaaaataca ttaaaaaatc acaagaatag acaggattta aacccaagtc taacgttaaa   62400
gctcaggctc taatgcacct agttatcact acatcctacc aatttgctga aataattttt   62460
aacccctgcc ctcccactgc tgaagtttgt ctaccattac tacagtaact cctttctgca   62520
```

-continued

```
aagatctgct tttcagaggt tgagtcacat taccgtggaa atatttcagg caaaagagta   62580
tttcagagat ctcattttat ttaccctgaa caaccttatt gctcacacga tttcagatca   62640
aatcagaact gaaattgctt gagaacttcc attagagact ctcagactgg caatccctgc   62700
tgtgtattaa caactttttc cgttcattat gttggcttca ttcacaagca cactggcatg   62760
taatttcatt attgtgatct aagagtgact aggttagtct cattaaataa atgtaaaaac   62820
taaaataatc ctaaaatctg caagatctat gtaacacctt accgcttgct caaactatct   62880
gctttactgc tggactcttc agggatttat cacatttatg atgctggaag acatgtctta   62940
tctgacctac tgacacataa aacctaactt ttcttatagc aacaatgtca aggtcctttc   63000
tatcaataag atagtacttc aaggctctct aaacagctgc gaatatattc tacccttttg   63060
gtaagcagaa aagttcttta ttcatagaac ttaagatgtg gctcacatat aaagcatttt   63120
taaaacatta atatttttac ttttacactg actgagtata atcagaaact ttcactaaga   63180
aaattcccac tgtgtaaaat attttaagaa tcaattaaac tgttactttt aaaaaagtgt   63240
taaatatttg ttctgattcc ccactgggtt caaaaacctc tttgatgtta agatggggaa   63300
aagatagatc ttttcagcaa atctgaatag cacaaaatga cactttgaaa aatgccaccc   63360
tctcttaaat cttttcaagt acatatttta aatgatcaac aaatagatga caaacttaat   63420
tatttttgta gcccatatta ggcttccctt tgcactttag tagtacctct tattaattat   63480
ttctgatctt caatgtacac ccaaggctac gcttaatgtt ttagcaaata gaataccatt   63540
cttttgaaat tgacaaaagc tataaattta actcaagaca gcttttgtag ttcagttaga   63600
ttcaaggtca tctcaaggct tttaattact aaccaggaat tgaggaggtt tgtacccgct   63660
atagttgaga gaaagagcag ctggcttatt cattttctta ttaaagagca ttataaaacc   63720
tatcttggca aattacaagt ttctgatcac cagtggtgag cacaaagcag caaagcaaat   63780
gatcttcaaa tgttcatgtt tactttcaat caacataaac tttaacaatg tctaaagact   63840
acttaatttt aatttcagca aatatgactt atgctttaat aaaaaaatgt atagatagct   63900
ggattcccaa aatgttccta tttccattct gaaatcagac ctgttaaaaa ctgtgaatgc   63960
ccttcaaatt agcataagat ttatttagat tctttcacca tcaaacactg cacaggatca   64020
ggatagaaac tagccactga ggaacccatg cagatttcta aaggaatgca agtttaaatt   64080
ctctctgcat gtacttaatt tctattcaca ctcaggtata ggtaggtctc aagacacatt   64140
aaagactgtg ggagatgata taattgtatt agaagacaca cgcacatcaa cttatcatcc   64200
cgagattttt agaggcaacc agagaaggct ctagggtgtc tctgccaccc attcacccat   64260
atctataaga attcgaaggt agcctcagaa gggtccttaa gcacagctct gaccagactg   64320
gagatgctag gatgagggtg cagggcaaca ttctagtgcc agaatcaaaa agaaaaaaaa   64380
agggcgggta ggggggaat gactctctct caccccaaaa tgataaaaag caaagagcct   64440
acccacagta tctcaaattc tatctcaagc accaggcatt tattaaaata aataagtact   64500
gctggcagcc ctggatgttg gtatgcaagg tatctcagtg taaattaaag tagttgttgg   64560
tgagggtaca ttgagataga cacacacttc tcaaaattat cccccaaaat aagccaagat   64620
aaaagcaagc acaagatggt gtgagaagta ctattataac actgaaaaaa taaaacctat   64680
ctaaatggcc agcaatgaaa aacaatgggc tgtcatacag ctatcgaaag tttcaaataa   64740
cttgatgttc aatgagtgaa gtttataaca ggagaaaaaa catttaaaat taaacaaaaa   64800
gcagaaaacg taatagtata tactgtatga ctaaaaaaat gcaaaaaaaa aaaaaaaacc   64860
ttggatttga ggtctagaag aaaatgttaa tgaaagttgc ttagtggtag gattataggt   64920
```

-continued

```
tattttccct tcgttttcca tattctcttc agtaaccatg cattaatttt aaaaacactg  64980
gattcttaag cagctcacat cttaagaacc aaaggaccta agggccacag gcaattcaag  65040
cacagacaga ccctcagaaa tcacaagtat ttaaaaccta aatatacgat gcagctgtat  65100
ctttcctgct tttatttata tgcaagcact tccaactgtg tttcccaggg tatgttcctt  65160
agacaacgct ttaaccctgc tttccaaaca aggcatttga aacatcgggt attctccagc  65220
caggagtcct tatctatgct ctgaaactag ctttggagaa taaatttaca gtgtttcaca  65280
cacttcggct tgctcagtat ttatttttg atgggcacac tgtacgaaaa gcaaacttat  65340
tttgaaatat tttgaaaagg ctcgcagcag ataggaaatt ttatctccaa atgttaaatg  65400
cacttcttca cagcagtact ttcagcaact gcttgcagtc agttctgaat tccagggaac  65460
caaagtatct ctcagattcg atctgtcacc aagaaaggga atattttttt gtgggaaagc  65520
aattgtattt tcccacatta ggtgattgat taagttctct ccctaaaagg ctgattggtt  65580
tcctggtgcc agtaaaatga ttgatgaata tttcaactgc agctaccctg ctacactctt  65640 cacttcacc ctcccccatg cacctctccc ctttcctgct gggttcccctt tttacagacc  65700 agcagcattt aaggaagttt cccttctgtt ttgcaatttc ccttaatgaa tcaacgttct  65760
caaatgaagc gcatttaatc ttaggaagac agcactcttc tcaatgctga atgagttttg  65820
cagataaata tcccattaca aggaatgagg aaaaactcta aaattaacta tgagtttgac  65880
tcagcaaatg aaactgtact caaaaaagag aaagtgtggc atggaggggt tataaatgaa  65940
aaaagtgatc ttgtttaaac aacaaaaata ctccataatt tatttcaaat ttacattaca  66000
aattatcata acatcagaac tgtaactgta aacatttcta taaggcagac tcaaagaatg  66060
aaatttacag ataaattatg ggatctcaca gactttaaag cagccaaggg ttctaaagca  66120
gaacagggaa acagtttggt aaatgtaaat attctcagag ggatgattga acagtatctg  66180
acatcaaaat catcccagag aatgtgggca gtcagtacca cagctatttg ctttaggcag  66240
aacttttcta aattgcaact tcctgttttg cccaattcat tccatcataa acctggaaaa  66300
tcctttcagg gattatctaa tttagctcct ccatttttat aggtggaccc acagagacat  66360
gcatttgaga cagagctaga atcagatcct aggcataaag tatctcctgg gcctcataac  66420
tcctcaatgt ttgggctcct ctctaaagtc ttttcctatt caaactactt tgctaacata  66480
atctattaac ccacactgcc tatcctcttt tacatctttc tcactatctc tcttttcatt  66540
aggaaatcac cttctgtatt ttataaattt tggacaccta gctcttatat ttcttttgtg  66600
agacagaatt ttaaaaaggt acatgggaca aaggccacct tttcctaaac tgcattcccg  66660
aatacagtca agcaaacagc cactagttta ttggccatct cgtcttaatc tgggatatct  66720
agtcacttta aattacagga gaaccatgtt tccaaacaga aactacattc tagttccagg  66780
agggcctatc aaaccttgga tttagcttaa acacactgct tgacttagat attggcccca  66840
atttcctcaa gtagctgaaa agcacattcc tttcccttat attttgtaga cttactctga  66900
ctaccagcaa gggactctga gataagcaaa aggctcatat tcctgacttg cctctttcat  66960
tcattcaata ttcatggaac accaattctc agtgcttagg atacagataa aagacattgt  67020
actcctgcct tgagtaactc aaaacgcctt cattccttag caccccttgg gttcaccgaa  67080
gattgtccct gatttggcaa aattgttttc tggccaaagg cttattaaaa ccaacatgag  67140 gccagggggct gtggctcaca gttgttaatc ccagcacttt gggaggccaa ggcgggtgga  67200
tcatgagatc aggagttcga gaccagcctg gccaacacag tgacaccctg tctctactaa  67260
```

-continued

```
aaatacaaaa attagctggg tgcgatggtg ggcacctata atcccagcta ctcaggaggc   67320
tgaggcagaa aaattgcttg aacccaggag gtagaggttg cactgagcca agatcgcacc   67380
actgcactcc aacctgggtg acagagctag actccatctc aaaaaaaaaa aaaaacaacc   67440
accatgaggt gggatgccga ggcaggcaga tcacctgaga tcacaagttc gagaccagcc   67500
tggccaacat ggtgaaatct cgtctctact aaaaacacaa aaattagtca ggcatggtgg   67560
cgggcacctg taatcccagc tgctccaggg gctgaagcag gagaatcact taaaccaggg   67620
aggcggaggc tgcagtgagc caagatctcg ccactgcact ccagcctggg agacagagtg   67680
agactccaac taaaaaaaaa taaataaata aaaataaaaa taaaataaaa gccagcatga   67740
gagaaaagaa aaaagtcact tgcaattcta agagtgggtc tttttggctc tctaatcaat   67800
aaaagttgaa ttctgggcct ctccaacata gataaatgcc ccagattctc aggttttttgc   67860 ttttaggcag atactatgct tggcaattta cagaccttgt ctctaatcct tataacccta   67920
cagtcaattt cagaaatgtc agagtatatt ggagaagagg ggatgttaaa tctatgaaac   67980
aaattattaa tgctgttact agctgcgaaa tctggaggtt taaactctgt gggtctcagt   68040
tttctcctgt aagatgggga taacagaaca cctacctcag agttaagacg ataaatatac   68100
ataaggtgtt tagattataa acactatgta aatgttagct attaatgtta aatgagaaca   68160
ctaaagttca gagaagtcaa gtgacaaagt cgcatagctg tgatctttgt taggccacac   68220
tccagagtcc ctgctctttg cctcacacca tctaaccaaa atccttcctc cctggatggg   68280
actactattg ccatttccaa aaaacaaagc cctctaaatg catgtcaatg gggggcttcc   68340
cccaggtggt ttattatcct gctaaaaagg catcttgggg gaaggattcc aagaatagag   68400
agaggaagtc tcctgacagg ttagacttca agggtacaga aagaatatgg aagaaaaaag   68460
ccaaatctgt ctcagttatt aggtttcgta attaaagcaa tttaactcaa ctgaagaatg   68520
caattgaaga tttcacatga atcttcaaat ccaaacatta agaaataaaa gaaaggcttg   68580
tattttctta taactaagct gcaatccccca caaaacacaa aaatgttttc aaaggtacat   68640
tacatgaaac tccaagaata tcaagataat tagagctctt aggaaggaag cccaaataat   68700
tatctcactg atctttcaac acctatccaa gcttcacctt gagttctgat gcggtaactc   68760
cttatttgtt attcacattg ttatgtgaca tttcttcagc cagcaagccc actacaggat   68820
gagttctacc tagtaactac cctaaggagt aaatttctaa ctctttaaca acacagtaat   68880
tgacttacac taaaatgtta ctcacactag gaaaggatat tcttcgacca gaggaagaga   68940
tgcctctcct atacagactt tattaccatc tcagtgaaaa ccaggttaaa agcaaaccaa   69000
tttacaaaac tgcattaccg aaatcacaac tctaagactc agtgaagcca aacatgtcta   69060
aggaaagcaa ataagcaaac tattcttgat ggaagtttta aaaagcacga taggatcttt   69120
atctcttata aattgttcat tattctatag caatgactct taagaaattc tgttgtcaga   69180
tttatttcca caaatgtaag tctacccttg gtgaggcaac tggttctctt gaaaaactgc   69240
tgccacaaga caattatcag ttaagcaaca ggtttcatgt agcaggtaac aaaagcttta   69300
tcagagaact cagtgagagt gcactaccac acatttcatg tattcccaag caaagaaaac   69360
ttaaaatgat atgaactcat tttcaataaa agtagctcaa ttatcgaggg aagtaagaaa   69420
actccaaagt aaaaaaagta ctactaatgg tatctggtga agtcaccatc ttctttacac   69480
atttcgttag ttcatttaga cctggagttc tcatatattt atgcctgagt gttcttcagg   69540
atccctttta cactcttaaa aattatgaag gaccctaaag ggttgatatt tatgtggctt   69600
tgtctattga tatttatcat actggaaaat aaacctatga aaaatttaaa atatttgata   69660
```

-continued

```
atccatttaa atttaataaa ttcacgttag tacaaataac atttttatga aaaataaaat  69720
tgtccaataa aacataaaaa ttagaagagt ggcattgttt tacattttgc taatctcctt  69780
aatatctggc ttaatcctag cagctagatc tcctatctgt ttacccattc agtatattgt  69840
gattttttgt tgttgttgaa gcacaggcag aaaatctggc cccacagatt tataatcgga  69900
aaaggaagaa gtatttgctt tttaaagtaa ttgtggatag tcttctttga tactacacca  69960
aaactcaatt aagtggtact ttcttaaagg ttagttcagt gtgagtttaa aaccatatca  70020
atgaactatg tgtaatccgt tacattaaaa tccattgatc aatctggcat tttgaacaga  70080
tctcttagct gtgtaggatc ctgtaatatc acacatagat cttttggaaa atactgaatt  70140
actgagatat tcagattttc aaaatgttga cacatttcat aacatcgaaa atcatattta  70200
tttcatcatc catctcatca gaagacatta atcattggga agctgtcaag ctcttagtgg  70260
caagtacaag ttttccaaaa ctaattgttg cttgaaagct caaattttat ttactggcaa  70320
ccaatactgt cagttttcct tgatatgaca gactcactgt tcgtttaaga aaaaaatagt  70380
ctgccaaatg cccaaggctg aatcaagtat agtttaatta tttcaagtat tccatgaaca  70440
aaagtagctg gctcagatca caacataatc acacaagcac tttgtcttaa aacaaccatt  70500
ttagtttgca ccagaagtgc ttggcatgta cttttccatt ttgtcacaca gaatatcaaa  70560
agtacatgta ctcaagggtc aagatttaat catcatttt actgcttcat caaggatgac  70620
attaagtgga aaagtctttt tgaaaaatac aagtgcatgg aagtgaagaa tataatgact  70680
actaatacag tttgtgcctt gatttctggt aagggaccaa cagtttttac tcactattgt  70740
ttctgcaaaa tcagtgtaaa tgtcaataca gtaaaaaagg caaatgatgt cttagcatta  70800
cgattaaaat atatttaaga acatcctgaa agggtctcaa ggaccccag aggtttgcag  70860 accacacttt gaaaatcact ggtttggatg caaccataaa taaatttaag gactcaataa  70920
atgggaagag attaagtttg aaacaaacaa tagtaatgaa tggtcaaaga atgacagaaa  70980
atacaattga gtactacttc attatttgtt tataaatttt aaaaagcaag ggatgaggaa  71040
gggggataaa gtacataagg ctacacagaa gtgttctgtc ttctagcttt tctttcgtga  71100
cagaaagact aaattagata aactggaatt agccataata aaaagaacat tgcatctgat  71160
ccagtggagc ataaggaatt aaaagactga atttttaatt cttccaaggt gatacagctt  71220
catacagctt catgattgaa atggggactt gaattaataa aactagtttt aaaaatgaaa  71280
actgccaggc gcggtggctc atgtctgtaa tcccagtact ttgggagact gaggcacgtg  71340
gatcacttga ggtcaggagt tcgaaaccag cctggccaac atggtgaaac cctgtctcta  71400
ctaaaaacac aaaaattagc tgggcatggt ggtggatgcc tgtaatccca gctactcagg  71460
aggctgaggc aggagaatcg cttgaaccca ggaagctgag gttgcagtga gcagagatcg  71520
caccgctgca ctccagcctg ggcaacagag tgagactcca tcacaaaaaa aaaaaaaaga  71580
aaagaaaaaa ctatctggtt aagctattcc cttcactgat tcagtctatg cttcattttg  71640
cggtagattt gttactaaaa tgtttcctga gctctaaact atgggattac acctgaagga  71700
aacatcatag ataaaatatc acaggaaatc taatcaatca tctctttttt tcatcagtgt  71760
tttagaagaa aatagagaat acagaaattt gggcattaca atgatgggtt ggaagagcaa  71820
gcagaaccca ctcttagacc tccaaaatgc tcttatacac agatctaaaa atccatgatt  71880
ctatgaaatg taaggaggaa ctggaaataa aaagctggga agattatcca tcttttttcac  71940 atgaagaatt tagttgtgca tttctctctc aaaatatgaa tcttgagtat atttttaatg  72000
```

-continued

```
agttataaat tgtttacaat gcaaatagtt gttcaagcaa atatctgtta gatacattct   72060
ctgctaataa taccactaca attccaatgt gctatagcta ttactctaac aactccctta   72120
atcactatta ccaaattttt aaaataattt ctcacttggg cagtgagtgc aaagtcacta   72180
ttctgggtca aaccacccac agagtatatc ttcaaatcaa atgcctggat ttgtttccct   72240
gaatacatta catgttgctg cccagggaat tggttttaga aacattacac ctgccagctg   72300
acttatcagc agggcccata gaactgacac caacttaaag gcaagaatca gtccagaaac   72360
agaaaaatat actgctactg ccatctgtgg tttatgcttg aatagcttct ctggtgtaaa   72420
caaattgaag ggtgtagagt ttacaattag aatccaaagg cctcatcatt taaagacact   72480
tttttaaagt taattcttaa tgtaacgaat tgtatggttt atttagtata agacgtaaga   72540
atccgtgatt ctgtatttga gattatataa tgctgatgga gaaaccacaa actaccctga   72600
atgaaaacta ctccattgca taactttatt tgtcccaaac acacactcct taaagaaact   72660
cagaacactt gaagccctcc tgtgaattta taattagaat catttctctt ttgaaatcgt   72720
gactgtcaat attaaaacag cccccgaaat ttttaaagca aaaaattttt aggaaatcca   72780
ggaattttct atttagacgt aagaatttgg ccagtttgct tctgtcaaga taaaaatttg   72840
ggagttcaat tattcctata attttttttaa gaacaaaaat tccaaaatgc aaatgaagtt   72900
tcaaagtagg ctattttcac aacgtatttt ctctcagttt gctttctcaa atgacaacca   72960
ctgtagcttg gggatcaaaa gatttggtgc agctgggggt ggggaaaaaa gcaattcagc   73020
tccccagcag ccggctgagg aaatcctggt ccgctcccaa actaaatcac tgttaattag   73080
aattaccggg ttacactagt aaagtcttat ttaaataact gtaaccactg aaaaaactct   73140
gggttttttt gagaagcttt tctacaaagg ctgctgttta atagcaggta acaaagaatg   73200
aagaacgaaa taccgtagga aatgttttat tctttcaaat gatgctctcc tcttttttcct   73260 gtggctattt ctccgccata ctgaaaaaca ggttagacat ctcacagtgg ttttcttctg   73320
attttctatt acttactaag ggtgttacag tctaacaccc ttgtcttttt cttaaagaca   73380
agccatgttg gaaaacaatc aatgaacaaa agactgggct ggattctaga aatactgtat   73440
atcaaagtta catctagaga cgtttttttaa atttaagctc agctgaatct gaaacttaag   73500
ctctaaaaag ctcaataccc aagaaagaat tacctgctca gtaccaaacc actttcttgc   73560
tcatttttaa taattctggt atttctgaac cctagttatc gaaggcatcc ataaaccctt   73620
aagaaattac ctgagccagg aaaaaacttt aattaaaaag ttaaggttga tcttaatgca   73680
gaagtgtgaa aaacattttc cttcacaact taattggttt tggaaatgct ctcaaagtat   73740
tacaaagagt tgggtatatc agatcactac ttatgtgggc agattagata gctaccttct   73800
gttaaaaact gtttcaagca catttattct ttattgaaat acaagcgtgt ttatctgttg   73860
attcagaact ttgatttttc taattctgac cttttttccca catgactaga atctgttttt   73920
acacatgaaa taaggcactt ttactgtcct acttaaaaaa aacagactga cccaacaatg   73980
taaaatttac tctaaaacac atcttctcaa gtgtcacttt caacttaatt attatgcatg   74040
gaaaaatact gaacagaaaa gtgtcattaa tttggctata aatcaaaaat aaacttaaga   74100
agcaaagatt atgaccagcc ccaaagatct cgatgaattt gctgacaatg aagtctccta   74160
atgtgggaga atctatcctg gctttatgca attcttaagc tagaagttgc catctgaaca   74220
caattcatta acaaaccaat ttttcaacat aaccaataaa taatatctac ccaattataa   74280
aaatgaagtg gtaaatcttc ccactaacac aaatgaaaca cagctccaag ctccaaaaca   74340
tgcaagcatc attagcaatt taaagccaac ttgcacaaca aacactaggg gtggtataag   74400
```

```
aaacttcctc taccaatgtt acagcaacag ttggcatttc tacctaccat cctctactat   74460
tctaaaatgt ggtattttaa tctaaactct attttccacc tttgccccaa aaccctagga   74520
aaaaagtagg gaatgagaaa ccagaaaatt ctaaataaaa tatggaaatg catgatttgg   74580
acatattttt ggaaatttac cagcagttat tttttttcatt agctccccat ccaactccct   74640
ttcatgtact aacacatgtg ccttgcatac accttttttgc tacggaagtc agaatgaatt   74700
atagattagg aatcatgtca tcatattttg gttacatgaa tcagaactgc tgaatgattt   74760
ggtggcttgt acactggaga ctgtaaatgt ggtcatctcc cacctcagct atgcaaaatc   74820
accagtgaat ttgctcactg tcgcctttct tctaccctag ccgtctttgg aggtcacaga   74880
agctacaaaa aaagaaaaaa aaaaaaaaaa gaaaaacctg cgtgctgtat gtactaagaa   74940
acaacagtac tacagcatgt ttttggtttt gtttttttct aatgggagta ggaaaaaatt   75000
ctggggcaac tcagaattaa cttaattttt taaatcacag aactgaaaag ttaaatcatc   75060
atgggaaata tttgccaatt tattttccag cataaacatt tggacggcat ggttatagca   75120
gaagaaaaag gcaccgtgct attcagtgaa cttctcccca tttcctctaa agtgtaatta   75180
cataaaatat gctttttaatt acttataatg gcttataacc ttcctttgcc ttcctttgct   75240 ttaaatatttt aaaagtatat tccctcattc tcttaaaatg aacaaatgca atattcagca   75300
tacacttcct caaatcattc atcttccttt gaaatcccaa aagggagcag tcctctatta   75360 caactaaaatg agttcatgtt tgttatgaaa acctacaagc aacaactgaa aatagcgcag   75420
tcagcacagg gaattcctgg aaggatgatg gtgcatcaaa aggctagaaa gaaactctgt   75480
tctgacagaa taaaaaccat tcaaaggact gtaaattcag catcaatggt gtttccggta   75540
ggaaaacatt tctaaaatgc cacctccagt ttatttcttc atgacagaga ccaaaagacc   75600
ccctatctgt atagttgtct cttgaaaata gttcatataa aatagaaatc agtcactagg   75660
agtaaaaaac agataattca tttcttttct actcagaaca agcagtttca tatatttttg   75720
gagaaaaata ttaattagga agcaaaaaag aaaaaatgtg cccattgttc cataggcaaa   75780
cttaaaaaaa tttttggcaa ttcttctgtg agcatgttaa cttcataagt gctaatgaac   75840
ataaattgta aaacattgca caatgctagt ttttacactg aaaaatatcc cacaacggtc   75900
tagcgtctag tgtattttaa gcccatcaag ctgccaaaag ttcccattgt attttcagca   75960
aaaagaaaac atctgtacca ctaacttaga ctaatgtaaa gctttaaagc caccttagtc   76020
taaatggatt gctcgataac attctttcaa atggttctga ccaattgagg aaatgagact   76080
atgaatggga aatctgatta agagttaaaa ttaccattga gttctttaaa atgtactaat   76140
gaataattaa taacaaatgc agttcttagg tttctcttac aacactatta ttctcaagta   76200
gaattgaaag caatattgca gtaaatattg aattgcagta aaatccgtca tctacattat   76260
atgcacaggt gggtacagga agtattcaca cataggaagg catcacagaa atatacacgc   76320
taatatggga tataagatag gttggggttt ggattcaaaa aaatcagcat gggaaaattt   76380
agatcaggat ttacaacact cacaaattaa taccaaacca aatctccaca caaactagct   76440
taaaaagtca aaggcattaa agaaatcctt tgttcctatt atactgtctc cttctaccct   76500
aactggattc cagcttcccc ctttgtgaca cggaatttta ttgatctcaa acatgttcac   76560
attcagaaat tagttgccaa cgacagccca cggaacggcc agccacctag ccatcataca   76620
tcatacacaa attaaaaaaa aaaaaaaaag agctctgaaa acacatcatt atttttaaga   76680
tcagcaacat caagtgaagt taaccaagct ctcttctaca cggactttttc cctttttgtaa   76740
```

-continued

```
aaaacaccag atctcctgaa ctaacaaaat gtttgactag ttaataaacg tatgaaggca   76800
cggatccaac ccaagatttc caccgtctgt agctactcac tcattcaaca attgagcgcc   76860
taactgacct attttcaggt tactttcctc acacctgcca ggtcactgtc ctgattgaga   76920
aacctcttgg tgaagcagtt aatttttagt gcctcctaac tgtcccgggt gtttgcattc   76980
aatttgaaat ctgttacttg ttagacactg ttcggtccta gatctctcag agaactgcga   77040
gtttatggcg cagcgagggg aggaggcact gatctctgag agcctccctt tattcggaaa   77100
tgaggagatg tgaaggtgg aaaacagggc aaataaataa atcgggtttg ccgccggagc   77160
gtttgccggc cggtgcgagc acccttgta atgcaggcct cccggggcga tcgcctgcgc   77220
taattgctcc agggcgcttt ccaagttcaa aagttcacct tttacgacct cacaaaagct   77280
cctaacacgt taccaataaa aacattccgc ggcaaacacc gaggaggaaa atatcaaaca   77340
gatacaaata aaacaccccg cagggggagg gagcgaaggg gaggagggcg aggaagcccc   77400
gaggaacctg aggacccggc ccgggcgagg gggcgaggga cgagcggtag gaagggccgg   77460
gccaggtgag ggattctcag ctcccaaggt cccggatcgg gacaagaaag aggagaactg   77520
agactaagag gtgggaccg ggacctgccg ggcagaagcc gggaggaggc aggtgtccgg   77580
ggccccgggg cgggctggag ccctcggcca gggaaagccg ttgcctggcg gagaggggag   77640
ctgagcaggg gcggagaccg gccagagcgc gcggggcgtt gaggaaggtg aggcgcaggg   77700
gaagcaggag gcgcgaaggg gtccgaaaaa ggaaacgact gggggatgtc tagcgaacgg   77760
gggttcggca gaggtggggg gctcgtagta ttcaaggaag aacgctcgag gctgcagaag   77820
aggaaaacgc tctagaaagc tgagcggtac aagggtgctg tggagtcggg tcaacagggc   77880
aagaagggag cgtcctcggt gggaggagga acccctgtag gggaaaagag aggctctgcg   77940
ttaagggaac ccgagtgagg ggatgccccc actgacggac cgcggtgggg acttccaacc   78000
tgaggagccc gggggggaggg gaaggttcgg tgctgggaag acaggggag gggacccggg   78060 gggaggaggg aggattggtg ctgaggggac ggggggaggg gaagcctgtg cagaggggac   78120
ggggggaggg ggaaatgaag ctcggtgccc agggacccgg gcaggggag ggtccgcgca   78180 gaagggaaca gggacgaagg aggaggatcc accctgagcg agaccgggga ggagagggag   78240
ggtccgcgcc aacggggaac ggggtgaagg gccaccctaa ggggccgcgg ggccgctgcg   78300
gcttcccagg gcgagggtcg gcagagagga gggggatccc tggcggaggc tcaggaagcc   78360
ggttcctgcc tggcccgggc gtcgcaggcc cctcacccac cgttgcgcgg cggcggaggg   78420
agcgcggcgg gaggctccag gaaccccgcc gagccccgc cgcctccccc tccgctaggc   78480
ggcggttcgt cccgctccat gcggtggtgc ctagggtccg cgccgggttt gttgctccgc   78540
catgaccggc gccctagtcg ccgtggtcgt cgtccgccga ggggaggagg ttgtcaggag   78600
cccgcgagct cccggccgcg gctctctctg ggccccgagc cgcccggctc cgcgccgctc   78660
cgcgcccctc cgcgccgc                                                78678
```

```
<210> SEQ ID NO 2
<211> LENGTH: 2544
<212> TYPE: DNA
<213> ORGANISM: Homo sapiens

<400> SEQUENCE: 2
```

```
atgcctgcgc tctggctggg ctgctgcctc tgcttctcgc tcctcctgcc cgcagcccgg    60
gccacctcca ggagggaagt ctgtgattgc aatgggaagt ccaggcagtg tatctttgat   120
cgggaacttc acagacaaac tggtaatgga ttccgctgcc tcaactgcaa tgacaacact   180
```

-continued

```
gatggcattc actgcgagaa gtgcaagaat ggctttttacc ggcacagaga aagggaccgc      240
tgtttgccct gcaattgtaa ctccaaaggt tctcttagtg ctcgatgtga caactctgga      300
cggtgcagct gtaaaccagg tgtgacagga gccagatgcg accgatgtct gccaggcttc      360
cacatgctca cggatgcggg gtgcacccaa gaccagagac tgctagactc caagtgtgac      420
tgtgacccag ctggcatcgc agggccctgt gacgcgggcc gctgtgtctg caagccagct      480
gttactggag aacgctgtga taggtgtcga tcaggttact ataatctgga tggggggaac      540
cctgagggct gtacccagtg tttctgctat gggcattcag ccagctgccg cagctctgca      600
gaatacagtg tccataagat cacctctacc tttcatcaag atgttgatgg ctggaaggct      660
gtccaacgaa atgggtctcc tgcaaagctc caatggtcac agcgccatca agatgtgttt      720
agctcagccc aacgactaga ccctgtctat tttgtggctc ctgccaaatt tcttgggaat      780
caacaggtga gctatgggca aagcctgtcc tttgactacc gtgtggacag aggaggcaga      840
cacccatctg cccatgatgt gattctggaa ggtgctggtc tacggatcac agctcccttg      900
atgccacttg gcaagacact gccttgtggg ctcaccaaga cttacacatt caggttaaat      960
gagcatccaa gcaataattg gagcccccag ctgagttact ttgagtatcg aaggttactg     1020
cggaatctca cagccctccg catccgagct acatatggag aatacagtac tgggtacatt     1080
gacaatgtga ccctgatttc agcccgccct gtctctggag ccccagcacc ctgggttgaa     1140
cagtgtatat gtcctgttgg gtacaagggg caattctgcc aggattgtgc ttctggctac     1200
aagagagatt cagcgagact ggggcctttt ggcacctgta ttccttgtaa ctgtcaaggg     1260 ggagggcct gtgatccaga cacaggagat tgttattcag gggatgagaa tcctgacatt      1320
gagtgtgctg actgcccaat tggtttctac aacgatccgc acgaccccg cagctgcaag      1380 ccatgtccct gtcataacgg gttcagctgc tcagtgatgc cggagacgga ggaggtggtg     1440
tgcaataact gccctcccgg ggtcaccggt gcccgctgtg agctctgtgc tgatggctac     1500 tttgggggacc ccttttggtga acatggccca gtgaggcctt gtcagccctg tcaatgcaac     1560
aacaatgtgg accccagtgc ctctgggaat tgtgaccggc tgacaggcag gtgtttgaag     1620
tgtatccaca acacagccgg catctactgc gaccagtgca aagcaggcta cttcggggac     1680
ccattggctc ccaacccagc agacaagtgt cgagcttgca actgtaaccc catgggctca     1740
gagcctgtag gatgtcgaag tgatggcacc tgtgtttgca gccaggatt tggtggcccc      1800 aactgtgagc atggagcatt cagctgtcca gcttgctata tcaagtgaa gattcagtgc      1860 atgttctgca acagccggat ggatgggaac ttagcataat ctcaaagagc aaccctgatg     1920
ctcccataac agcaggacct caacgtccaa gaagaatacc acaccttact tgagcccatt     1980
tacaagtcac ctcctgaaaa atccaagatg cctgtcagaa gcagctactg agggaagtga     2040
agatgttttt atttgttcat tgtcattgtg aagactgact aaagtcttac tgatcaagga     2100
gtttgtttga acatggtcag agagctttca aagtcatttc agaaagtgcc ccacaccatc     2160
ctcaacagat ggtttgatgg aagagaagta gccagctctg ctcaggaaat ccattagtaa     2220
ggtgcagata ccaccaaaga gatgtcccac atgtggcaga atgtaccttt ttccttatt      2280 tctttaaaat ctccatataa aaagggaaga tggatgcatg agggcctaga aaatgtttat     2340
ccctctggat caatcttagg aatctatcct aagaatcaga aatacagaaa atagtacaaa     2400
actcgaggcc atctaaaaat tcaaacacag gaaaatgatt aaattatgta cacttattca     2460
atggaatatt ttgcgaacac tataaatgtt ttccaagagt ttacaaaggg caaataccat     2520
```

-continued attaaaaata caatgtaaaa ctgg                                                    2544

<210> SEQ ID NO 3
<211> LENGTH: 632
<212> TYPE: PRT
<213> ORGANISM: Homo sapiens

<400> SEQUENCE: 3

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
                20                  25                  30

Lys Ser Arg Gln Cys Ile Phe Asp Arg Glu Leu His Arg Gln Thr Gly
            35                  40                  45

Asn Gly Phe Arg Cys Leu Asn Cys Asn Asp Asn Thr Asp Gly Ile His
        50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

-continued

```
Arg Pro Val Ser Gly Ala Pro Ala Pro Trp Val Glu Gln Cys Ile Cys
    370             375             380

Pro Val Gly Tyr Lys Gly Gln Phe Cys Gln Asp Cys Ala Ser Gly Tyr
385             390             395             400

Lys Arg Asp Ser Ala Arg Leu Gly Pro Phe Gly Thr Cys Ile Pro Cys
            405             410             415

Asn Cys Gln Gly Gly Gly Ala Cys Asp Pro Asp Thr Gly Asp Cys Tyr
            420             425             430

Ser Gly Asp Glu Asn Pro Asp Ile Glu Cys Ala Asp Cys Pro Ile Gly
            435             440             445

Phe Tyr Asn Asp Pro His Asp Pro Arg Ser Cys Lys Pro Cys Pro Cys
    450             455             460

His Asn Gly Phe Ser Cys Ser Val Met Pro Glu Thr Glu Glu Val Val
465             470             475             480

Cys Asn Asn Cys Pro Pro Gly Val Thr Gly Ala Arg Cys Glu Leu Cys
            485             490             495

Ala Asp Gly Tyr Phe Gly Asp Pro Phe Gly Glu His Gly Pro Val Arg
            500             505             510

Pro Cys Gln Pro Cys Gln Cys Asn Asn Asn Val Asp Pro Ser Ala Ser
    515             520             525

Gly Asn Cys Asp Arg Leu Thr Gly Arg Cys Leu Lys Cys Ile His Asn
    530             535             540

Thr Ala Gly Ile Tyr Cys Asp Gln Cys Lys Ala Gly Tyr Phe Gly Asp
545             550             555             560

Pro Leu Ala Pro Asn Pro Ala Asp Lys Cys Arg Ala Cys Asn Cys Asn
            565             570             575

Pro Met Gly Ser Glu Pro Val Gly Cys Arg Ser Asp Gly Thr Cys Val
            580             585             590

Cys Lys Pro Gly Phe Gly Gly Pro Asn Cys Glu His Gly Ala Phe Ser
    595             600             605

Cys Pro Ala Cys Tyr Asn Gln Val Lys Ile Gln Cys Met Phe Cys Asn
    610             615             620

Ser Arg Met Asp Gly Asn Leu Ala
625             630
```

```
<210> SEQ ID NO 4
<211> LENGTH: 13
<212> TYPE: PRT
<213> ORGANISM: Homo sapiens

<400> SEQUENCE: 4

Cys Met Phe Cys Asn Ser Arg Met Asp Gly Asn Leu Ala
1               5               10
```

```
<210> SEQ ID NO 5
<211> LENGTH: 39
<212> TYPE: DNA
<213> ORGANISM: Homo sapiens

<400> SEQUENCE: 5
tgcatgttct gcaacagccg gatggatggg aacttagca                                    39
```

```
<210> SEQ ID NO 6
<211> LENGTH: 2651
<212> TYPE: DNA
<213> ORGANISM: Homo sapiens

<400> SEQUENCE: 6
```

-continued

```
atgcctgcgc tctggctggg ctgctgcctc tgcttctcgc tcctcctgcc cgcagcccgg      60
gccacctcca ggagggaagt ctgtgattgc aatgggaagt ccaggcagtg tatctttgat     120
cgggaacttc acagacaaac tggtaatgga ttccgctgcc tcaactgcaa tgacaacact     180
gatggcattc actgcgagaa gtgcaagaat ggcttttacc ggcacagaga aagggaccgc     240
tgtttgccct gcaattgtaa ctccaaaggt tctcttagtg ctcgatgtga caactctgga     300
cggtgcagct gtaaaccagg tgtgacagga gccagatgcg accgatgtct gccaggcttc     360
cacatgctca cggatgcggg gtgcacccaa gaccagagac tgctagactc caagtgtgac     420
tgtgacccag ctggcatcgc agggccctgt gacgcgggcc gctgtgtctg caagccagct     480
gttactggag aacgctgtga taggtgtcga tcaggttact ataatctgga tgggggggaac     540 cctgagggct gtacccagtg tttctgctat gggcattcag ccagctgccg cagctctgca     600
gaatacagtg tccataagat cacctctacc tttcatcaag atgttgatgg ctggaaggct     660
gtccaacgaa atgggtctcc tgcaaagctc caatggtcac agcgccatca agatgtgttt     720
agctcagccc aacgactaga ccctgtctat tttgtggctc ctgccaaatt tcttgggaat     780
caacaggtga gctatgggca aagcctgtcc tttgactacc gtgtggacag aggaggcaga     840
cacccatctg cccatgatgt gattctggaa ggtgctggtc tacggatcac agctcccttg     900
atgccacttg gcaagacact gccttgtggg ctcaccaaga cttacacatt caggttaaat     960
gagcatccaa gcaataattg gagcccccag ctgagttact ttgagtatcg aaggttactg    1020
cggaatctca cagccctccg catccgagct acatatggag aatacagtac tgggtacatt    1080
gacaatgtga ccctgatttc agcccgccct gtctctggag ccccagcacc ctgggttgaa    1140
cagtgtatat gtcctgttgg gtacaagggg caattctgcc aggattgtgc ttctggctac    1200
aagagagatt cagcgagact ggggcctttt ggcacctgta ttccttgtaa ctgtcaaggg    1260
ggaggggcct gtgatccaga cacaggagat tgttattcag gggatgagaa tcctgacatt    1320
gagtgtgctg actgcccaat tggtttctac aacgatccgc acgaccccg cagctgcaag    1380 ccatgtccct gtcataacgg gttcagctgc tcagtgatgc cggagacgga ggaggtggtg    1440
tgcaataact gccctcccgg ggtcaccggt gcccgctgtg agctctgtgc tgatggctac    1500 tttgggacc cctttggtga acatggccca gtgaggcctt gtcagccctg tcaatgcaac    1560
aacaatgtgg accccagtgc ctctgggaat tgtgaccggc tgacaggcag gtgtttgaag    1620
tgtatccaca acacagccgg catctactgc gaccagtgca agcaggcta cttcgggggac    1680 ccattggctc ccaacccagc agacaagtgt cgagcttgca actgtaaccc catgggctca    1740
gagcctgtag gatgtcgaag tgatggcacc tgtgtttgca gccaggatt tggtggcccc    1800 aactgtgagc atggagcatt cagctgtcca gcttgctata tcaagtgaa gattcagatc    1860 taaacagatc attgtactcc attacatgga aagagccaca aaagtcaaaa caagagaact    1920
tctattgaaa gcatcttgac taataaaacc ctacctttgc gcagtgcatg ttctgcaaca    1980
gccggatgga tgggaactta gcataatctc aaagagcaac cctgatgctc ccataacagc    2040
aggacctcaa cgtccaagaa gaataccaca ccttacttga gcccatttac aagtcacctc    2100
ctgaaaaatc caagatgcct gtcagaagca gctactgagg gaagtgaaga tgttttatt    2160 tgttcattgt cattgtgaag actgactaaa gtcttactga tcaaggagtt tgtttgaaca    2220
tggtcagaga gctttcaaag tcatttcaga aagtgcccca caccatcctc aacagatggt    2280
ttgatggaag agaagtagcc agctctgctc aggaaatcca ttagtaaggt gcagatacca    2340
```

-continued

```
ccaaagagat gtcccacatg tggcagaatg tacctttttc cttattttct ttaaaatctc   2400
catataaaaa gggaagatgg atgcatgagg gcctagaaaa tgtttatccc tctggatcaa   2460
tcttaggaat ctatcctaag aatcagaaat acagaaaata gtacaaaact cgaggccatc   2520
taaaaattca aacacaggaa aatgattaaa ttatgtacac ttattcaatg gaatattttg   2580
cgaacactat aaatgttttc caagagttta caaagggcaa ataccatatt aaaaatacaa   2640
tgtaaaactg g                                                        2651

<210> SEQ ID NO 7
<211> LENGTH: 620
<212> TYPE: PRT
<213> ORGANISM: Homo sapiens

<400> SEQUENCE: 7

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320
```

```
Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
                340                 345                 350

Gly Glu Tyr Ser Thr Gly Tyr Ile Asp Asn Val Thr Leu Ile Ser Ala
                355                 360                 365

Arg Pro Val Ser Gly Ala Pro Ala Pro Trp Val Glu Gln Cys Ile Cys
        370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
                435                 440                 445

Phe Tyr Asn Asp Pro His Asp Pro Arg Ser Cys Lys Pro Cys Pro Cys
        450                 455                 460

His Asn Gly Phe Ser Cys Ser Val Met Pro Glu Thr Glu Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
                500                 505                 510

Pro Cys Gln Pro Cys Gln Cys Asn Asn Asn Val Asp Pro Ser Ala Ser
                515                 520                 525

Gly Asn Cys Asp Arg Leu Thr Gly Arg Cys Leu Lys Cys Ile His Asn
        530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
        595                 600                 605

Cys Pro Ala Cys Tyr Asn Gln Val Lys Ile Gln Ile
        610                 615                 620
```

<210> SEQ ID NO 8
<211> LENGTH: 30
<212> TYPE: DNA
<213> ORGANISM: Homo sapiens

<400> SEQUENCE: 8
aaggctgaga acgggaagct tgtcatcaat                                                          30

<210> SEQ ID NO 9
<211> LENGTH: 30
<212> TYPE: DNA
<213> ORGANISM: Homo sapiens

<400> SEQUENCE: 9
ttcccgtcta gctcagggat gaccttgccc                                                          30

-continued

```
<210> SEQ ID NO 10
<211> LENGTH: 20
<212> TYPE: DNA
<213> ORGANISM: Homo sapiens

<400> SEQUENCE: 10
gctacttcgg ggacccattg                                                20

<210> SEQ ID NO 11
<211> LENGTH: 20
<212> TYPE: DNA
<213> ORGANISM: Homo sapiens

<400> SEQUENCE: 11
caagctggac agctgaatgc                                                20

<210> SEQ ID NO 12
<211> LENGTH: 20
<212> TYPE: DNA
<213> ORGANISM: Homo sapiens

<400> SEQUENCE: 12
accagtgcaa agcaggctac                                                20

<210> SEQ ID NO 13
<211> LENGTH: 19
<212> TYPE: DNA
<213> ORGANISM: Homo sapiens

<400> SEQUENCE: 13
tcagggttgc tctttgaga                                                 19

<210> SEQ ID NO 14
<211> LENGTH: 21
<212> TYPE: DNA
<213> ORGANISM: Homo sapiens

<400> SEQUENCE: 14
ctgccaaatt tcttgggaat c                                              21

<210> SEQ ID NO 15
<211> LENGTH: 21
<212> TYPE: DNA
<213> ORGANISM: Homo sapiens

<400> SEQUENCE: 15
gccctgtcaa tgcaacaaca a                                              21
```

LAMC2-NR6A1 SPLICING VARIANT AND TRANSLATION PRODUCT THEREOF

TECHNICAL FIELD

The present invention broadly provides a novel LAMC2-NR6A1 splicing variant and translation products thereof, and various usages in which these are used.

BACKGROUND ART

Intractable cancer diseases often lead to death of patients, and one of the main causes thereof is the difficulty in diagnosing and detecting micrometastatic tumors. The lack of effective diagnostic methods for cancer invasion and metastasis not only makes it difficult to completely cure cancer diseases, but also greatly affects the quality of life (QOL) of patients. For example, metastatic tumors are not detected at the time of diagnosis in 20% to 30% of patients with stage II colorectal cancer, and distant metastasis may be found after selecting a surgical treatment method. In this case, cancer patients will be treated for distant metastatic cancer again after the operation, which increases the physical and economic burden. In the current clinical field of cancer treatment, there is a demand for a treatment method that provides a high QOL for patients with cancer that is unlikely to be completely cured while aiming to completely cure cancer diseases. Accordingly, the establishment of an effective evaluation method relative to invasion and metastasis at the time of diagnosis of cancer diseases is required not only for the establishment of a treatment method for intractable cancer in the future but also for clinical requirements for today.

Laminins are a group of heterotrimeric proteins found in the basal lamina, and form a part of the basement membrane. These proteins are classified based on three non-identical polypeptides that combine with each other to form a laminin structure. These three polypeptides are distinguished as alpha ($\alpha$) chains, beta ($\beta$) chains, and gamma ($\gamma$) chains, each of which has several types of molecular species (for example, $\alpha 1$ to $\alpha 5$, $\beta 1$ to $\beta$, and $\gamma 1$ and $\gamma 2$). Laminin 332 (also referred to as laminin 5 or LN5) is known to be present in the basal lamina and abundant in the basement membrane located between epithelial cells and the connective tissue lining the epithelial cells. The structure of laminin 332 among known laminins is unique from the viewpoint that it is the only laminin having a structure containing a gamma-2 ($\gamma 2$) chain that forms laminin 332 when being combined with an $\alpha 3$ chain and a $\beta 3$ chain. Physiologically, laminin 332 is known to be produced by epithelial cells and able to promote cell adhesion, proliferation, differentiation and/or migration. For example, when laminin 332 is secreted from epithelial cells, it is susceptible to protease degradation (by membrane type 1-matrix metalloproteinase-1 (MT1-MMP), for example). In some cases, laminin 332 is processed towards an N-terminal of a gamma-2 chain sequence to generate a fragment having an epidermal growth factor (EGF)-like activity including acceleration of cell migration and invasion (Koshikawa et al., J. Cell Biol., (2000) 148: pages 615-624).

It is known that an increased concentration or level of a laminin gamma 2 monomer in biological samples such as blood is associated with cancer, colorectal cancer and/or bladder cancer, and the like. For example, WO 2014/027701 discloses a method for providing diagnosis, prognosis, or risk classification for subjects having cancer or a risk of getting cancer, the method including a step of comparing the concentration of a laminin gamma-2 monomer in a sample derived from a subject with the concentration value of a reference laminin gamma-2 monomer to identify that the subject has cancer or has an increased risk of cancer being caused by the concentration of the laminin gamma-2 monomer in the sample which is higher than the concentration value of the reference laminin gamma-2 monomer. Furthermore, Patent Publication JP-A-2011-209281 discloses a test method for urologic cancer and a kit for the test which are characterized by measuring a laminin $\gamma 2$ single chain in urine collected from a subject.

CITATION LIST

Non-Patent Document

Non-Patent Document 1: Koshikawa et al., J. Cell Biol., (2000) 148: pages 615-624

Patent Document

Patent Document 1: Japanese Translation of PCT Application No, 2015-527562
Patent Document 2: Patent Publication JP-A-2011-209281

SUMMARY

Technical Problem

An object of the present invention is to provide splicing variants generated via alternative splicing after binding of a portion of the sense strand of laminin $\gamma 2$ (LAMC2) gene and a portion of the antisense strand of NR6A1 gene, and translation products of these splicing variants, particularly, a novel peptide derived from a laminin $\gamma 2$ monomer, and usages thereof.

Solution to Problem

The inventors of the present invention found that a novel gene is generated by binding of exon 12 of laminin $\gamma 2$ (LAMC2) gene and intron 1 of the antisense strand of NR6A1 gene, which is one kind of nuclear receptor, and alternative splicing thereafter, and that this novel gene and translation products thereof are expressed in various cancer cells, thereby completing the present invention. In the present specification, one in which the LAMC2 gene and the NR6A1 gene are bound to each other at the genomic level is referred to as an "LAMC2-NR6A1 gene" (SEQ ID NO: 1) (also referred to as an "LAMC2 fusion gene"), and splicing variants thereof are referred to as "LAMC2-NR6A1 splicing variants". Translation products of the LAMC2-NR6A1 splicing variants are also referred to as an LAMC2 fusion protein or an Ln-$\gamma 2$ fusion protein.

Such splicing variants can also be expressed as splicing variants derived from the exon 12 of the laminin $\gamma 2$ (LAMC2) gene and the intron 1 of the antisense strand of the NR6A1 gene. Those up to cytosine at the position 1857 of SEQ ID NO: 1 are derived from the LAMC2 gene, and those after adenine at the position 1858 are derived from the intron 1 of the antisense strand of the NR6A1 gene.

Among the LAMC2-NR6A1 splicing variants, a short one having a base sequence of 2544 bases (SEQ ID NO: 2) is called an LAMC2-NR6A1 splicing variant of "SHORT FORM" (hereinafter, also referred to as "Ln-$\gamma 2$F"), and a long one of 2651 bases (SEQ ID NO: 6) is called an LAMC2-NR6A1 splicing variant of "LONG FORM". Furthermore, a novel peptide having an amino acid sequence of SEQ ID NO: 4 (CMFCNSRMDGNLA) included in the SHORT FORM is referred to as an "LAMC2-NR6A1 peptide". However, it is assumed that many other LAMC2-NR6A1 splicing variants are present, and the SHORT FORM and the LONG FORM are merely some examples. Because it is thought that the splicing variants are involved in the activation of not only PI3K and Akt downstream of the EGF receptor signal transduction pathway but also the RAS/MAPK/ERK pathway, the splicing variants are expected to bind to the EGF receptor in the state of a fusion gene for activation downstream thereof. That is, the ligand domain of the EGF receptor is cut out by a protease to exhibit a ligand activity in the case of a laminin γ2 single chain, whereas a fusion gene product, which is in the original state of its expressed form, exhibits a ligand activity, and therefore, it is thought that RSK and the like downstream of ERK also contribute to activity control. Therefore, it is sufficient for the splicing variant to have the sequence of SEQ ID NO: 2, for example, the sequence shown at the positions 1919 to 2544 of SEQ ID NO: 2, particularly the base sequence encoding the amino acid sequence of SEQ ID NO: 4, and the translation products thereof to be those having an EGF receptor ligand activity, namely those activating expression and/or phosphorylation of PI3K and Akt downstream of the EGF receptor signal transduction pathway, and/or ERK downstream of the RAS/MAPK/ERK signal transduction pathway, and in some cases, RSK further downstream thereof.

That is, the present application includes the following inventions.

[1] A splicing variant derived from exon 12 of laminin γ2 (LAMC2) gene and intron 1 of the antisense strand of NR6A1 gene.

[2] The splicing variant according to [1], which has a nucleic acid encoding a peptide of the following (a), (b), or (c):

(a) a peptide having an amino acid sequence of SEQ ID NO: 4;

(b) a peptide having an amino acid sequence in which one or several amino acids have been deleted, substituted, and/or added in the amino acid sequence of SEQ ID NO: 4, and having an activity of enhancing activities of an EGF receptor and a downstream signaling pathway thereof; and (c) a peptide having an amino acid sequence having 80% or more or preferably 90% or more identity to the amino acid sequence of SEQ ID NO: 4, and having an activity of enhancing activities of an EGF receptor and a downstream signaling pathway thereof.

[3] The splicing variant according to [1] or [2], which has a base sequence shown at positions 1919 to 2544 of SEQ ID NO: 2.

[4] A protein encoded by the splicing variant according to any one of [1] to [3].

[5] A peptide of the following (a), (b), or (c), or a salt thereof:

(a) a peptide having an amino acid sequence of SEQ ID NO: 4;

(b) a peptide having an amino acid sequence in which one or several amino acids have been deleted, substituted, and/or added in the amino acid sequence of SEQ ID NO: 4, and having an activity of enhancing activities of an EGF receptor and a downstream signaling pathway thereof; and (c) a peptide having an amino acid sequence having 80% or more or preferably 90% or more identity to the amino acid sequence of SEQ ID NO: 4, and having an activity of enhancing activities of an EGF receptor and a downstream signaling pathway thereof.

[6] A nucleic acid encoding the peptide according to [5], or a nucleic acid complementary thereto.

[7] A composition containing a compound or a salt thereof which inhibits expression of the peptide according to [5] or the nucleic acid according to [6].

[8] The composition according to [7], in which the compound is an antibody, an antigen-binding fragment thereof, or a nucleic acid.

[9] The composition according to [8], in which the nucleic acid is siRNA that cleaves mRNA.

[10] A pharmaceutical composition for treating or preventing a disease associated with activities of an EGF receptor and a downstream signaling pathway thereof, the pharmaceutical composition containing a compound or a salt thereof which inhibits expression of the peptide according to [5] or the nucleic acid according to [6].

[11] The pharmaceutical composition according to [10], in which the disease is cancer, obesity, an autoimmune disease, inflammation, heart disease, a neurodegenerative disease, or diabetes.

[12] The pharmaceutical composition according to [11], in which the disease is cancer, and the pharmaceutical composition is for preventing or treating the cancer, or suppressing invasion, metastasis, or recurrence of the cancer.

[13] A vector containing the splicing variant according to any one of [1] to [3] or the nucleic acid according to [6].

[14] A recombinant cell containing the vector according to [13].

[15] An animal model transformed by the splicing variant according to any one of [1] to [3] or the nucleic acid according to [6].

[16] An antibody or an antigen-binding fragment thereof which binds to a translation product of the splicing variant according to any one of [1] to [3] or to the peptide according to [5] and does not bind to wild-type laminin γ2 (LAMC2).

[17] A pair of oligonucleotide primers for detecting or amplifying a nucleic acid encoding the peptide according to [5], the pair of oligonucleotide primers including: a sense primer; and an antisense primer.

[18] A nucleic acid having an activity of binding to mRNA encoding the peptide according to [5] to inhibit translation from the mRNA into a protein.

[19] The nucleic acid according to [18], in which the nucleic acid is siRNA that cleaves mRNA.

[20] A vector containing the nucleic acid according to [18] or [19].

[21] A recombinant cell containing the vector according to [20].

[22] A method for treating or preventing a disease associated with activities of an EGF receptor and a downstream signaling pathway thereof in a subject, the method including administering, to the subject, a compound or a salt thereof which inhibits expression of the peptide according to [5] or the nucleic acid according to [6].

[23] The method according to [22], in which the disease is cancer, obesity, an autoimmune disease, inflammation, heart disease, a neurodegenerative disease, or diabetes.

[24] A biomarker containing any of the following (a) to (e):

(a) the splicing variant according to any one of [1] to [3], preferably a splicing variant having a base sequence of SEQ ID NO: 2 or 6;

(b) a protein encoded by the splicing variant according to any one of [1] to [3], preferably the splicing variant having the base sequence of SEQ ID NO: 2 or 6;

(c) a peptide having an amino acid sequence of SEQ ID NO: 4;

(d) a nucleic acid encoding the peptide of (c) or a nucleic acid complementary thereto; and (e) an antibody against the protein of (b) or the peptide of (c).

[25] The biomarker according to [24], which is for diagnosing a disease associated with activities of an EGF receptor and a downstream signaling pathway thereof.

[26] The biomarker according to [25], in which the disease is cancer, obesity, an autoimmune disease, inflammation, heart disease, a neurodegenerative disease, or diabetes.

[27] The biomarker according to [25] or [26], in which the disease is cancer, and the biomarker is a tumor marker for diagnosing susceptibility to cancer, whether or not cancer has developed, or whether or not cancer has progressed.

[28] A method for detecting a biomarker of a disease associated with activities of an EGF receptor and a downstream signaling pathway thereof, in which a sample derived from a subject contains any of the following (a) to (e):

(a) the splicing variant according to any one of [1] to [3], preferably a splicing variant having a base sequence of SEQ ID NO: 2 or 6;

(b) a protein encoded by the splicing variant according to any one of [1] to [3], preferably the splicing variant having the base sequence of SEQ ID NO: 2 or 6;

(c) a peptide having an amino acid sequence of SEQ ID NO: 4;

(d) a nucleic acid encoding the peptide of (c) or a nucleic acid complementary thereto; and (e) an antibody against the protein of (b) or the peptide of (c).

[29] The method according to [28], further including a step of determining whether the disease associated with the activities of the EGF receptor and the downstream signaling pathway thereof is likely to develop, whether the disease has developed, or whether the disease has progressed when the biomarker is detected or is present in a high concentration as compared to a healthy individual.

[30] The method according to [28] or [29], in which the disease is cancer, obesity, an autoimmune disease, inflammation, heart disease, a neurodegenerative disease, or diabetes.

[31] The method according to [30], in which the disease is cancer, and the biomarker is a tumor marker for diagnosing susceptibility to cancer, whether or not cancer has developed, or whether or not cancer has progressed.

[32] A method for diagnosing a disease associated with activities of an EGF receptor and a downstream signaling pathway thereof in a subject, the method including a step of detecting, in the subject, a biomarker of the disease associated with the activities of the EGF receptor and the downstream signaling pathway thereof, the biomarker containing any of the following (a) to (e):

(a) the splicing variant according to any one of [1] to [3], preferably a splicing variant having a base sequence of SEQ ID NO: 2 or 6;

(b) a protein encoded by the splicing variant according to any one of [1] to [3], preferably the splicing variant having the base sequence of SEQ ID NO: 2 or 6;

(c) a peptide having an amino acid sequence of SEQ ID NO: 4;

(d) a nucleic acid encoding the peptide of (c) or a nucleic acid complementary thereto; and (e) an antibody against the protein of (b) or the peptide of (c).

[33] The method according to [32], further including a step of determining whether the disease associated with the activities of the EGF receptor and the downstream signaling pathway thereof is likely to develop, whether the disease has developed, or whether the disease has progressed when the biomarker is detected or is present in a high concentration as compared to a healthy individual.

[34] The method according to [32] or [33], in which the disease is cancer, obesity, an autoimmune disease, inflammation, heart disease, a neurodegenerative disease, or diabetes.

[35] The method according to [34], in which the disease is cancer, and the biomarker is a tumor marker for diagnosing susceptibility to cancer, whether or not cancer has developed, or whether or not cancer has progressed.

[36] A method for screening a medicine for treating or preventing a disease associated with activities of an EGF receptor and a downstream signaling pathway thereof, the method including a step of selecting, as the medicine, a substance that inhibits expression of the peptide according to [5] or the nucleic acid according to [6].

[37] The method according to [36], in which the disease is cancer, obesity, an autoimmune disease, inflammation, heart disease, a neurodegenerative disease, or diabetes.

Advantageous Effects of Invention

Since the LAMC2-NR6A1 splicing variants of the present invention, and the translation products thereof, particularly the LAMC2-NR6A1 peptide, are novel ones specifically detected in cancer cells, they are expected to be provided for various usages. For example, by constructing a detection system of the LAMC2-NR6A1 splicing variants and the translation products thereof, detection of cancer is also possible. In particular, because the LAMC2-NR6A1 peptide has an amino acid sequence that is not present in normal cells, by using a system capable of specifically detecting this amino acid sequence, a detection system without a non-specific reaction (derived from normal cells) can be theoretically obtained. In addition, because the LAMC2-NR6A1 splicing variants are thought to control the motility of cancer cells, they can also be utilized as a marker for predicting the degree of malignancy of cancer. Furthermore, substances inhibiting the expression of the LAMC2-NR6A1 splicing variants are expected to have the effect of suppressing invasion and metastasis of cancer.

BRIEF DESCRIPTION OF DRAWINGS

FIG. 2 is a schematic diagram showing the state in which the sense strand of LAMC2 gene and the antisense strand of NR6A1 gene are bound to each other at the genomic level.

DESCRIPTION OF EMBODIMENTS

Hereinafter, embodiments of the present invention (hereinafter referred to as "the present embodiment") will be described, but the scope of the present invention is not construed as being limited to the following embodiments.
Peptide The first aspect provides translation products, in particular, the following peptides or salts thereof, the translation products being encoded by novel splicing variants generated by fusion of exon 12 of laminin γ2 gene, and intron 1 of the antisense strand of NR6A1 gene, which is one kind of nuclear receptor.

(a) A peptide having the amino acid sequence (CMFCN-SRMDGNLA) of SEQ ID NO: 4;

(b) A peptide having the amino acid sequence in which one or several, for example, 1 to 5 amino acids have been deleted, substituted, and/or added in the amino acid sequence of SEQ ID NO: 4, and having the activity of enhancing the activities of an EGF receptor and the downstream signaling pathway thereof; and (c) A peptide having the amino acid sequence having 80% or more or preferably 90% or more identity to the amino acid sequence of SEQ ID NO: 4, and having the activity of enhancing the activities of the EGF receptor and the downstream signaling pathway thereof.

A laminin γ2 single chain (also referred to as "Ln-γ2m" in the present specification) refers to one in which a γ2 chain, which is a constituent element of laminin 332, is expressed as a monomer. Laminin 5 is one of the major constituent components of the basement membrane, and is a heterotrimer in which three polypeptide chains, which are an α3 chain, a β3 chain, and a γ2 chain, are associated at a coiled-coil structure portion. Of the three polypeptide chains, the γ2 chain is reported to be expressed as a monomer in malignant cancer cells. In the present specification, in order to distinguish the γ2 chain expressed as a trimer from the "γ2 chain of laminin 332", the γ2 chain expressed as a monomer is referred to as a "laminin γ2 single chain" or a "laminin γ2 chain".

When used in the present specification, the "amino acid sequence in which one or several amino acids have been deleted, substituted, and/or added" means a mutated amino acid sequence in which the number of amino acids that have been deleted, substituted, and/or added is in the range in which the desired function is not lost, as compared to amino acid sequences specified by SEQ ID NOs. Amino acids may refer to natural amino acids, synthetic amino acids, and amino acid analogs and amino acid mimetics which function similarly to natural amino acids. The amino acids may be any of L-amino acids or D-amino acids. The natural amino acids are amino acids encoded by the genetic code, and amino acids modified after translation in cells.

The substitution is preferably a conservative amino acid substitution. This is because when it is a conservative amino acid substitution, there is a high likelihood of obtaining a structure or property substantially equivalent to that of an LAMC2-NR6A1 peptide.

Figure 14:
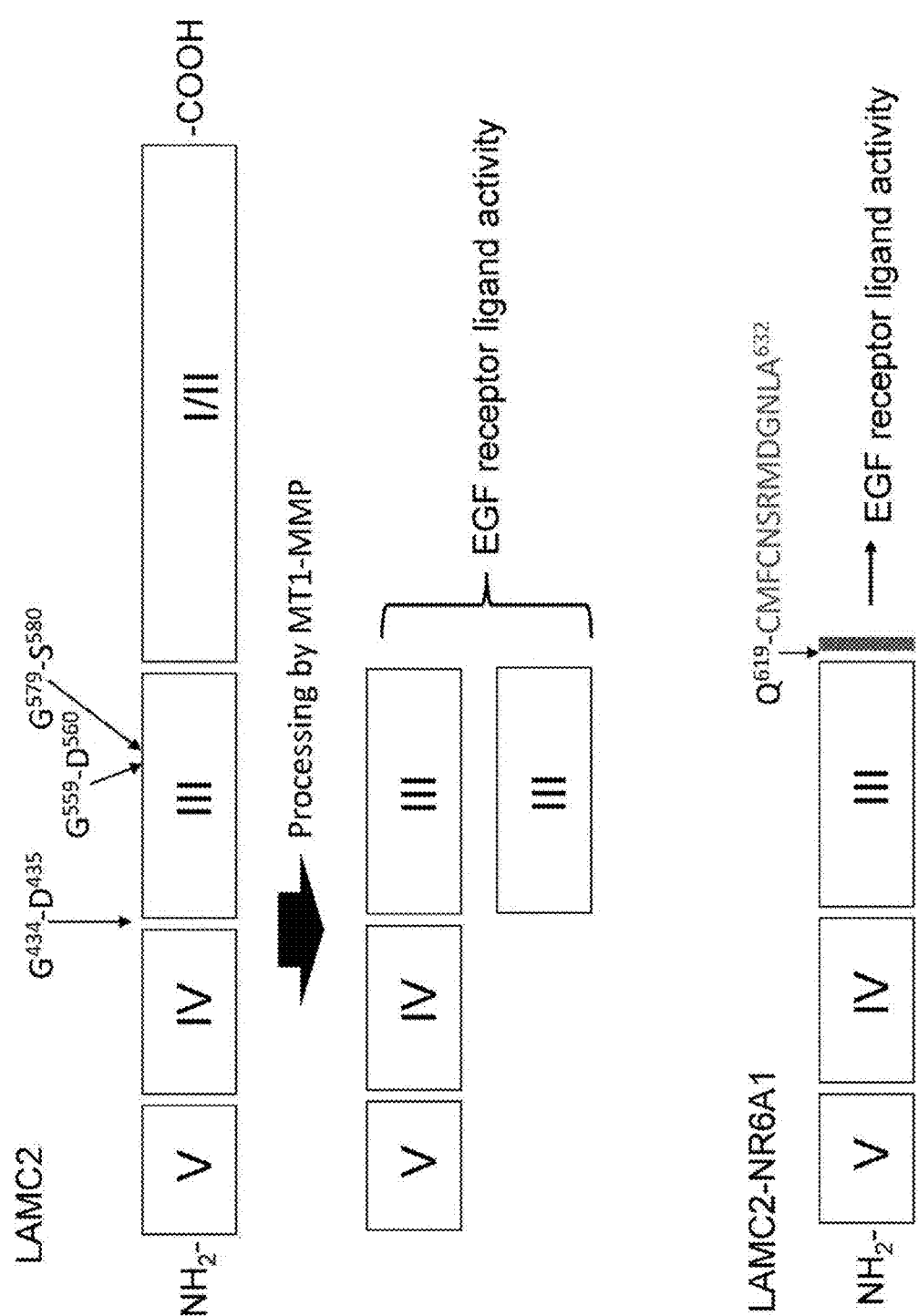
FIG. 14 is a schematic diagram of the translation products of LAMC2 and an LAMC2-NR6A1 splicing variant.
Figure 15:
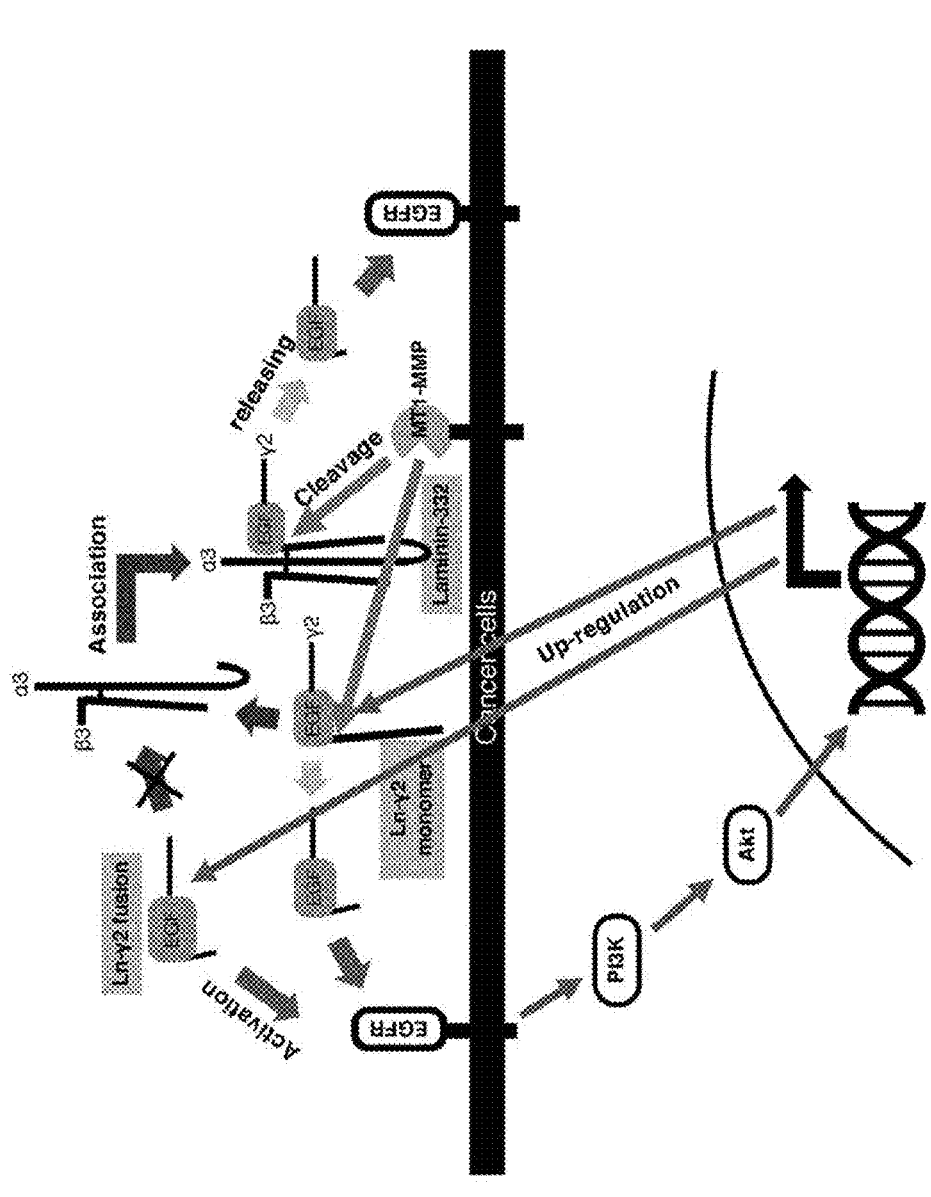
FIG. 15 shows that the Ln-γ2 fusion protein, which is in the original form without being processed by MT1-MMP, activates an EGF receptor, thereby contributing to the promotion of canceration.

The laminin γ2 (Ln-γ2) chain translated from LAMC2 is produced as a single chain, or as laminin 332 associated with the laminin α3 and β3 chains. It is thought that MT1-MMP cuts out the laminin EGF-like domain (domain III) in the short arm of these Ln-γ2 chains to release the fragment containing the domain III having the ligand activity of an epidermal growth factor receptor (EGFR) (upper part of FIG. 14), thereby contributing to the movement of cancer cells, the enhancement of survival signals, and the like through activation of ErbB receptors (FIG. 15). In order for Ln-γ2 to act as an EGF receptor ligand, processing by MT1-MMP is indispensable. On the other hand, an Ln-γ2 fusion protein, which is a translation product of LAMC2-NR6A1, activates an EGF receptor in the original form without requiring processing by MT1-MMP, thereby contributing to the promotion of canceration (lower part of FIG. 14). Based on the above description, the Ln-γ2 fusion protein, which is a translation product of LAMC2-NR6A1, can efficiently activate an ErbB receptor without requiring processing by a protease.

Although not intended to be restrained by theory, splicing variants having the LAMC2-NR6A1 peptide have the activity of directly activating the epidermal growth factor receptor (EGFR) to enhance the activity of the downstream signaling pathway thereof without being processed by MT1-MMP, and it is thought that this activity enhancement is involved in cancer. Here, PI3K-Akt and Ras-ERK pathways, which are important signal transduction pathways associated with cancer, are investigated. The PI3K-Akt pathway starts from the phosphorylation activity of PI3K, and inhibits survival and apoptosis induction of cells through phosphorylation of Akt. That is, expression and/or phosphorylation of Akt is associated with cancer. In fact, the PI3K-Akt pathway is confirmed to be constantly hyperfunctional in many tumors. Furthermore, Akt is known to be associated with diseases other than cancer, such as obesity, autoimmune diseases, inflammation, or diabetes.

An MAPK/ERK pathway starts from phosphorylation activation of RAS, and induces cell proliferation through phosphorylation of Raf, MEK, and ERK. That is, expression and/or phosphorylation of a Ras-ERK pathway is associated with cancer. In fact, the Ras-ERK pathway plays an important role in the enhancement of pathway cell proliferation in many tumors, and is therefore thought to be involved in canceration. Furthermore, it is confirmed that the function of ERK is constantly enhanced in cancer cells. Furthermore, ERK is known to be associated with diseases other than cancer, such as heart diseases accompanied by cardiomyocyte hypertrophy, and neurodegenerative diseases. Because the LAMC2-NR6A1 peptide is expressed in various cancer cells, its application to various usages associated with cancer is expected regardless of the mechanism of the effect.

The LAMC2-NR6A1 peptide can be obtained by artificial conventional methods in the technical field, such as chemical synthesis and recombinant DNA technology. For example, the LAMC2-NR6A1 peptide can be prepared by binding an amino acid to a solid phase carrier insoluble in a reaction solvent according to a solid phase method, and performing a sequential condensation reaction on this amino acid to extend the peptide chain.

Nucleic Acid

In the second aspect, a nucleic acid encoding the amino acid sequence of the LAMC2-NR6A1 peptide or a nucleic acid complementary thereto is provided.

A method for obtaining the nucleic acid is not particularly limited, and for example, the nucleic acid can be obtained by preparing an appropriate probe and library based on the information of the base sequence of the nucleic acid corresponding to the amino acid sequence disclosed in the present specification, and screening a cDNA library and a genomic DNA library using them. For example, it can be produced by selecting a desired clone from a genomic DNA library using an appropriate probe and the like specific to a desired gene. Separation of total RNA from cell lines, separation and purification of mRNA, acquisition of genomic DNA and cloning thereof, and the like can all be performed according to a conventional method.

As a probe used in the above-mentioned method, DNA, which is chemically synthesized based on the information relating to the base sequence of a desired nucleic acid, and the like can be generally used. Furthermore, a sense primer and an antisense primer set based on the base sequence information of the nucleic acid can be used as a probe for screening. For example, a sense primer and an antisense primer designed to sandwich the region encoding LAMC2-NR6A1 peptide are suitably used. Examples of such a pair of oligonucleotide primers include primers set forth in SEQ ID NO: 12 and SEQ ID NO: 13.

When acquiring the nucleic acid, a DNA amplification method by PCR can be suitably used. Isolation and purification of amplified DNA fragment can be performed according to a conventional method. Examples thereof include gel electrophoresis and the like. The base sequence of the nucleic acid obtained according to the above-mentioned method can be determined according to a conventional method such as a dideoxy method or a Maxam-Gilbert method.

The nucleic acid also include a nucleic acid which hybridizes with a nucleic acid consisting of a base sequence specified by a corresponding sequence identification number and a base sequence complementary thereto under a highly stringent condition, and which encodes a peptide having the same activity as that of the above nucleic acid.

Here, when used in the present specification, the "highly stringent condition" refers to a condition in which a so-called specific hybrid is formed and a non-specific hybrid is not formed. Examples of the highly stringent condition include a condition in which nucleic acids with high identity hybridize with each other and nucleic acids with lower identity than the above identity do not hybridize with each other, for example, a condition disclosed in Molecular cloning a Laboratory manual 2nd edition (Sambrook et al., 1989). Specific examples thereof include a condition under which hybridization is performed at 60° C. and at a salt concentration corresponding to 1×SSC and 0.1% SDS, preferably 0.1×SSC and 0.1% SDS, which is a washing condition in normal Southern hybridization.

Splicing Variants

Figure 2:
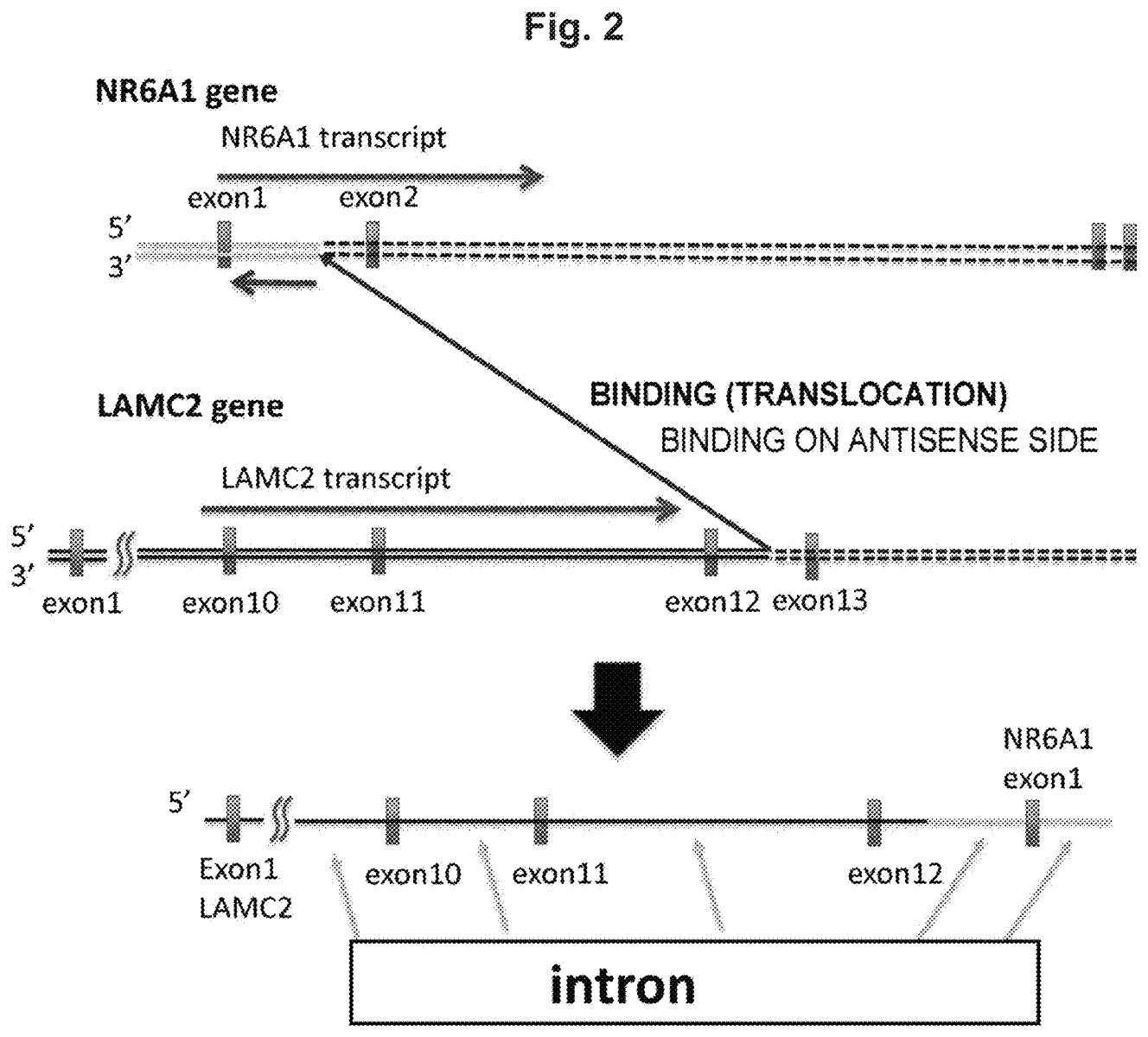
Figure 3:
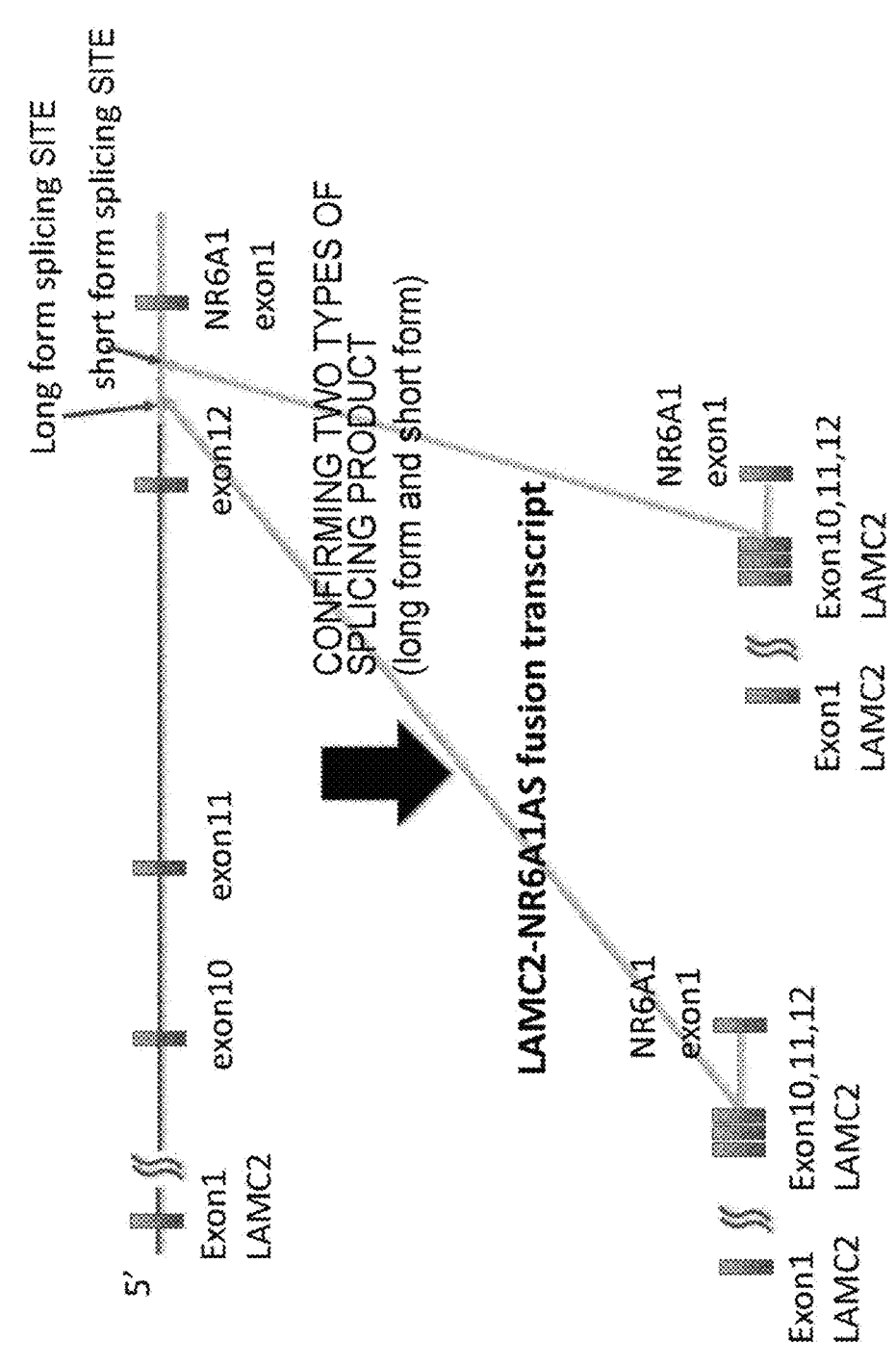
FIG. 3 is a schematic diagram showing the state in which splicing variants of SHORT FORM and LONG FORM are generated by causing alternative splicing at the mRNA level after binding of the LAMC2 gene and the NR6A1 gene.

Since the LAMC2-NR6A1 gene is one in which the sense strand of LAMC2 and the antisense strand of NR6A1 are bound to each other, translation products thereof contain the amino acid sequence encoded by the sense strand of LAMC2, but does not contain the amino acid sequence encoded by the sense strand of the NR6A1 gene. After this binding at the genomic level, mature mRNA is ultimately generated by alternative splicing (FIG. 2 and FIG. 3). As a result of the alternative splicing, a plurality of alternative splicing variants encoding different isoforms, such as those with 2544 bases (SEQ ID NO: 2) and those with 2651 bases (SEQ ID NO: 6), are present in the transcription product of the LAMC2-NR6A1 gene. For convenience, the former is referred to as "SHORT FORM" and the latter is referred to as "LONG FORM" in the present specification. However, there is no intention to exclude splicing variants with other base lengths, and the invention of the present application broadly includes all splicing variants of the LAMC2-NR6A1 gene. The splicing variant preferably has the sequence of SEQ ID NO: 2, for example, the sequence shown at the position 1919 to the position 2544 of SEQ ID NO: 2, particularly the base sequence encoding the amino acid sequence of SEQ ID NO: 4, and the translation products thereof are preferably those having an EGF receptor ligand activity, namely those activating PI3K and Akt downstream of the EGF signal transduction pathway. When used in the present specification, the "splicing variant" refers to mature mRNA as an alternative splicing product of a gene.

Transcription and splicing from an LAMC2 gene promoter of a translocation gene generate mRNAs of multiple molecular species. A protein translated from mRNA has a sequence (up to isoleucine at the position 618 of SEQ ID NO: 3) derived from laminin γ2 at the N-terminal, and a peptide sequence read from NR6A1-derived mRNA is added to the C-terminal. The amino acid sequence added to the C-terminal changes depending on differences in splicing sites, and typical examples include the amino acid sequence of SEQ ID NO: 4 (CMFCNSRMDGNLA).

Translation of SHORT FORM stops at a state in which the peptide (SEQ ID NO: 4) consisting of 13 amino acids is added to the translation product of LAMC2. On the other hand, in the translation product of LONG FORM, one amino acid is added to the translation product of LAMC2 at the time of translation into an amino acid, but since a stop codon is contained immediately thereafter, the above-mentioned peptide is not added.

Vector and the Like

In another embodiment, a vector containing a nucleic acid encoding an LAMC2-NR6A1 peptide or a nucleic acid complementary thereto, a recombinant cell containing the vector, and an animal model transformed by the nucleic acid are provided. The vector may be constituted such that the nucleic acid encoding the peptide of SEQ ID NO: 4, and other desired nucleic acids are all contained in one expression vector, or may be constituted such that they are divided into two or more groups, of which each is contained in a separate expression vector. In the expression vector, the nucleic acid can be inserted between a promoter and a terminator.

Furthermore, the vector can further contain selectable marker genes (genes that confer resistance to drugs such as tetracycline, ampicillin, kanamycin, hygromycin, and phosphinothricin, genes that complement auxotrophic mutation, and the like) which are for selecting transformed cells.

The vector may be a plasmid or a virus vector as an expression vector. Furthermore, when there is an intention to administer to mammals such as humans, the vector may be a virus vector such as adenoviruses, retroviruses, adeno-associated viruses, herpesviruses, vaccinia viruses, poxviruses, polioviruses, Sindbis viruses, Sendai viruses, and Epstein-Barr virus.

The animal model may be used to study diseases associated with the activities of EGF receptors and downstream signaling pathways thereof, such as the development, treatment or prevention, and the like of cancer. The animal model intends to include any vertebrates including non-human primates (for example, monkeys such as crab-eating macaques, rhesus macaques, and chimpanzees), and other mammals, for example, cows, pigs, camels, llamas, horses, goats, rabbits, sheep, hamsters, guinea pigs, cats, dogs, rats, and mice). In order to create the animal model transformed to express a desired nucleic acid, it is sufficient to introduce a desired gene into a fertilized egg or early embryo, transplant the fertilized egg or early embryo into which the gene has been introduced into the uterus of a foster mother of the above-mentioned animal, and cause development. In addition, a homozygous transformed animal model can be created by inserting pluripotent stem cells such as embryonic stem cells (ES cells) and induced pluripotent stem cells (iPS cells) into which a desired gene has been introduced into an early embryo such as a blastocyst, transplanting the chimeric embryo thus obtained into the uterus of a foster mother, and mating the chimeric animal obtained by development.

In addition to the animal model transformed to express the above-mentioned fusion gene, animals in which the above-mentioned fusion gene has been knocked down or knocked out are also intended to be included in the scope of the present invention.

Composition

In still another embodiment, a composition, preferably a pharmaceutical composition, containing a compound or a salt thereof which inhibits the expression of the above-mentioned peptide or nucleic acid are provided. Such a compound may be an antibody or an antigen-binding fragment thereof, or a nucleic acid. When used in the present specification, the "antibody" means an antibody molecule capable of immunospecifically binding to a desired antigen or the like. Examples of the antibody include antiserums, polyclonal antibodies, monoclonal antibodies, chimeric antibodies, human antibodies, humanized antibodies, recombinant antibodies, single-chain Fvs ("scFv"), single-chain antibodies, single-domain antibodies, F(ab) fragments, F(ab') fragments, disulfide-linked Fvs ("sdFv"), anti-idiotype antibodies, and epitope-binding fragments in which any function of the above examples is active.

When used in the present specification, the "antigen-binding fragment" refers to any fragment of an antibody that retains the ability to immunospecifically bind to a target peptide or the like. The antigen-binding fragment include fragments containing a light chain variable region (VL), a heavy chain variable region (VH), a complementarity determining region (CDR), and the like which specifically bind to single-chain antibodies, Fab fragments, F(ab')2 fragments, disulfide-bonded Fvs, target peptides, and the like. The antibody-binding fragment can be obtained by a method known in the art.

As mentioned above, since the LAMC2-NR6A1 peptide or the nucleic acid has an activity of enhancing the activities of the EGF receptor and the downstream signaling pathway thereof, the compound inhibiting the above activity can be suitably used for treating or preventing diseases associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes. The compound having such an activity may be an antibody or an antigen-binding fragment thereof, or an antisense medicine such as siRNA and ribozyme, for example. Any antisense nucleic acid can be used as long as it binds to mRNA encoding a target peptide and has an activity of inhibiting the translation from the mRNA into a protein. For example, as an antisense nucleic acid, siRNA that cleaves mRNA, or a nucleic acid that is transcribed into siRNA or a precursor thereof in a cell can also be suitably used.

siRNA is double-stranded RNA usually having about 19 to 30 bases, for example, about 21 bases to 25 bases, and generally, one of them has a base sequence complementary to a part of a target mRNA, and the other one has a sequence complementary thereto, but it does not have to be completely complementary to the target mRNA.

An expression inhibition method using the siRNA, that is, an RNAi method is a sequence-specific gene expression suppression mechanism induced by a double-stranded nucleic acid. The siRNA also has high target specificity, and is highly safe because it is a method utilizing a gene expression suppression mechanism that is originally present in the living body.

The typical structure of the siRNA is a double-stranded RNA with 21 base pairs, and the 3'-portion of each RNA strand has overhangs of 2 bases. The siRNA is produced by cutting out hairpin RNA (shRNA) or longer double-stranded RNA by a Dicer. The shRNA or long double-stranded RNA before being cleaved by the Dicer can be suitably used in the present invention as a precursor of the siRNA.

The siRNA can be designed according to a known method based on the base sequence of the target mRNA. Furthermore, as long as the siRNA has an RNAi effect on the target mRNA, the siRNA may be double-stranded RNA, may be a DNA-RNA chimeric double-stranded nucleic acid, or may be an artificial nucleic acid or a nucleic acid that have undergone various modifications.

The composition can be broadly and suitably used for treating or preventing diseases associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes. The composition may be used for such medicine usages, particularly for the treatment or prevention of cancer, for example, suppression of cancer cell proliferation, and furthermore, suppression of canceration of cells, suppression of malignant transformation of cancer cells, or suppression of invasion, metastasis, or recurrence of cancer. In the present specification, the "cancer" is used in its broadest sense. Examples of the cancer include, but are not limited to, brain tumor, head and neck cancer, esophageal cancer, stomach cancer, large bowel cancer (excluding colon cancer), anal cancer, rectal cancer, liver cancer, hepatocellular carcinoma, lung cancer, non-small cell lung cancer, bone sarcoma, gallbladder cancer, pancreatic cancer, breast cancer, prostate cancer, testicular tumor, bladder cancer, and skin cancer.

The route of administering the composition is not particularly limited, and the composition can be administered orally or parenterally. Examples of compositions suitable for oral administration include granules, fine granules, powders, hard capsules, soft capsules, syrups, emulsions, suspensions, and solutions. Examples of compositions suitable for parenteral administration include injections for intravenous administration, intramuscular administration, or subcutaneous administration, infusions, suppositories, transdermal absorbents, transmucosal absorbents, nasal drops, ear drops, eye drops, and inhalants. It is also intended to dissolve a preparation prepared as a pharmaceutical composition in the form of a dry powder such as a freeze-dried product at the time of use to use it as an injection or an infusion.

The composition may include a solid or liquid additive for preparations. The additive for preparations may be any of an organic substance or an inorganic substance. When producing an oral solid preparation, for example, an excipient is added to a substance selected from the group consisting of the above-mentioned compounds or salts thereof, which are active ingredients, and hydrates thereof and solvates thereof, and furthermore, a binder, a disintegrant, a lubricant, a colorant, a flavoring agent, or the like is added if necessary, and thereby a preparation in the form of a tablet, a coated tablet, a granule, a powder, a capsule, or the like can be prepared by a conventional method.

Examples of the excipient include lactose, sucrose, saccharose, glucose, corn starch, starch, talc, sorbitol, crystalline cellulose, dextrin, kaolin, calcium carbonate, and silicon dioxide. Examples of the binder include polyvinyl alcohol, polyvinyl ether, ethyl cellulose, methyl cellulose, gum arabic, tragacanth, gelatin, shellac, hydroxypropyl cellulose, hydroxypropyl methyl cellulose, calcium citrate, dextrin, and pectin. Examples of the lubricant include magnesium stearate, talc, polyethylene glycol, silica, and hydrogenated vegetable oil. As the colorant, any one can be used as long as it is approved to be added to pharmaceutical products. As the flavoring agent, cocoa powder, peppermint camphor, aromatic acid, mentha oil, borneol, cinnamon bark powder, and the like can be used. The tablet and the granule can be appropriately coated with sugar, gelatin, or any other coating as needed. In addition, preservatives, antioxidants, or the like may be added as needed.

For the production of a liquid preparation for oral administration, such as emulsions, syrups, suspensions, or solutions, generally used inert diluents such as water or vegetable oil can be used. To the liquid preparation, adjuvants such as wetting agents, suspension adjuvants, sweeteners, aromatics, colorants, and preservatives can be added. After preparing the liquid preparation, it may be filled in a capsule of gelatin or the like.

Examples of solvents or suspensions used for producing a pharmaceutical composition for parenteral administration, such as an injection or a suppository, include water, propylene glycol, polyethylene glycol, benzyl alcohol, ethyl oleate, and lecithin. Examples of bases used for producing a suppository include cacao butter, emulsified cacao butter, and laurin butter. A method for preparing the preparation is not particularly limited, and any method generally used in the art can be utilized.

When preparing the pharmaceutical composition in the form of an injection, for example, diluents such as water, ethyl alcohol, and propylene glycol; pH adjusters or buffers such as sodium citrate, sodium acetate, and sodium phosphate; stabilizers such as ethylenediaminetetraacetic acid, thioglycolic acid, or thiolactic acid; or the like can be used as a carrier. Salt, glucose, mannitol, glycerin, or the like in a sufficient amount for preparing an isotonic solution may be blended in the composition, or solubilizing agents, soothing agents, local anesthetics, or the like can also be added.

When preparing the pharmaceutical composition in the form of ointments such as pastes, creams, and gels, generally used bases, stabilizers, wetting agents, preservatives, or the like can be used as needed, and the pharmaceutical composition can be prepared by mixing the components by a conventional method.

As the base, for example, white petrolatum, polyethylene, paraffin, glycerin, cellulose derivatives, polyethylene glycol, silicon, bentonite, and the like can be used. As the preservative, for example, methyl paraoxybenzoate, ethyl paraoxybenzoate, propyl paraoxybenzoate, and the like can be used. When preparing the pharmaceutical composition in the form of a patch, the above-mentioned ointments, creams, gels, pastes, or the like can be applied to the surface of a common support by a conventional method. As the support, for example, a woven fabric or non-woven fabric made of cotton or synthetic fibers, a film such as soft vinyl chloride, polyethylene, or polyurethane, a foaming sheet, or the like can be suitably used.

As long as the composition can be used for a desired usage, the amount of the active ingredient in the composition is not particularly limited, and can be appropriately increased or decreased depending on the age, body weight, gender, purpose of administration, symptoms, and the like of patients.

The above-mentioned active ingredient can be administered to subjects in a method for treating or preventing diseases associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes.

Biomarker

In still another embodiment, a biomarker, particularly a diagnostic marker, for evaluating diseases associated with the activities of the EGF receptor and the downstream signaling pathway thereof, such as cancer, is further provided. For example, the marker used for determining whether or not a disease associated with the activities of the EGF receptor and the downstream signaling pathway thereof, such as cancer, has developed in a subject by detecting the expression of a target nucleic acid or translation products thereof, preferably the peptide of SEQ ID NO: 4, in a sample derived from the subject or measuring the expression level thereof, or by detecting or measuring the presence of a target nucleic acid or translation products thereof, preferably a specific antibody with respect to the peptide of SEQ ID NO: 4, in the sample.

When used in the present specification, the term "subject" refers to any vertebrates including non-human primates (for example, monkeys such as crab-eating macaques, rhesus macaques, and chimpanzees), and other mammals, for example, cows, pigs, camels, llamas, horses, goats, rabbits, sheep, hamsters, guinea pigs, cats, dogs, rats, and mice). Depending on the embodiments, the subject may be a human or a non-human animal. Depending on the embodiments, the subject may be a patient at a risk of causing diseases associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes, or may be a patient in whom such a disease has already been caused.

When the biomarker is detected in the sample derived from the subject, it is possible to determine whether the disease associated with the activities of the EGF receptor and the downstream signaling pathway thereof is likely to develop, whether the disease has developed, or whether the disease has progressed. The biomarker may be a tumor marker used for diagnosing susceptibility to cancer, whether or not cancer has developed, or whether or not cancer has progressed.

The term "sample" used in the present specification broadly refers to a biological material that is thought to contain a target. Any cell, tissue, or body fluid can be utilized to obtain the sample. Such a cell, tissue, and body fluid may include sections of tissues of biopsy and autopsy samples and the like, frozen sections collected for histological purposes, blood (such as whole blood), plasma, serum, sputum, stool, tears, mucus, saliva, bronchoalveolar lavage (BAL) fluid, hair, skin, red blood cells, platelets, interstitial fluid, eye lens fluid, cerebrospinal fluid, sweat, nasal discharge, synovial fluid, vaginal discharge, amniotic fluid, semen, and the like. The cell and tissue may include lymph fluid, peritoneal fluid, gynecological fluid, urine, peritoneal cavity fluid, cerebrospinal fluid, and the like. Depending on the purposes, isolation or purification of the target peptide or the like from the sample may be performed.

The detection of the expression of the target peptide or the measurement of the expression level thereof can be implemented by immunoassays, agglutination methods, turbidimetric methods, western blot methods, surface plasmon resonance (SPR) methods, or the like, for example. Immunoassays are particularly simple and preferred.

Immunoassays are classified into enzyme immunoassay (EIA or ELISA), radioimmunoassay (RIA), fluorescent immunoassay (FIA), fluorescence polarization immunoassay (FPIA), chemiluminescence immunoassay (CLIA), and the like according to an antibody labeling method, and any of these can be used.

In the ELISA method, antibodies labeled with enzymes such as peroxidase and alkaline phosphatase are used; in the RIA method, antibodies labeled with radioactive substances such as $^{125}$I, $^{131}$I, $^{35}$S, and $^{3}$H are used; in the FPIA method, antibodies labeled with fluorescent substances such as fluorescein isothiocyanate, rhodamine, dansyl chloride, phycoerythrin, tetramethylrhodamine isothiocyanate, and near-infrared fluorescent materials are used; and in the CLIA method, antibodies labeled with luminescent substances such as luciferase, luciferin, and aequorin are used. In addition, antibodies labeled with nanoparticles such as colloidal gold and quantum dots can also be detected.

Furthermore, in the immunoassay, an antibody can be labeled with biotin, and avidin or streptavidin labeled with an enzyme or the like can be bound thereto to be detected.

Among the immunoassays, the ELISA method using enzyme labeling is preferable because an antigen can be measured easily and quickly.

For an enzyme substrate used in the ELISA method, 3,3'-diaminobenzidine (DAB), 3,3'5,5'-tetramethylbenzidine (TMB), o-phenylenediamine (OPD), or the like can be used when the enzyme is peroxidase, and p-nitropheny phosphate (NPP) or the like can be used in the case of alkaline phosphatase.

The solid phase carrier is not particularly limited as long as it is a carrier on which an antibody can be immobilized, and examples thereof include microtiter plates made of glass, metal, resin, and the like, substrates, beads, nitrocellulose membranes, nylon membranes, and PVDF membranes. A target substance can be immobilized on these solid phase carriers according to a known method.

Furthermore, in the above-mentioned immunoassays, the agglutination method is also preferable as a method for easily detecting a trace amount of protein. Examples of the agglutination method include a latex agglutination method in which latex particles are bound to an antibody.

Regarding the antibodies, both the monoclonal antibodies and the polyclonal antibodies can be produced according to a known method. The monoclonal antibodies can be obtained by isolating antibody-producing cells from a non-human mammal immunized with a target, fusing them with myeloma cells or the like to produce hybridomas, and purifying antibodies produced by the hybridomas, for example. In addition, the polyclonal antibodies can be obtained from the serum of an animal immunized with a target.

When the marker is a gene such as the LAMC2-NR6A1 gene or the LAMC2-NR6A1 splicing variant, a fluorescence in situ hybridization (FISH) method, an RT-PCR method, or other known gene mutation testing method can be used. A person skilled in the art can select appropriate means according to subject genes, and for example, the state in which the LAMC2 gene and the NR6A1 gene are bound to each other can be confirmed by the FISH method. Probes used for detection of the LAMC2-NR6A1 gene can be prepared from bacterial artificial chromosome (BAC) clones containing these genes, and for example, RP11-158D24 and RP11-582A18 can be used. When each of the probes is labeled with fluorescent dyes with different colors, the signals of the probes are detected distantly in the normal case, but detected in an overlapped manner in the case of gene binding. It is sufficient for the probe, which can be used for detection of the LAMC2-NR6A1 splicing and the like, to have a sequence that specifically recognizes a subject gene such as the LAMC2-NR6A1 splicing variant. When used in the present specification, the phrase "specifically recognizes" means binding to the specific LAMC2-NR6A1 splicing variant, but no binding to wild-type LAMC2.

From the viewpoint of providing a marker specific to cancer with higher sensitivity, it is preferable to target the peptide of SEQ ID NO: 4 or the base sequence of SEQ ID NO: 5 encoding the same.

Detection Method

In still another embodiment, a method for detecting the biomarker of the disease associated with the activities of the EGF receptor and the downstream signaling pathway thereof is provided. The detection method includes any of the following (a) to (e):

(a) the LAMC2-NR6A1 splicing variant, preferably the splicing variant having the base sequence of SEQ ID NO: 2 or 6;

(b) the protein encoded by the LAMC2-NR6A1 splicing variant, preferably the splicing variant having the base sequence of SEQ ID NO: 2 or 6;

(c) the peptide having the amino acid sequence of SEQ ID NO: 4;

(d) the nucleic acid encoding the peptide of (c) or the nucleic acid complementary thereto; and (e) the antibody against the protein of (b) or the peptide of (c).

A detection target is not limited to the above-mentioned (a) to (e), and may be any one that can imply the presence of the LAMC2-NR6A1 splicing variant or the translation products thereof. The detection of the presence of the fusion gene is known to a person skilled in the art, and identification can be easily performed using a next-generation sequencer or the like. The same applies to the LAMC2-NR6A1 splicing variant. For example, it is determined that a subject has the LAMC2-NR6A1 splicing variant when the read sequence of genomic DNA obtained from a sample derived from the subject is mapped to the standard sequence of the LAMC2 gene (or the NR6A1 gene), and the unmapped portion is derived from the NR6A1 gene (LAMC2 gene when the mapped sequence is of the NR6A1 gene).

The detection method may further include a step of determining whether the disease associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes, is likely to develop, whether the disease has developed, or whether the disease has progressed when the biomarker is detected or present in a high concentration as compared to a healthy individual. For example, it is determined that a subject has the disease associated with the activities of the EGF receptor and the downstream signaling pathway thereof when the read sequence of genomic DNA obtained from a sample derived from the subject in whom the development of the disease associated with the activities of the EGF receptor and the downstream signaling pathway thereof is suspected is mapped to the standard sequence of the LAMC2 gene (or the NR6A1 gene), and the unmapped portion is derived from the NR6A1 gene (LAMC2 gene when the mapped sequence is of the NR6A1 gene).

The biomarker may be a tumor marker used for diagnosing susceptibility to cancer, whether or not cancer has developed, or whether or not cancer has progressed. The step of determining whether the disease associated with the activities of the EGF receptor and the downstream signaling pathway thereof is likely to develop, whether the disease has developed, or whether the disease has progressed can be performed with assistance by clinical laboratory technicians and medical instruments.

The detection method can be suitably used for a method for diagnosing the diseases associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes, particularly cancer. When used in the diagnosis of cancer, the detection method may optionally include a step of determining that a subject has cancer, a step of determining the degree of severity of cancer, a step of determining a risk of causing cancer in the subject (that is, a likelihood of onset of the disease), a step of determining the efficacy of a cancer treatment regimen, a step of identifying the subject as a candidate for a cancer treatment method, and a step of evaluating a risk relating to the progression of the disease in the subject having cancer.

Screening Method

In still another embodiment, a method for screening a medicine for treating or preventing diseases associated with the activities of the EGF receptor and the downstream signaling pathway thereof, such as cancer, obesity, autoimmune diseases, inflammation, heart diseases, particularly heart diseases accompanied by cardiomyocyte hypertrophy, neurodegenerative diseases, or diabetes is provided. The screening method may optionally include a step of selecting, as the medicine, a substance inhibiting the expression of the LAMC2-NR6A1 gene, and the LAMC2-NR6A1 splicing variant or the translation products thereof, particularly the peptide of SEQ ID NO: 4.

Treatment or Prevention Method

In still another embodiment, a method for treating or preventing the disease associated with the activities of the EGF receptor and the downstream signaling pathway thereof in a subject is provided, the method including administering, to the subject, a compound or a salt thereof which inhibits the expression of the LAMC2-NR6A1 gene, and the LAMC2-NR6A1 splicing variant or the translation products thereof, particularly the peptide of SEQ ID NO: 4. The disease associated with the activities of the EGF receptor and the downstream signaling pathway thereof is not particularly limited, but examples thereof include cancer, obesity, autoimmune diseases, inflammation, heart diseases, neurodegenerative diseases, or diabetes.

Hereinafter, the present invention will be described in more detail with reference to examples and comparative examples, but the present invention is not limited thereto.

EXAMPLES (Identification of Novel Fusion Gene)

As a result of performing Whole genome sequence using the genome of an ovarian cancer cell line Skov3, gene binding between LAMC2 and NR6A1 at the chromosomal level was found (SEQ ID NO: 1). Subsequently, the chromosomal-level gene binding in Skov3 cells was confirmed by the FISH method. First, colcemid was added to Skov3 cells purchased from the JCRB cell bank, and thereafter, the cells were cultured for 2 hours, and recovered by trypsin. The recovered cells were fixed with a fixing solution of methanol:acetic acid=3:1. The fixed cells were spread on a slide glass to make a prepared slide for FISH. Using a commercially available BAC clone, a probe was created on the centromere side of LAMC2 and the telomere side of NR6A1 (LAMC2: BAC clone RP11-158D24; NR6A1: BAC clone RP11-582A18, respectively).

The probe on the centromere side of LAMC2 was labeled with digoxigenin (red), and the probe on the telomere side of NR6A1 was labeled with biotin (green). These probes were applied to the Skov3 cells, and sections and the probes were metamorphosed at the same time for 5 minutes on a hot plate at 70° C. to be hybridized overnight at 37° C. The hybridized sections were stringently washed with 50% formamide/2×SSC and 1×SSC at 37° C. They were counterstained with (4',6-diamidino-2-phenylindole (DAPI), and mounted with an anti-fading agent.

Figure 1:
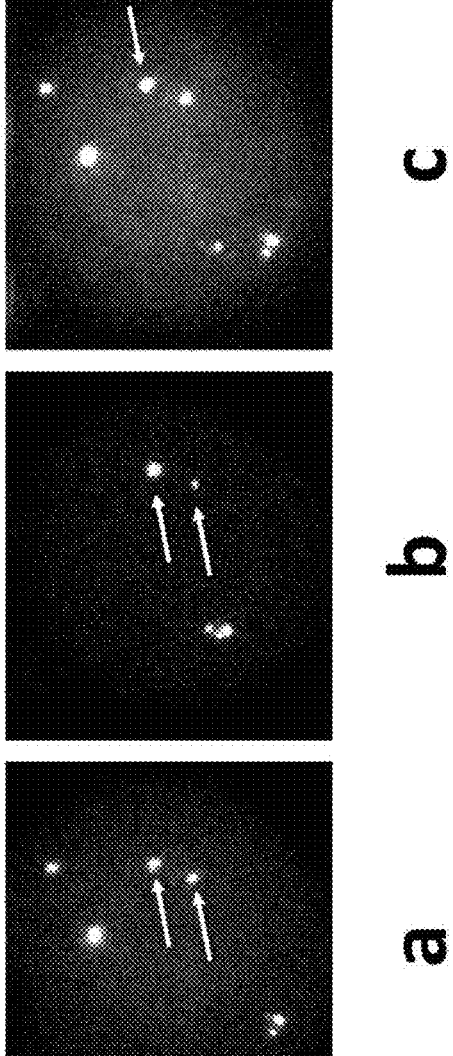
FIG. 1 shows the results of confirming chromosomal-level gene binding in Skov3 cells by a FISH method. A red color signal (for example, the signal shown in FIG. 1a) is one derived from a probe on the centromere side of LAMC2, a green color signal (for example, the signal shown in FIG. 1b) is one derived from a probe on the telomere side of NR6A1, and a yellow color signal (the signal indicated by the arrow on FIG. 1c) indicates that LAMC2 and NR6A1 are bound to each other.

For the detection of probe signals and the analysis of the data, images were captured and the FISH data was analyzed by a LEICA CW-4000 cytogenetic workstation. 40× and 20× objective lenses were used for imaging. The results are shown in FIG. 1.

Figure 16:
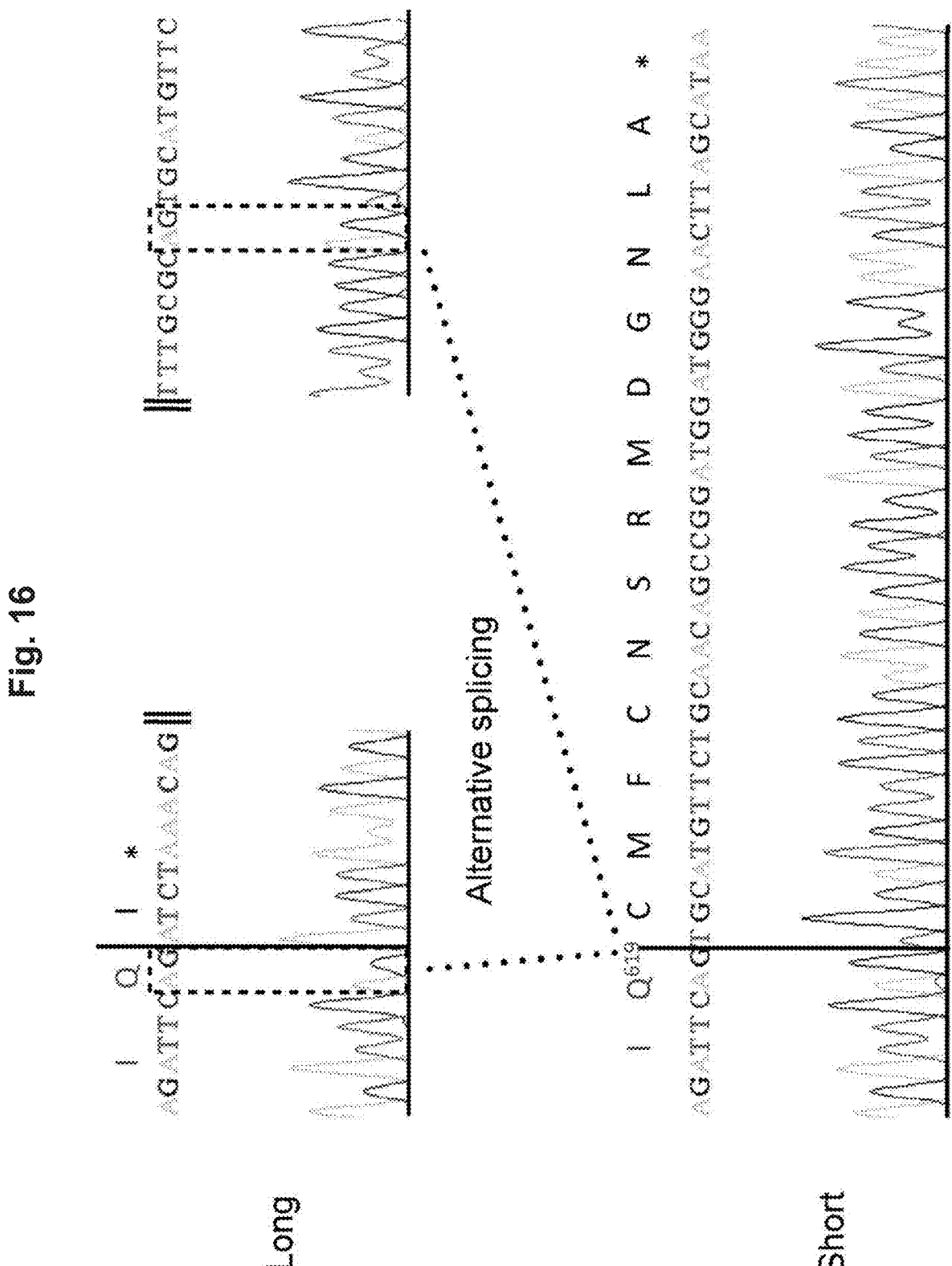
FIG. 16 shows the results of determining the sequences of SHORT FORM and LONG FORM (Ln-γ2F).

A novel splicing variant in which the LAMC2 and NR6A1 genes are bound to each other was identified from the ovarian cancer cultured cell line (Skov3) by a RACE-PCR method. The full-length base sequence of SHORT FORM, which is one of the splicing variants of the present invention, and the amino acid sequence encoded thereby are represented as SEQ ID NO: 2 and SEQ ID NO: 3, respectively. The results of determining the SHORT and LONG sequences are shown in FIG. 16.

20

SEQ ID NO: 2:
ATGCCTGCGCTCTGGCTGGGCTGCTGCCTCTGCTTCTCGCTCCTCCTGC

CCGCAGCCCGGGCCACCTCCAGGAGGGAAGTCTGTGATTGCAATGGGAA

GTCCAGGCAGTGTATCTTTGATCGGGAACTTCACAGACAAACTGGTAAT

GGATTCCGCTGCCTCAACTGCAATGACAACACTGATGGCATTCACTGCG

AGAAGTGCAAGAATGGCTTTTACCGGCACAGAGAAAGGGACCGCTGTTT

GCCCTGCAATTGTAACTCCAAAGGTTCTCTTAGTGCTCGATGTGACAAC

TCTGGACGGTGCAGCTGTAAACCAGGTGTGACAGGAGCCAGATGCGACC

GATGTCTGCCAGGCTTCCACATGCTCACGGATGCGGGGTGCACCCAAGA

CCAGAGACTGCTAGACTCCAAGTGTGACTGTGACCCAGCTGGCATCGCA

GGGCCCTGTGACGCGGGCCGCTGTGTCTGCAAGCCAGCTGTTACTGGAG

AACGCTGTGATAGGTGTCGATCAGGTTACTATAATCTGGATGGGGGGAA

CCCTGAGGGCTGTACCCAGTGTTTCTGCTATGGGCATTCAGCCAGCTGC

CGCAGCTCTGCAGAATACAGTGTCCATAAGATCACCTCTACCTTTCATC

AAGATGTTGATGGCTGGAAGGCTGTCCAACGAAATGGGTCTCCTGCAAA

GCTCCAATGGTCACAGCGCCATCAAGATGTGTTTAGCTCAGCCCAACGA

CTAGACCCTGTCTATTTTGTGGCTCCTGCCAAATTTCTTGGGAATCAAC

AGGTGAGCTATGGGCAAAGCCTGTCCTTTGACTACCGTGTGGACAGAGG

AGGCAGACACCCATCTGCCCATGATGTGATTCTGGAAGGTGCTGGTCTA

CGGATCACAGCTCCCTTGATGCCACTTGGCAAGACACTGCCTTGTGGGC

TCACCAAGACTTACACATTCAGGTTAAATGAGCATCCAAGCAATAATTG

GAGCCCCCAGCTGAGTTACTTTGAGTATCGAAGGTTACTGCGGAATCTC

ACAGCCCTCCGCATCCGAGCTACATATGGAGAATACAGTACTGGGTACA

TTGACAATGTGACCCTGATTTCAGCCCGCCCTGTCTCTGGAGCCCCAGC

ACCCTGGGTTGAACAGTGTATATGTCCTGTTGGGTACAAGGGGCAATTC

TGCCAGGATTGTGCTTCTGGCTACAAGAGAGATTCAGCGAGACTGGGGC

CTTTTGGCACCTGTATTCCTTGTAACTGTCAAGGGGGAGGGGCCTGTGA

TCCAGACACAGGAGATTGTTATTCAGGGGATGAGAATCCTGACATTGAG

TGTGCTGACTGCCCAATTGGTTTCTACAACGATCCGCACGACCCCCGCA

GCTGCAAGCCATGTCCCTGTCATAACGGGTTCAGCTGCTCAGTGATGCC

GGAGACGGAGGAGGTGGTGTGCAATAACTGCCCTCCCGGGGTCACCGGT

GCCCGCTGTGAGCTCTGTGCTGATGGCTACTTTGGGGACCCCTTTGGTG

AACATGGCCCAGTGAGGCCTTGTCAGCCCTGTCAATGCAACAACAATGT

GGACCCCAGTGCCTCTGGGAATTGTGACCGGCTGACAGGCAGGTGTTTG

AAGTGTATCCACAACACAGCCGGCATCTACTGCGACCAGTGCAAAGCAG

GCTACTTCGGGGACCCATTGGCTCCCAACCCAGCAGACAAGTGTCGAGC

TTGCAACTGTAACCCCATGGGCTCAGAGCCTGTAGGATGTCGAAGTGAT

GGCACCTGTGTTTGCAAGCCAGGATTTGGTGGCCCCAACTGTGAGCATG

GAGCATTCAGCTGTCCAGCTTGCTATAATCAAGTGAAGATTCAGtgcat gttctgcaacagccggatggatgggaacttagcataatctcaaagagca accctgatgctcccataacagcaggacctcaacgtccaagaagaatacc -continued

```
acaccttacttgagcccatttacaagtcacctcctgaaaaatccaagat gcctgtcagaagcagctactgagggaagtgaagatgtttttatttgttc attgtcattgtgaagactgactaaagtcttactgatcaaggagtttgtt tgaacatggtcagagagctttcaaagtcatttcagaaagtgccccacac catcctcaacagatggtttgatggaagagaagtagccagctctgctcag gaaatccattagtaaggtgcagataccaccaaagagatgtcccacatgt ggcagaatgtacctttttccttattttctttaaaatctccatataaaaa gggaagatggatgcatgagggcctagaaaatgtttatccctctggatca atcttaggaatctatcctaagaatcagaaatacagaaaatagtacaaaa ctcgaggccatctaaaaattcaaacacaggaaaatgattaaattatgta cacttattcaatggaatattttgcgaacactataaatgttttccaagag tttacaaagggcaaataccatattaaaaatacaatgtaaaactgg
```

(Note: Uppercase letters represent the sequence derived from the sense strand of LAMC2, lowercase letters represent the sequence derived from the antisense strand of NR6A1, and the underlined part represents the sequence common to SHORT FORM and LONG FORM)

```
SEQ ID NO: 3:
MPALWLGCCLCFSLLLPAARATSRREVCDCNGKSRQCIFDRELHRQTGN

GFRCLNCNDNTDGIHCEKCKNGFYRHRERDRCLPCNCNSKGSLSARCDN

SGRCSCKPGVTGARCDRCLPGFHMLTDAGCTQDQRLLDSKCDCDPAGIA

GPCDAGRCVCKPAVTGERCDRCRSGYYNLDGGNPEGCTQCFCYGHSASC

RSSAEYSVHKITSTFHQDVDGWKAVQRNGSPAKLQWSQRHQDVFSSAQR

LDPVYFVAPAKFLGNQQVSYGQSLSFDYRVDRGGRHPSAHDVILEGAGL

RITAPLMPLGKTLPCGLTKTYTFRLNEHPSNNWSPQLSYFEYRRLLRNL

TALRIRATYGEYSTGYIDNVTLISARPVSGAPAPWVEQCICPVGYKGQF

CQDCASGYKRDSARLGPFGTCIPCNCQGGGACDPDTGDCYSGDENPDIE

CADCPIGFYNDPHDPRSCKPCPCHNGFSCSVMPETEEVVCNNCPPGVTG

ARCELCADGYFGDPFGEHGPVRPCQPCQCNNNVDPSASGNCDRLTGRCL

KCIHNTAGIYCDQCKAGYFGDPLAPNPADKCRACNCNPMGSEPVGCRSD

GTCVCKPGFGGPNCEHGAFSCPACYNQVKIQCMFCNSRMDGNLA*
```

(Note: The underlined part represents a novel peptide obtained by binding of LAMC2 and NR6A1, and * represents a stop codon (taa))

The amino acid sequence encoding the LAMC2-NR6A1 peptide (CMFCNSRMDGNLA) was designated as SEQ ID NO: 4, and the base sequence encoding the same (tg-catgttctgcaacagccggatggatgggaacttagca) was designated as SEQ ID NO: 5.

The full-length base sequence of LONG FORM identified by the same procedure as SHORT FORM, and the amino acid sequence encoded thereby are described below as SEQ ID NO: 6 and SEQ ID NO: 7, respectively.

```
SEQ ID NO: 6:
ATGCCTGCGCTCTGGCTGGGCTGCTGCCTCTGCTTCTCGCTCCTCCTGC

CCGCAGCCCGGGCCACCTCCAGGAGGGAAGTCTGTGATTGCAATGGGAA
```

-continued

```
GTCCAGGCAGTGTATCTTTGATCGGGAACTTCACAGACAAACTGGTAAT

GGATTCCGCTGCCTCAACTGCAATGACAACACTGATGGCATTCACTGCG

AGAAGTGCAAGAATGGCTTTTACCGGCACAGAGAAAGGGACCGCTGTTT

GCCCTGCAATTGTAACTCCAAAGGTTCTCTTAGTGCTCGATGTGACAAC

TCTGGACGGTGCAGCTGTAAACCAGGTGTGACAGGAGCCAGATGCGACC

GATGTCTGCCAGGCTTCCACATGCTCACGGATGCGGGGTGCACCCAAGA

CCAGAGACTGCTAGACTCCAAGTGTGACTGTGACCCAGCTGGCATCGCA

GGGCCCTGTGACGCGGGCCGCTGTGTCTGCAAGCCAGCTGTTACTGGAG

AACGCTGTGATAGGTGTCGATCAGGTTACTATAATCTGGATGGGGGGAA

CCCTGAGGGCTGTACCCAGTGTTTCTGCTATGGGCATTCAGCCAGCTGC

CGCAGCTCTGCAGAATACAGTGTCCATAAGATCACCTCTACCTTTCATC

AAGATGTTGATGGCTGGAAGGCTGTCCAACGAAATGGGTCTCCTGCAAA

GCTCCAATGGTCACAGCGCCATCAAGATGTGTTTAGCTCAGCCCAACGA

CTAGACCCTGTCTATTTTGTGGCTCCTGCCAAATTTCTTGGGAATCAAC

AGGTGAGCTATGGGCAAAGCCTGTCCTTTGACTACCGTGTGGACAGAGG

AGGCAGACACCCATCTGCCCATGATGTGATTCTGGAAGGTGCTGGTCTA

CGGATCACAGCTCCCTTGATGCCACTTGGCAAGACACTGCCTTGTGGGC

TCACCAAGACTTACACATTCAGGTTAAATGAGCATCCAAGCAATAATTG

GAGCCCCCAGCTGAGTTACTTTGAGTATCGAAGGTTACTGCGGAATCTC

ACAGCCCTCCGCATCCGAGCTACATATGGAGAATACAGTACTGGGTACA

TTGACAATGTGACCCTGATTTCAGCCCGCCCTGTCTCTGGAGCCCCAGC

ACCCTGGGTTGAACAGTGTATATGTCCTGTTGGGTACAAGGGGCAATTC

TGCCAGGATTGTGCTTCTGGCTACAAGAGAGATTCAGCGAGACTGGGGC

CTTTTGGCACCTGTATTCCTTGTAACTGTCAAGGGGGAGGGGCCTGTGA

TCCAGACACAGGAGATTGTTATTCAGGGGATGAGAATCCTGACATTGAG

TGTGCTGACTGCCCAATTGGTTTCTACAACGATCCGCACGACCCCCGCA

GCTGCAAGCCATGTCCCTGTCATAACGGGTTCAGCTGCTCAGTGATGCC

GGAGACGGAGGAGGTGGTGTGCAATAACTGCCCTCCCGGGGTCACCGGT

GCCCGCTGTGAGCTCTGTGCTGATGGCTACTTTGGGGACCCCTTTGGTG

AACATGGCCCAGTGAGGCCTTGTCAGCCCTGTCAATGCAACAACAATGT

GGACCCCAGTGCCTCTGGGAATTGTGACCGGCTGACAGGCAGGTGTTTG

AAGTGTATCCACAACACAGCCGGCATCTACTGCGACCAGTGCAAAGCAG

GCTACTTCGGGGACCCATTGGCTCCCAACCCAGCAGACAAGTGTCGAGC

TTGCAACTGTAACCCCATGGGCTCAGAGCCTGTAGGATGTCGAAGTGAT

GGCACCTGTGTTTGCAAGCCAGGATTTGGTGGCCCCAACTGTGAGCATG

GAGCATTCAGCTGTCCAGCTTGCTATAATCAAGTGAAGATTCAGatcta aacagatcattgtactccattacatggaaagagccacaaaagtcaaaac aagagaacttctattgaaagcatcttgactaataaaaccctacctttgc gcagtgcatgttctgcaacagccggatggatgggaacttagcataatct caaagagcaaccctgatgctcccataacagcaggacctcaacgtccaag
```

-continued

```
aagaataccacaccttacttgagcccatttacaagtcacctcctgaaaa atccaagatgcctgtcagaagcagctactgagggaagtgaagatgtttt tatttgttcattgtcattgtgaagactgactaaagtcttactgatcaag gagtttgtttgaacatggtcagagagctttcaaagtcatttcagaaagt gccccacaccatcctcaacagatggtttgatggaagagaagtagccagc tctgctcaggaaatccattagtaaggtgcagataccaccaaagagatgt cccacatgtggcagaatgtacctttttccttattttctttaaaatctcc atataaaaagggaagatggatgcatgagggcctagaaaatgtttatccc tctggatcaatcttaggaatctatcctaagaatcagaaatacagaaaat agtacaaaactcgaggccatctaaaaattcaaacacaggaaatgatta aattatgtacacttattcaatggaatattttgcgaacactataaatgtt ttccaagagtttacaaagggcaaataccatattaaaaatacaatgtaaa actgg
```

(Note: Uppercase letters represent the sequence derived from the sense strand of LAMC2, lowercase letters represent the sequence derived from the antisense strand of NR6A1, and the underlined part represents the sequence common to SHORT FORM and LONG FORM)

```
SEQ ID NO: 7:
MPALWLGCCLCFSLLLPAARATSRREVCDCNGKSRQCIFDRELHRQTGN

GFRCLNCNDNTDGIHCEKCKNGFYRHRERDRCLPCNCNSKGSLSARCDN

SGRCSCKPGVTGARCDRCLPGFHMLTDAGCTQDQRLLDSKCDCDPAGIA

GPCDAGRCVCKPAVTGERCDRCRSGYYNLDGGNPEGCTQCFCYGHSASC

RSSAEYSVHKITSTFHQDVDGWKAVQRNGSPAKLQWSQRHQDVFSSAQR

LDPVYFVAPAKFLGNQQVSYGQSLSFDYRVDRGGRHPSAHDVILEGAGL

RITAPLMPLGKTLPCGLTKTYTFRLNEHPSNNWSPQLSYFEYRRLLRNL

TALRIRATYGEYSTGYIDNVTLISARPVSGAPAPWVEQCICPVGYKGQF

CQDCASGYKRDSARLGPFGTCIPCNCQGGGACDPDTGDCYSGDENPDIE

CADCPIGFYNDPHDPRSCKPCPCHNGFSCSVMPETEEVVCNNCPPGVTG

ARCELCADGYFGDPFGEHGPVRPCQPCQCNNNVDPSASGNCDRLTGRCL

KCIHNTAGIYCDQCKAGYFGDPLAPNPADKCRACNCNPMGSEPVGCRSD

GTCVCKPGFGGPNCEHGAFSCPACYNQVKIQI*
```

(Note: The underlined part represents a novel peptide obtained by binding of LAMC2 and NR6A1, and * represents a stop codon (taa))

Whether or not the LAMC2-NR6A1 splicing variant of SHORT FORM was expressed in normal cells was confirmed by using an RT-PCR method. Human normal tissue cDNA used in the present RT-PCR method was purchased from Filgen, Inc. For positive control, cDNA prepared from Skov3 cells was used. For the LAMC2 wild type, an LAMC2 sequence-derived primer was used. For the detection of the LAMC2-NR6A1 splicing variant of SHORT FORM, the LAMC2 sequence-derived primer and an NR6A1 sequence-derived primer were used to detect only the LAMC2-NR6A1 splicing variant of SHORT FORM. In addition, GAPDH was used as an endogenous control. The primers used are listed below.

```
GAPDH-sense:
                                (SEQ ID NO: 8)
aaggctgagaacgggaagcttgtcatcaat GAPDH-anti sense:
                                (SEQ ID NO: 9)
ttcccgtctagctcagggatgaccttgccc LAMC2-WT sense:
                                (SEQ ID NO: 10)
gctacttcggggacccattg LAMC2-WT antisense:
                                (SEQ ID NO: 11)
caagctggacagctgaatgc LAMC2-NR6A1 sense:
                                (SEQ ID NO: 12)
accagtgcaaagcaggctac LAMC2-NR6A1 antisense:
                                (SEQ ID NO: 13)
tcagggttgctctttgaga
```

Figure 4:
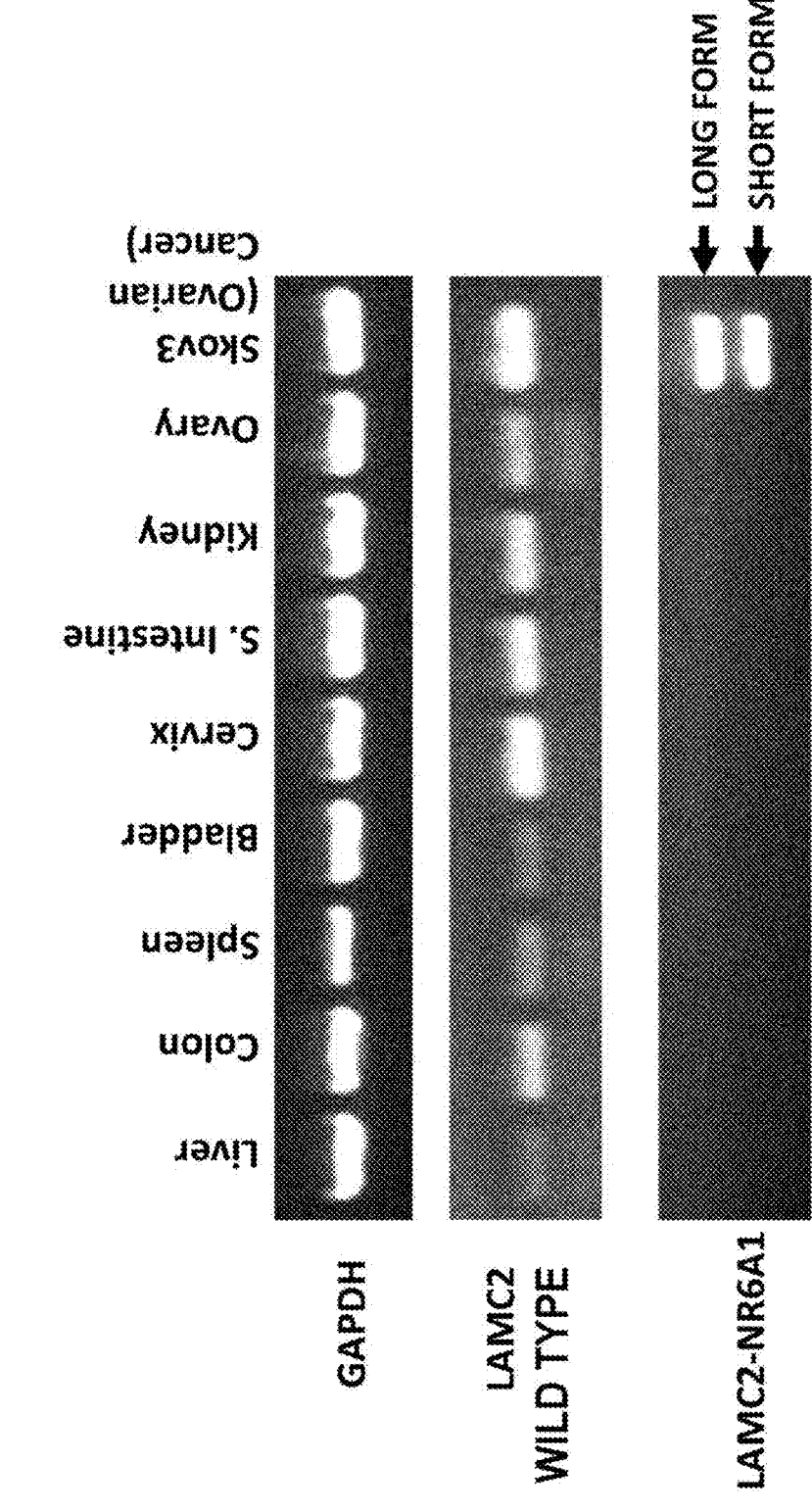
FIG. 4 shows the results of examining, by PCR, the expression distribution of the LAMC2-NR6A1 splicing variants of LONG FORM and SHORT FORM in normal cells. Based on these results, it can be seen that the LAMC2-NR6A1 splicing variants of LONG FORM and SHORT FORM are not expressed in normal cells.

The results are shown in FIG. 4.

As shown in FIG. 4, although there were variations among the tissues, the LAMC2 wild type was expressed in all the tissues. However, the LAMC2-NR6A1 splicing variant of SHORT FORM was expressed only in the Skov3 cells. Based on this, it became clear that the LAMC2-NR6A1 splicing variant of SHORT FORM is specific to cancer cells.

Subsequently, when it was confirmed by the PCR method what kind of cancer type the LAMC2-NR6A1 splicing variant of SHORT FORM was present in, the LAMC2-NR6A1 splicing variant of SHORT FORM was detected in liver cancer, breast cancer, ovarian cancer, and many other cancer types. It was highly expressed particularly in the cell line containing PI3K mutation and the line deficient in PTEN (PI3K mutant and cell phenotype in terms of increasing PI3, 4, 5P3) (results not shown).

Figure 5:
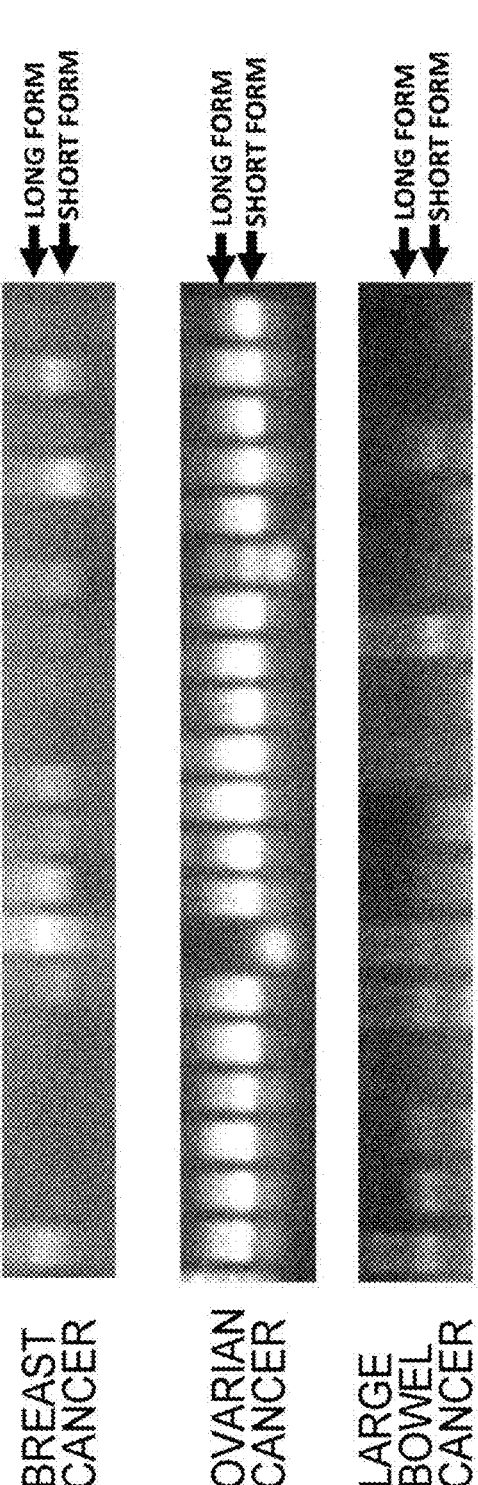
FIG. 5 shows the results of detecting the expression of the LAMC2-NR6A1 splicing variants of LONG FORM and SHORT FORM in clinical specimens derived from cancer patients. As a result of detecting the LAMC2-NR6A1 splicing variants by PCR using cancer tissues derived from patients with breast cancer, ovarian cancer, and large bowel cancer, the LAMC2-NR6A1 splicing variant of SHORT FORM was detected in 19 specimens out of 20 specimens for ovarian cancer, 13 specimens out of 19 specimens for breast cancer, and 11 specimens out of 16 specimens for large bowel cancer. Meanwhile, the splicing variant of LONG FORM was detected in 12 specimens out of 20 specimens for ovarian cancer.

Next, whether or not the LAMC2-NR6A1 splicing variant of SHORT FORM was actually present in cancer patients was investigated by RT-PCT. cDNA was prepared from a patient having a predetermined cancer using the tissue at the time of surgery, and the LAMC2-NR6A1 splicing variant of SHORT FORM was detected by the PCR method. As a result, the LAMC2-NR6A1 splicing variant of SHORT FORM was detected in 19 specimens out of 20 specimens for ovarian cancer, 13 specimens out of 19 specimens for breast cancer, and 11 specimens out of 16 specimens for large bowel cancer (FIG. 5).

(Analysis of Function of LAMC2-NR6A1 Splicing Variant of SHORT FORM)

To examine the role of the LAMC2-NR6A1 splicing variant of SHORT FORM in cancer cells, a plurality of cancer cell lines were created. First, using lentiviruses, the LAMC2-NR6A1 splicing variant of SHORT FORM was gene-introduced into the ovarian cancer cell line OVCAR8 not expressing the LAMC2-NR6A1 splicing variant of SHORT FORM to establish a cell line that stably expresses the LAMC2-NR6A1 splicing variant of SHORT FORM. A cell line was established by the same method except that the LAMC2-NR6A1 splicing variant of SHORT FORM was replaced with the LAMC2 wild-type gene. Furthermore, using the ovarian cancer cell line Skov3 expressing the LAMC2-NR6A1 splicing variant of SHORT FORM, two types of shRNA was introduced thereto with a lentivirus to establish a cell line in which the expression of LAMC2 was stably suppressed. The sequence of shRNA used is shown below.

```
shRNA-1:
                            (SEQ ID NO: 14)
ctgccaaatttcttgggaatc shRNA-2:
                            (SEQ ID NO: 15)
gccctgtcaatgcaacaacaa
```

Figure 6:
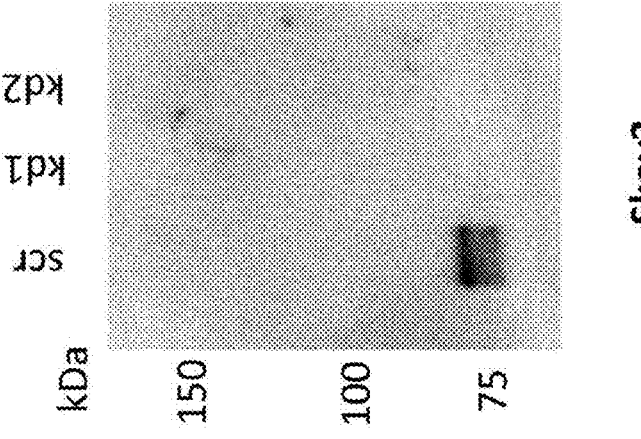
FIG. 6 shows the results of functional analysis of Ln-γ2F in an ovarian cancer cell line Ovcar8 to which the Ln-γ2F (LAMC2-NR6A1 splicing variant of SHORT FORM) was introduced, and an ovarian cancer cell Skov3 expressing the Ln-γ2F.
Figure 6:
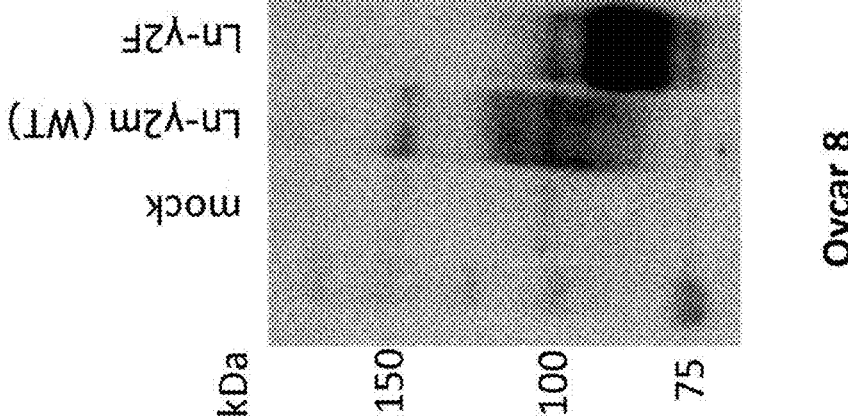

Cell extraction liquids were prepared from each of the cell lines to perform a western blot using an anti-LAMC2 antibody (D4B5, Millipore). The results are shown in FIG. 6. An LAMC2 protein was detected at about 150 kDa. It can be inferred from the amino acid sequence that the LAMC2-NR6A1 splicing variant of SHORT FORM is detected at about 80 kDa. In the Ovcar8 cells not expressing the LAMC2-NR6A1 splicing variant of SHORT FORM, the endogenous LAMC2 protein was detected at about 150 kDa in the cell line (mock) into which a control vector was introduced. In the cell line (WT) into which the LAMC2 wild type was introduced, the band was increased by about 150 kDa, and in the cell line (LAMC2-NR6A1) into which the LAMC2-NR6A1 splicing variant of SHORT FORM was introduced, the band was detected at about 80 kDa. On the other hand, in the western blot analysis using the cell extraction liquid of Skov3 expressing the LAMC2-NR6A1 splicing variant of SHORT FORM, the LAMC2-NR6A1 splicing variant product of SHORT FORM was detected at about 80 kDa in the control cells (scr), and when the expression was suppressed by shRNA, the band of about 80 kDa disappeared (kd1 and kd2). Skov3 was expressed at the mRNA level in both the LAMC2 wild type and the LAMC2-NR6A1 splicing variant of SHORT FORM, but only the translation products of the LAMC2-NR6A1 splicing variant of SHORT FORM were detected at the protein level.
(Influence on Intracellular Signal)

Figure 7:
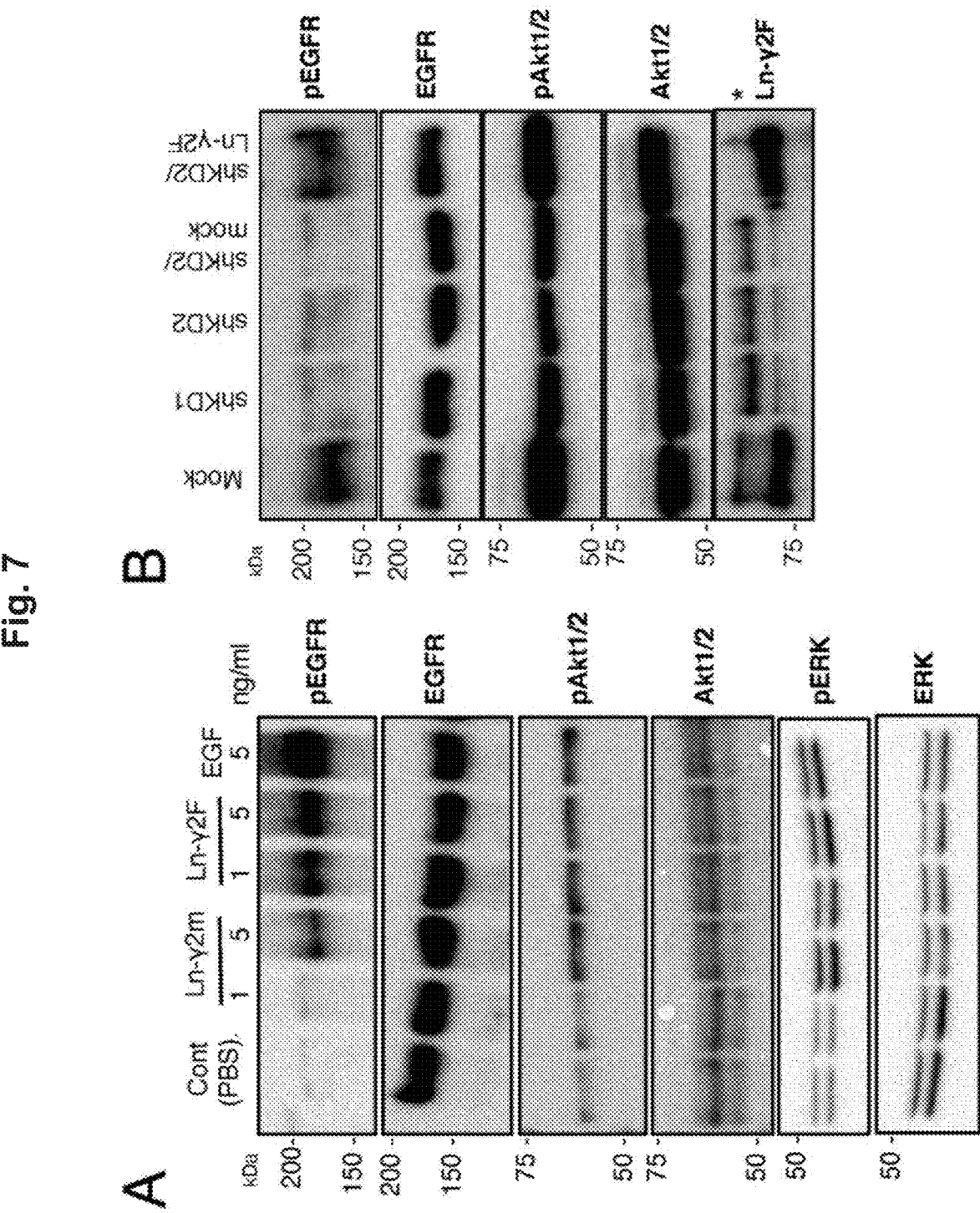
FIG. 7 shows the results of performing a western blot using an anti-ERK antibody, an anti-phospho-ERK antibody, an anti-Akt antibody, an anti-phospho-Akt antibody, an anti-EGFR antibody, and an anti-phospho-EGFR antibody to examine the influence of Ln-γ2F on intracellular signaling. In the drawing, Ln-γ2F means a fusion gene product, and Ln-γ2m means a laminin γ2 single chain. An asterisk (*) indicates a non-specific band.

In order to clarify whether or not the LAMC2-NR6A1 splicing variant of SHORT FORM affects intracellular signals, the SKOV-3 cells were caused to be in the serum starvation state under 0.5% serum culture, and a laminin γ2 single chain (Ln-γ2m) and the LAMC2-NR6A1 splicing variant of SHORT FORM (LAMC2 fusion protein (Ln-γ2F)) were added thereto to 1.5 μg/mL. Thereafter, the expression and the phosphorylation of EGFR, AKT, and ERK in cell lysates were investigated using an anti-ERK antibody, an anti-phospho-ERK antibody, an anti-Akt antibody, an anti-phospho-Akt antibody, an anti-EGFR antibody, and an anti-phospho-EGFR antibody (manufactured by Cell Signaling Technology, Inc.). The results are shown in FIG. 7A. Ln-γ2F induced the phosphorylation of EGFR as in the case of EGF of positive control. Furthermore, it became clear that Ln-γ2F induces the phosphorylation of EGFR at a concentration lower than that of Ln-γ2m. Similarly, since the induction of the phosphorylation of AKT and ERK of EGFR downstream signals was confirmed from Ln-γ2F, Ln-γ2F contributes to the activation of EGFR and the downstream signals thereof as in the case of Ln-γ2m. A western blot was performed using an anti-ERK antibody, an anti-phospho-ERK antibody, an anti-Akt antibody, an anti-phospho-Akt antibody, an anti-EGFR antibody, and an anti-phospho-EGFR antibody (manufactured by Cell Signaling Technology, Inc.).

Subsequently, SKOV-3 was cultured under normal serum containing 10% FCS to examine the expression and the phosphorylation of EGFR and AKT using cells (shKD1, shKD2) in which the expression of Ln-γ2F expressed in SKOV-3 was knocked down, and cells in which mock and Ln-γ2F were returned to shKD2 cells. The results are shown in FIG. 7B. In the condition containing serum, the activity of EGFR by endogenously produced Ln-γ2F was observed, but the expression of Ln-γ2F and the phosphorylation of EGFR disappeared (top panel) in the shKD1 and shKD2 (bottom panel) cells. On the other hand, in the revertant cells expressing Ln-γ2F in the shKD2 cells, induction of the phosphorylation of EGFR and AKT was observed. Based on the above description, it became clear that Ln-γ2F induces the phosphorylation of EGFR more efficiently than Ln-γ2m, and contributes to the activation of downstream ERK and AKT signals.

Figure 8:
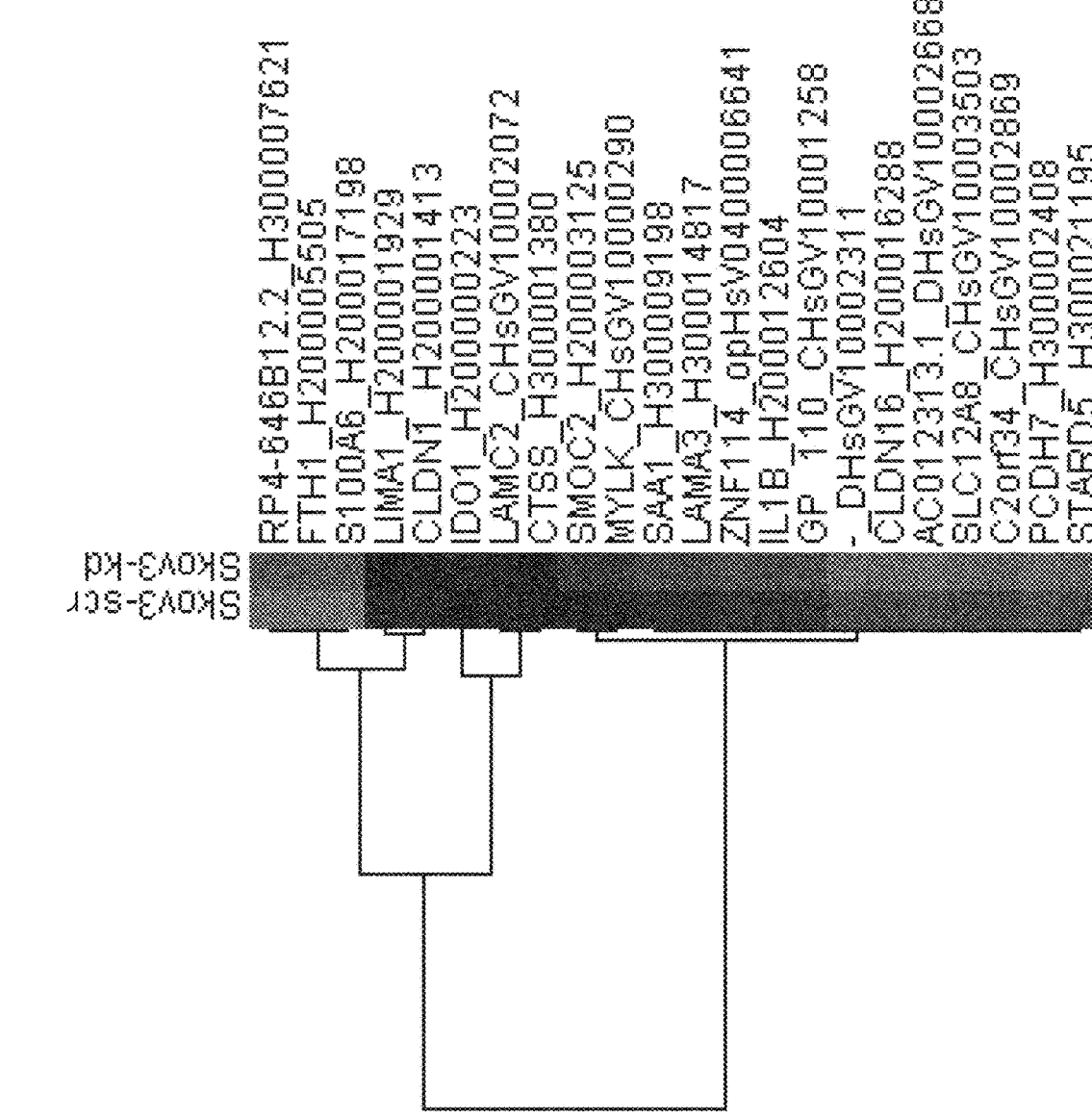
FIG. 8 shows the results of microarray analysis of Skov3-scr and Skov3-kd1. When the gene expression patterns of cells in which Ln-γ2F expression was suppressed and control cells were compared by microarray analysis, the expression of a gene cluster controlled by Akt was decreased.

Here, it is known that Akt and ERK are central to signal transduction networks that affect a wide range, and Akt activation acts as a master switch for these cellular signal transduction pathways to cause various intracellular reactions via a wide range of downstream target molecules and interacting molecules. It became clear that the activation of Akt and ERK is also enhanced in many cancer types. To investigate whether or not the activation of Akt and ERK controlled by the LAMC2 fusion protein (Ln-γ2F) identified by us is sufficient to control downstream gene expression, the gene expression patterns of Skov3-scr and Skov3-kd1 were examined by a microarray method. The results are shown in FIG. 8. Although various gene expression patterns were different, the expression of a gene cluster of which the expression is known to be controlled by Akt was particularly reduced.
(Influence on Cell Proliferation)

Figure 9:
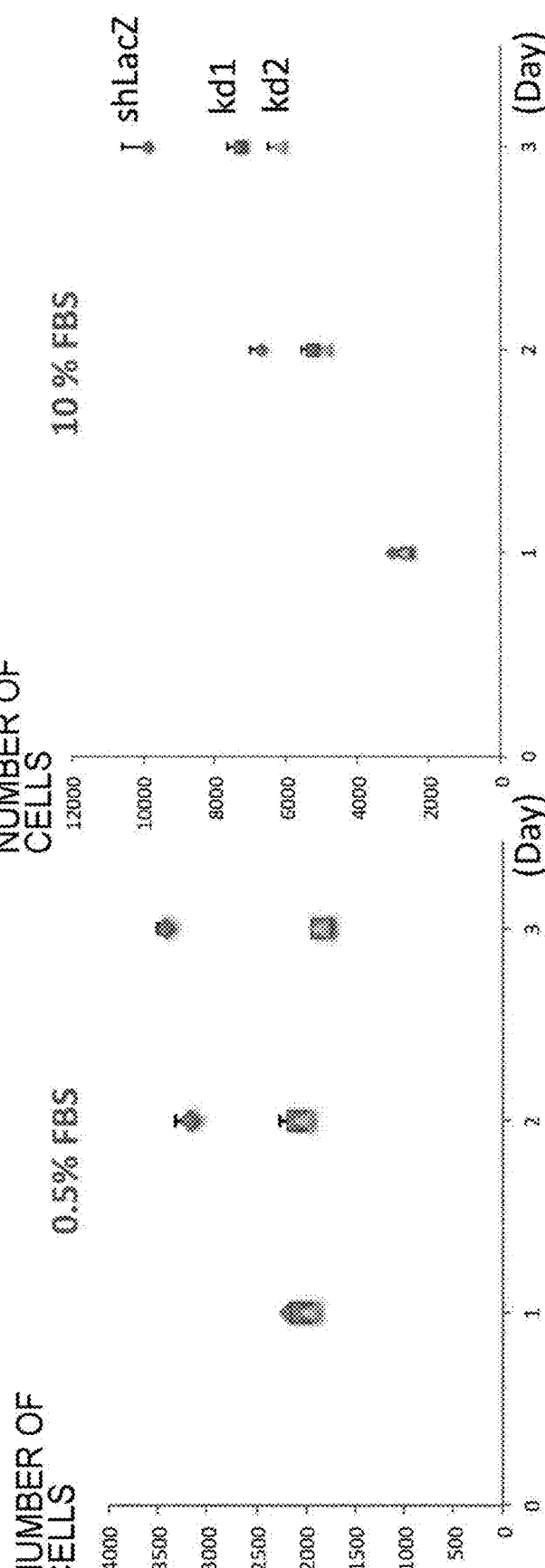
FIG. 9 shows the results of comparing changes in the numbers of cells proliferated when LAMC2 gene expression was suppressed while culturing Skov3 cells under nutrient starvation (0.5% FBS) and normal conditions (10% FBS) (scr: control; Kd1, kd2: Ln-γ2F expression suppression). 1,000 cells were seeded for each case, and the numbers of cells after 1, 2, and 3 days were counted. When Ln-γ2F expression was suppressed, the proliferative potential of the cells was reduced under both nutrient starvation (0.5% FBS) and normal conditions (10% FBS).

Subsequently, since it is known that Akt signal regulates various functions such as proliferation, survival, and movement of cancer cells, the influence of the LAMC2-NR6A1 splicing variant of SHORT FORM on cell proliferation was investigated. 1,000 Skov3 cells were seeded for each case, and the numbers of cells after 1, 2, and 3 days were counted. The results are shown in FIG. 9. When the expression of LAMC2 gene was suppressed, the proliferative potential of the cells was reduced under both nutrient starvation (0.5% FBS) and normal conditions (10% FBS).

Figure 10:
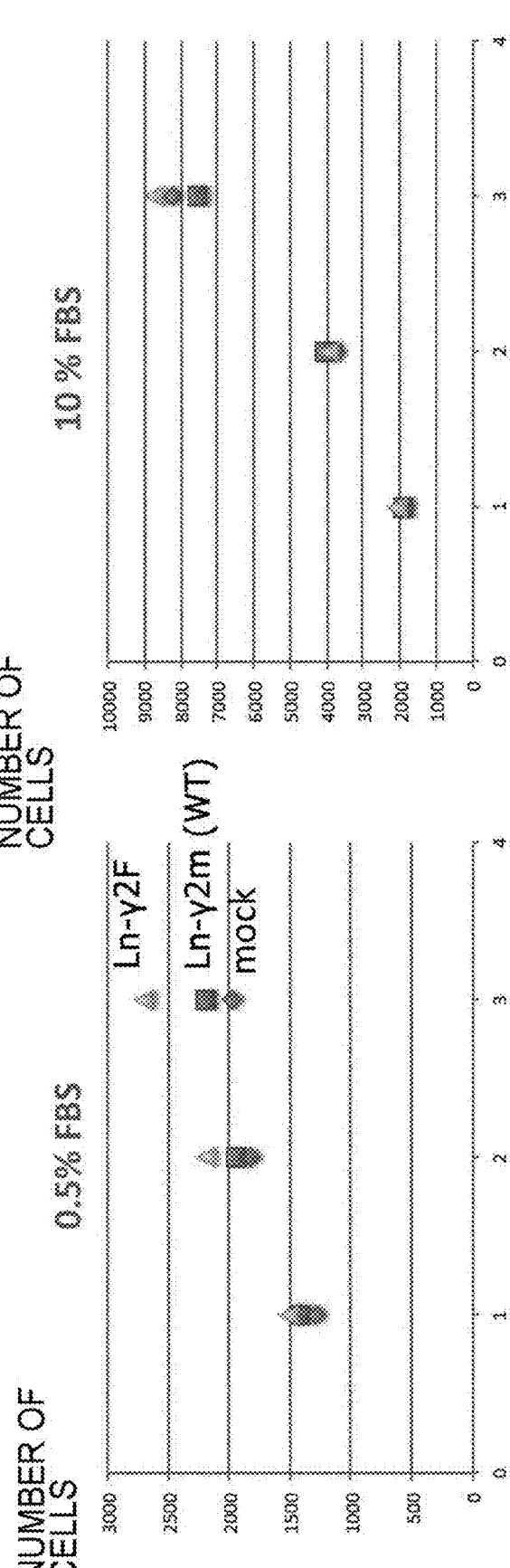
FIG. 10 shows the results of comparing changes in the numbers of cells proliferated when LAMC2 gene expression was forcibly expressed while culturing OVCAR8 cells under nutrient starvation (0.5% FBS) and normal conditions (10% FBS) (Mock: control; WT: LAMC2 Wild type; Fusion: Ln-γ2F). 1,000 cells were seeded for each case, and the numbers of cells after 1, 2, and 3 days were counted. When Ln-γ2F was forcibly expressed, the proliferative potential of the cells was significantly enhanced only in the nutrient starvation (0.5% FBS). The wild type also had a tendency of enhancement, but there was no significant difference therewith.

Subsequently, 1,000 OVCAR8 cells were seeded for each case, and the numbers of cells after 1, 2, and 3 days were counted. The results are shown in FIG. 10. When the LAMC2-NR6A1 splicing variant of SHORT FORM was forcibly expressed, the proliferative potential of the cells was significantly enhanced only in the nutrient starvation (0.5% FBS). The wild type also had a tendency of enhancement, but there was no significant difference therewith.
(Influence on Cell Movement)

Figure 11:
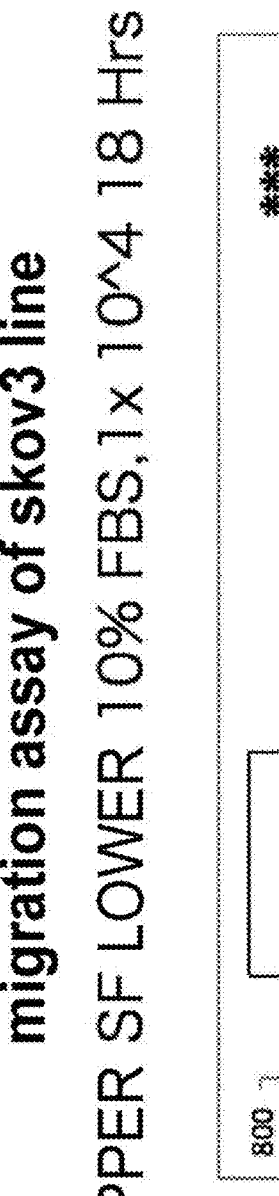
FIG. 11 shows the results of evaluating the motility of cancer cells in a Boyden chamber (scr: control; KD2, KD1: Ln-γ2F expression suppression). The vertical axis represents the numbers of cells migrated.
Figure 11:
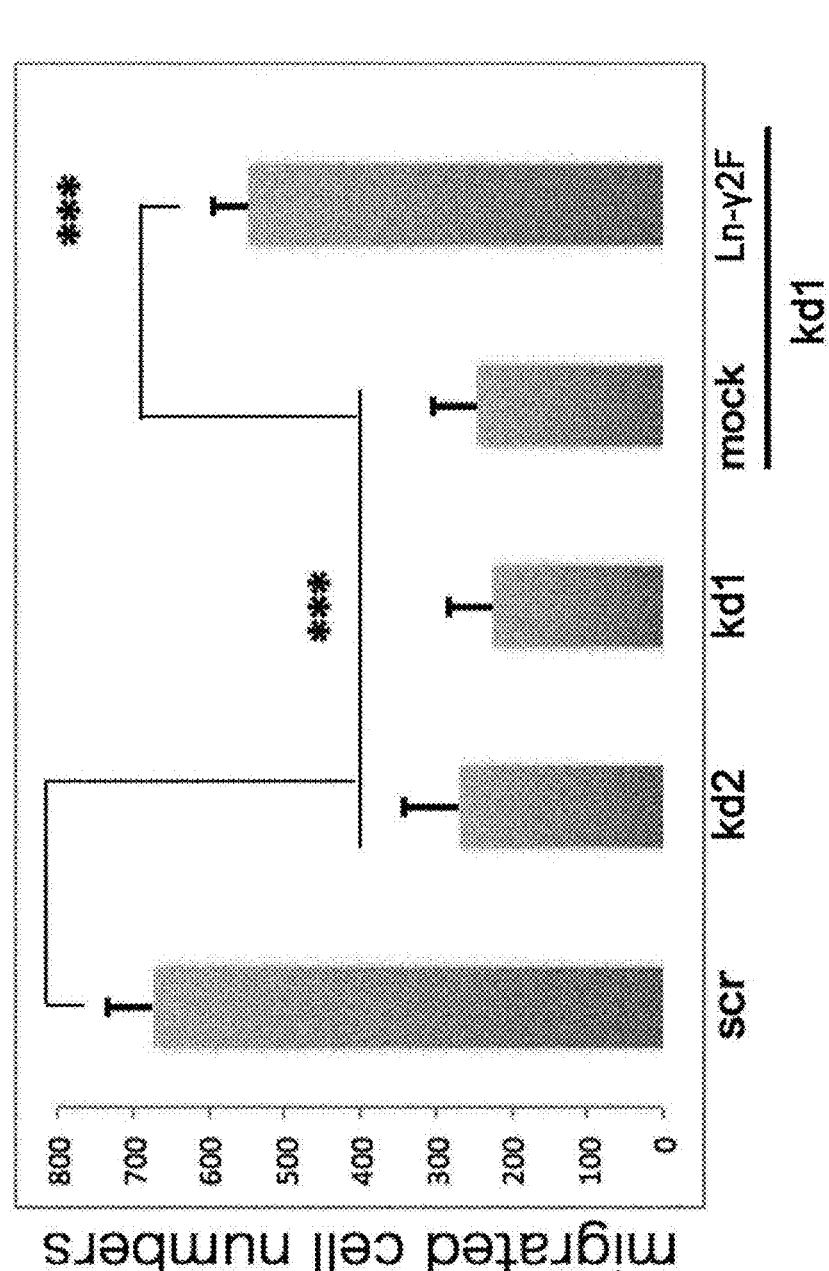

Since the Akt signal is also known to affect the motility of cancer cells, the influence of the LAMC2-NR6A1 splicing variant of SHORT FORM on the motility was evaluated using a Boyden chamber. 10,000 cancer cells were added to each of the upper layers in a serum-free medium, and a medium containing 10% serum was added to the lower layer. The number of cancer cells that had migrated to the lower layer after being cultured for 18 hours was counted. The results are shown in FIG. 11. 671 cancer cells migrated in the control cells, but 267 cancer cells and 224 cancer cells migrated in the LAMC2 gene expression-suppressed lines (kd1 and kd2), respectively. Subsequently, when only the LAMC2-NR6A1 splicing variant of SHORT FORM was returned to the kd2 line, 547 cancer cells migrated to the lower layer. Based on the above description, it became clear that the LAMC2-NR6A1 splicing variant of SHORT FORM regulates the motility of cancer cells.

(Influence on Tumorigenicity)

Figure 12:
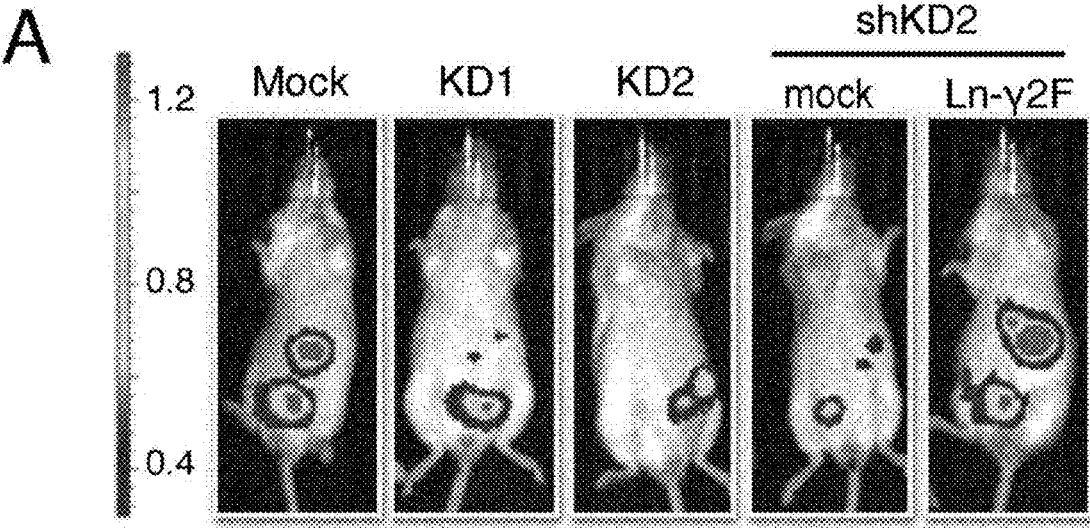
FIG. 12A shows the results of evaluating the influence of Ln-γ2F on the tumorigenicity in a mouse body with ovarian cancer dissemination in the peritoneum (Scr: control; Kd1, kd2: Ln-γ2F expression suppression; Kd2-mock: Ln-γ2F expression suppression+control; Ln-γ2F: Kd2+Fusion: Ln-γ2F expression suppression+Ln-γ2F). Cells expressing luciferase were imaged 6 weeks after transplantation into the peritoneal cavity of scid/beige mice. It is indicated that as the red color (the portion at the tip of the arrow) becomes deeper, more cancer cells are present.
FIG. 12B shows the results of measuring the luminescence intensity of the tumorigenicity in FIG. 12A and graphing it over time.
Figure 12:
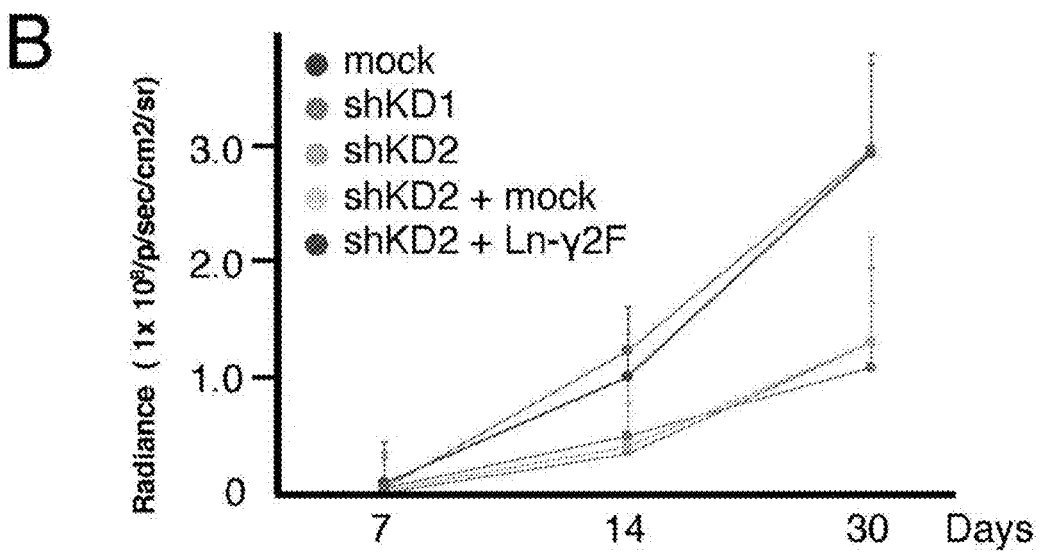

In order to investigate the influence of Ln-γ2F on the tumorigenicity in the living body of mice, 1,000,000 cancer cells were administered to the peritoneal cavity of the scid/beige mouse, and thereafter tumors in the mouse peritoneal cavity were examined after 6 weeks. Since the transplanted cancer cells express the luciferase gene, the tumor size was evaluated by the luminescence signal caused by administration of luciferin. The results are shown in FIG. 12. In the LAMC2 gene expression-suppressed cells (kd1 and kd2), tumor proliferative potential was reduced as compared to the control cells (Mock), and in the cells (Ln-γ2F) in which the expression of Ln-γ2F was returned to the LAMC2 gene expression-suppressed cells, tumor proliferative potential was recovered to the same level as that of the control.

Figure 13:
FIG. 13A shows the results of evaluating the tumorigenicity in mice when Ln-γ2F was expressed in OVCAR8 cells not expressing Ln-γ2F to intraperitoneally transplant the cells into the mice (Mock: control; Ln-γ2F: Ln-γ2F). Cells expressing luciferase were imaged 60 days after transplantation into the peritoneal cavity of scid/beige mice. It is indicated that as the red color (the portion at the tip of the arrow) becomes deeper, more cancer cells are present. When Ln-γ2F was expressed, the tumorigenicity and the tumor engraftment rate increased.
FIG. 13B shows the result of quantitatively determining the luminescence intensity of FIG. 13A.
Figure 13:
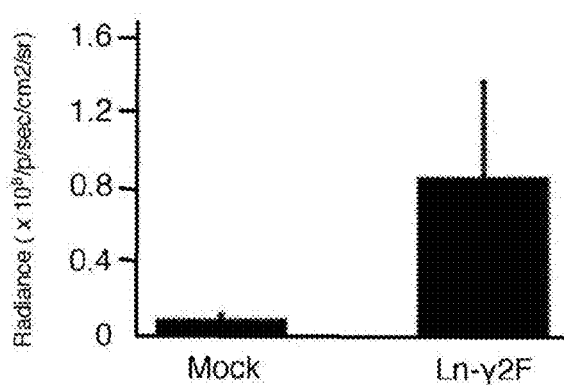

Subsequently, Ln-γ2F was expressed in the OVCAR8 cells not expressing Ln-γ2F, and this was transplanted into the peritoneal cavity of the mouse. When the tumorigenicity in the peritoneal cavity of the mouse was evaluated, the tumor size and the tumor engraftment ability were significantly enhanced in the Ln-γ2F-expressing cells. The results are shown in FIG. 13.

The effect of the present invention will be described assuming a multi-stage carcinogenic model. In the multi-stage carcinogenic model, as the first stage (initiation), DNA was damaged due to carcinogenic substances, UV, and the like in the process of conversion of normal cells into cancer cells. As the second stage (promotion), the proliferation of cancer cells converted by initiation was maintained and increased. As the third stage (progression), movement, invasion, and metastatic potential was increased to cause malignant transformation. Although the specific mechanism of the effect is unclear, from the influence of Ln-γ2F on cell proliferation, motility of cancer cells, and tumor engraftment ability, it was taught that Ln-γ2F is involved in promotion and progression. That is, a function inhibitor (expression inhibition) of Ln-γ2F is expected to have an anticancer effect not only in the primary tumors (promotion stage) but also in the metastatic tumors (progression).

(Ln-γ2F Promotes Activation of AKT and ERK In Vivo)

Figure 17:
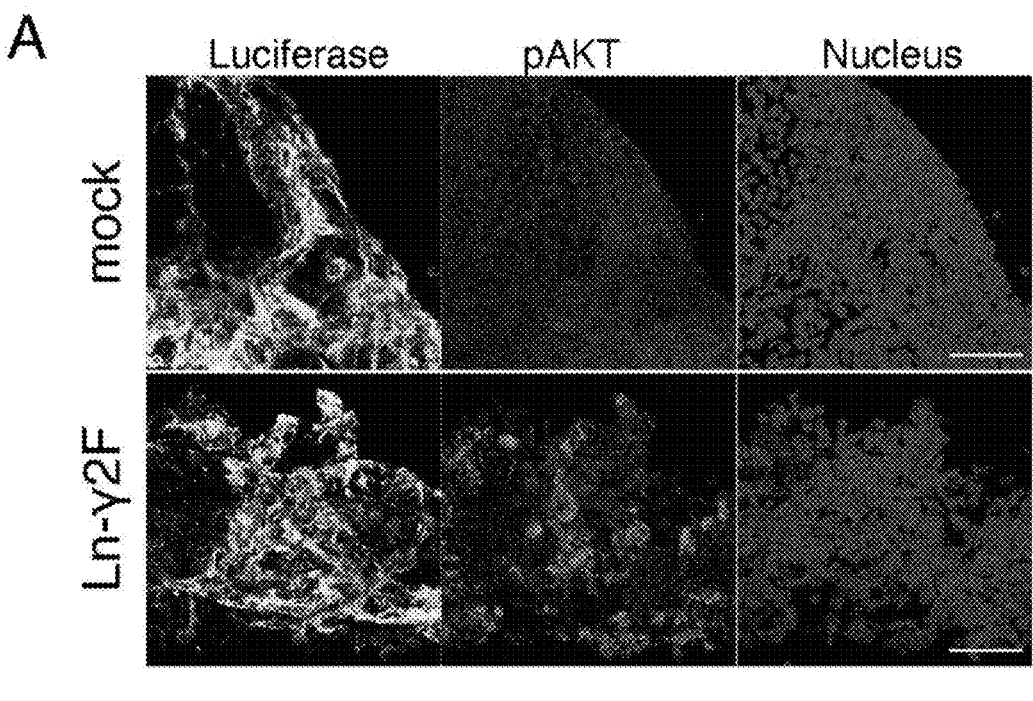
FIG. 17 shows the results of immunostaining tissues recovered 4 weeks after injection of OVCAR8 cells (Mock) and Ln-γ2F-overexpressing cells into the peritoneal cavity of nude mice. Luciferase (green color); phosphorylated AKT (red color in FIG. 17A); phosphorylated ERK (red color in FIG. 17B); nucleus (blue color). Scale bar: 50 μm.
Figure 17:
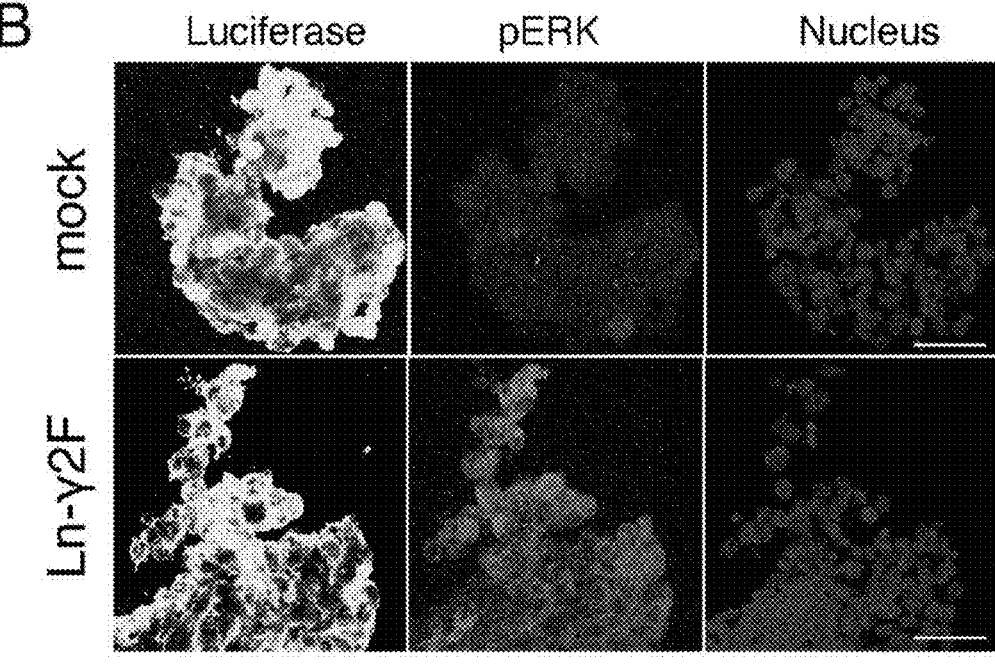

The OVCAR8 cells (Mock) and Ln-γ2F-overexpressing cells were injected into the peritoneal cavity of nude mice. The immunostaining results of the recovered tissue after 4 weeks is shown in FIG. 17. It was shown that the activation of AKT and ERK in the cancer tissue formed in the peritoneal cavity by the Ln-γ2F-overexpressing cells was enhanced as compared to MOCK. Based on the above description, there is a likelihood of Ln-γ2F contributing to the tumorigenicity through the proliferation and survival of cancer cells in vivo.

INDUSTRIAL APPLICABILITY

Since Ln-γ2F is thought to be involved in the malignant transformation of cancer and control the motility of cancer cells, it can also be utilized as a marker for predicting the degree of malignancy of cancer. Furthermore, substances inhibiting the expression of Ln-γ2FF are expected to have the effect of suppressing the invasion and metastasis of cancer.

What is claimed is:

1. A method of detecting a biomarker comprising:

a) obtaining a biological sample from a subject, and b) detecting in said biological sample, a biomarker selected from the group consisting of (i) a nucleic acid molecule comprising SEQ ID NO: 2 or SEQ ID NO: 6, (ii) a protein encoded by the nucleic acid molecule comprising SEQ ID NO: 2 or SEQ ID NO: 6, (iii) a protein comprising SEQ ID NO: 3 or SEQ ID NO: 7, (iv) a peptide comprising SEQ ID NO: 4, and (v) a nucleic acid encoding the peptide or protein comprising SEQ ID NO: 3, SEQ ID NO: 4, or SEQ ID NO: 7.

* * * * *